United States Patent
Zumbrunn et al.

(10) Patent No.: US 9,518,092 B2
(45) Date of Patent: Dec. 13, 2016

(54) TEMPLATE-FIXED BETA-HAIRPIN PEPTIDOMIMETICS WITH CXCR4 ANTAGONIZING ACTIVITY

(71) Applicants: Polyphor Ltd., Allschwil (CH); Universität Zürich, Zürich (CH)

(72) Inventors: Jürg Zumbrunn, Känerkinden (CH); Steven J. Demarco, Diegten (CH); Sergio Lociuro, Reinach (CH); Jan Wim Vrijbloed, Möhlin (CH); Frank Gombert, Huttingen (DE); Reshmi Mukherjee, Newton, MA (US); Kerstin Moehle, Wettswil (CH); Daniel Obrecht, Bättwil (CH); John Anthony Robinson, Wermatswil (CH); Heiko Henze, Zürich (CH); Barbara Romagnoli, St. Louis (FR); Christian Ludin, Oberwil (CH)

(73) Assignees: POLYPHOR LTD., Allschwil (CH); UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 14/495,737

(22) Filed: Sep. 24, 2014

(65) Prior Publication Data
US 2015/0087577 A1 Mar. 26, 2015

Related U.S. Application Data

(60) Continuation of application No. 12/828,998, filed on Jul. 1, 2010, now Pat. No. 8,895,695, which is a division of application No. 10/555,088, filed as application No. PCT/EP2004/004535 on Apr. 29, 2004, now Pat. No. 7,786,078.

(30) Foreign Application Priority Data

May 2, 2003 (WO) .................. PCT/EP03/04640

(51) Int. Cl.
*C07K 7/08* (2006.01)
*C07K 7/64* (2006.01)
*C07K 1/04* (2006.01)
*A61K 38/00* (2006.01)

(52) U.S. Cl.
CPC .............. *C07K 7/64* (2013.01); *C07K 1/047* (2013.01); *C07K 7/08* (2013.01); *A61K 38/00* (2013.01)

(58) Field of Classification Search
CPC ................... C07K 7/08; C07K 7/64
USPC ............................. 530/327, 317
See application file for complete search history.

(56) References Cited

U.S. PATENT DOCUMENTS

| 7,253,146 B2 | 8/2007 | Obrecht et al. |
| 2004/0171066 A1 | 9/2004 | Obrecht et al. |

FOREIGN PATENT DOCUMENTS

| WO | 01/16161 A1 | 3/2001 |
| WO | 02/070547 A1 | 9/2002 |
| WO | 03/054000 A1 | 7/2003 |
| WO | 2004/018503 A1 | 3/2004 |
| WO | 2004/033489 A1 | 4/2004 |

OTHER PUBLICATIONS

Dörwald, F. Zaragoza, "Side Reactions in Organic Synthesis," 2005, Wiley-VCH, Preface (p. ix).
Fujii & Tamamura, "Peptide-lead CXCR4 antagonists with high anti-HIV activity," Current Opinion in Investigational Drugs 2001 2(9), pp. 1198-1202.
International Search Report for PCT/EP2004/004535 mailed Aug. 18, 2004.
Messer, Jr., Dr. William S., "MBC 3320 Posterior pituitary hormones," "Vasopressin and Oxytocin," Apr. 3, 2000; <http://www.neurosci.pharm.utoledo.edu/MBC3320/vasopressin.htm> pp. 1-5.
Obrecht, et al., "Design and Synthesis of Novel Nonpolar Host Peptides for the Determination of the 310- and α-Helix Compatibilities of α-Amino Acid Building Blocks: An Assessment of a, α-Disubstituted Glycines" Biopolymers, 42: 575-626, 1997.
Oishi, et al., "Discovery of a Novel CXCR4 Antagonist Using Two Orthogonal Cyclic Peptide Libraries," Biopolymers, vol. 71, No. 3, 2003, p. 373 XP-002290384.
Rudikoff, et al., "Single amino acid substitution altering antigen-binding specificity," Proc. Natl. Acad. Sci. USA vol. 79, pp. 1979-1983, Mar. 1982 Immunology.
J. Rudringer, "Characteristics of the amino acids as components of a peptide hormone sequence," Peptide Hormones, Edited by J.A. Parsons, M.A., B.M., B. Ch. (1976) pp. 1-7.

(Continued)

Primary Examiner — David Lukton
(74) Attorney, Agent, or Firm — Hoffman & Baron, LLP

(57) ABSTRACT

Template-fixed β-hairpin peptidomimetics of the general formula (I)

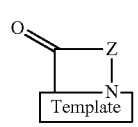

wherein Z is a template-fixed chain of 12, 14 or 18 α-amino acid residues which, depending on their positions in the chain (counted starting from the N-terminal amino acid), are Gly, NMeGly, Pro or Pip, or of certain types which, as the remaining symbols in the above formula, are defined in the description and the claims, and salts thereof, have CXCR4 antagonizing properties These β-hairpin peptidomimetics can be manufactured by a process which is based on a mixed solid- and solution phase synthetic strategy.

12 Claims, No Drawings

(56) References Cited

OTHER PUBLICATIONS

Smilek, Dawn E. et al., "A single amino acid change in a myelin basic protein peptide confers the capacity to prevent rather than induce experimental autoimmune encephalomyelitis," Proc. Natl. Acad. Sci. USA, vol. 88, pp. 9633-9637, Nov. 1991 Immunology.

Spath et al., "Stabilization of a β-Hairpin Conformation in a Cyclic Peptide Using the Templating Effect of a Heterochiral Diproline Unit," Helvetica Chimica Acta, vol. 81 (1998) pp. 1726-1738.

Tamamura et al., "Certification of the Critical Importance of L-3-(2-Naphthyl)alanine at Position 3 of a Specific CXCR4 Inhibitor, T140, Leads to an Exploratory Performance of Its Downsizing Study," Bioorganic & Medicinal Chemistry 10 (2002) pp. 1417-1426.

Tamamura et al., "Conformational Study of a Highly Specific CXCR4 Inhibitor, T140, Disclosing the Close Proximity of Its Intrinsic Pharmacophores Associated with Strong Anti-HIV Activity," Bioorganic & Medicinal Chemistry Letters 11 (2001) pp. 359-362.

Tamamura et al., "Development of Specific CXCR4 Inhibitors Possessing High Selectivity Indexes as Well as Complete Stability in Serum Based on an Anti-HIV Peptide T140," Bioorganic & Medicinal Chemistry Letters 11 (2001) 1897-1902.

Tamamura et al., "Synthesis and Evaluation of Pseudopeptide Analogues of a Specific CXCR4 Inhibitor, T140: The Insertion of an (E)-Alkene Dipeptide Isostere into the βII'-Turn Moiety," Bioorganic & Medicinal Chemistry Letters 12 (2002) pp. 923-928.

International Preliminary Report on Patentability for PCT/EP2004/004535 (date of completion report: Apr. 22, 2005).

SEQUENCE LISTING

```
<160> NUMBER OF SEQ ID NOS: 160

<210> SEQ ID NO 1
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = D-Arg
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 1

Tyr Arg Xaa Val Arg Xaa Arg Xaa Phe Tyr Xaa Lys Xaa Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = D-Arg
```

```
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 2

Tyr Arg Xaa Val Arg Xaa Arg Xaa Val Tyr Xaa Lys Xaa Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 3

Tyr Arg Xaa Phe Arg Arg Arg Xaa Phe Tyr Xaa Lys Xaa Pro
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 4

Tyr Arg Xaa Val Arg Arg Arg Xaa Phe Tyr Xaa Lys Xaa Pro
1               5                   10

<210> SEQ ID NO 5
<211> LENGTH: 14
```

```
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 5

Tyr Arg Xaa Phe Arg Arg Arg Xaa Val Tyr Xaa Lys Xaa Pro
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 6

Tyr Arg Xaa Val Arg Arg Arg Xaa Val Tyr Xaa Lys Xaa Pro
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(9)
<223> OTHER INFORMATION: Cys in pos. 4 and 9 form a disulfid bridge.
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
```

```
<221> NAME/KEY: MISC_FEATURE
<222> LOCATION: (13)..(13)
<223> OTHER INFORMATION: Xaa = D-Pro

<400> SEQUENCE: 7

Tyr Arg Xaa Cys Arg Arg Arg Xaa Cys Tyr Xaa Lys Xaa Pro
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 8

Tyr Arg Xaa Gly Arg Arg Arg Xaa Gly Tyr Xaa Lys Xaa Pro
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 9

Tyr Arg Xaa Ile Arg Arg Arg Xaa Ile Tyr Xaa Lys Xaa Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
```

```
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 10

Tyr Arg Xaa Thr Arg Arg Arg Xaa Thr Tyr Xaa Lys Xaa Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 11

Tyr Arg Xaa Gln Arg Arg Arg Xaa Gln Tyr Xaa Lys Xaa Pro
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(9)
<223> OTHER INFORMATION: Cys in pos. 4 and 9 form a disulfid bridge.
<220> FEATURE:
<221> NAME/KEY: MISC_FEATURE
<222> LOCATION: (6)..(6)
<223> OTHER INFORMATION: Xaa = D-Arg
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 12
```

```
Tyr Arg Xaa Cys Arg Xaa Arg Xaa Cys Tyr Xaa Lys Xaa Pro
1               5                   10
```

<210> SEQ ID NO 13
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(9)
<223> OTHER INFORMATION: Cys in pos. 4 and 9 form a disulfid bridge.
<220> FEATURE:
<221> NAME/KEY: MISC_FEATURE
<222> LOCATION: (8)..(8)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = D-Pro

<400> SEQUENCE: 13

```
Tyr Gly Xaa Cys Arg Arg Arg Xaa Cys Tyr Gly Lys Xaa Pro
1               5                   10
```

<210> SEQ ID NO 14
<211> LENGTH: 14
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(9)
<223> OTHER INFORMATION: Cys in pos. 4 and 9 form a disulfid bridge.
<220> FEATURE:
<221> NAME/KEY: MISC_FEATURE
<222> LOCATION: (11)..(11)
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = D-Pro

<400> SEQUENCE: 14

```
Tyr Arg Xaa Cys Arg Arg Arg Trp Cys Tyr Xaa Lys Xaa Pro
1               5                   10
```

<210> SEQ ID NO 15
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE

```
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 15

Tyr Arg Xaa Val Arg Val Xaa Arg Arg Xaa Val Tyr Xaa Lys Xaa Pro
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 16

Tyr Arg Xaa Val Arg Val Pro Arg Arg Xaa Val Tyr Xaa Lys Xaa Pro
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 17

Tyr Arg Xaa Val Arg Phe Xaa Arg Arg Xaa Val Tyr Xaa Lys Xaa Pro
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 18

Tyr Arg Xaa Val Arg Phe Pro Arg Arg Xaa Val Tyr Xaa Lys Xaa Pro
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 19

Tyr Arg Xaa Phe Arg Xaa Xaa Arg Arg Xaa Val Tyr Xaa Lys Xaa Pro
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
```

```
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 20

Tyr Arg Xaa Phe Arg Xaa Pro Arg Arg Xaa Val Tyr Xaa Lys Xaa Pro
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 21

Tyr Arg Xaa Phe Arg Val Xaa Arg Arg Xaa Val Tyr Xaa Lys Xaa Pro
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 22

Tyr Arg Xaa Phe Arg Val Pro Arg Arg Xaa Val Tyr Xaa Lys Xaa Pro
```

```
<210> SEQ ID NO 23
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 23

Tyr Arg Xaa Phe Arg Phe Xaa Arg Arg Xaa Val Tyr Xaa Lys Xaa Pro
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 24

Tyr Arg Xaa Phe Arg Phe Pro Arg Arg Xaa Val Tyr Xaa Lys Xaa Pro
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
```

```
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 25

Tyr Arg Xaa Val Arg Xaa Xaa Arg Arg Xaa Val Tyr Xaa Lys Xaa Pro
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 26

Tyr Arg Xaa Val Arg Xaa Pro Arg Arg Xaa Val Tyr Xaa Lys Xaa Pro
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
```

<221> NAME/KEY: MISC_FEATURE
<222> LOCATION: (15)..(15)
<223> OTHER INFORMATION: Xaa = D-Pro

<400> SEQUENCE: 27

Tyr Arg Xaa Phe Arg Val Xaa Arg Arg Xaa Phe Tyr Xaa Lys Xaa Pro
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 28

Tyr Arg Xaa Phe Arg Val Pro Arg Arg Xaa Phe Tyr Xaa Lys Xaa Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 29

Tyr Arg Xaa Phe Arg Phe Xaa Arg Arg Xaa Phe Tyr Xaa Lys Xaa Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:

```
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 30

Tyr Arg Xaa Phe Arg Phe Pro Arg Arg Xaa Phe Tyr Xaa Lys Xaa Pro
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 31

Tyr Arg Xaa Val Arg Xaa Pro Arg Arg Xaa Phe Tyr Xaa Lys Xaa Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
```

```
<222> LOCATION: (15)..(15)
<223> OTHER INFORMATION: Xaa = D-Pro

<400> SEQUENCE: 32

Tyr Arg Xaa Val Arg Val Xaa Arg Arg Xaa Phe Tyr Xaa Lys Xaa Pro
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 33

Tyr Arg Xaa Val Arg Val Pro Arg Arg Xaa Phe Tyr Xaa Lys Xaa Pro
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 34

Tyr Arg Xaa Val Arg Phe Xaa Arg Arg Xaa Phe Tyr Xaa Lys Xaa Pro
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
```

```
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 35

Tyr Arg Xaa Val Arg Phe Pro Arg Arg Xaa Phe Tyr Xaa Lys Xaa Pro
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 36

Tyr Arg Xaa Phe Arg Xaa Xaa Arg Arg Xaa Phe Tyr Xaa Lys Xaa Pro
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
```

```
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 37

Tyr Arg Xaa Phe Arg Xaa Pro Arg Arg Xaa Phe Tyr Xaa Lys Xaa Pro
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 38

Tyr Arg Xaa Phe Arg Gly Xaa Arg Arg Xaa Phe Tyr Xaa Lys Xaa Pro
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 39

Tyr Arg Xaa Phe Arg Gly Gly Arg Arg Xaa Phe Tyr Xaa Lys Xaa Pro
1               5                   10                  15

<210> SEQ ID NO 40
<211> LENGTH: 16
<212> TYPE: PRT
<213> ORGANISM: Artificial Sequence
<220> FEATURE:
```

```
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 40

Tyr Arg Xaa Phe Arg Val Gly Arg Arg Xaa Phe Tyr Xaa Lys Xaa Pro
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 41

Tyr Arg Xaa Tyr Arg Pro Val Arg Arg Xaa Tyr Tyr Xaa Lys Xaa Pro
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 42

Tyr Arg Xaa Tyr Arg Pro Val Arg Arg Xaa Tyr Tyr Xaa Lys Xaa Pro
```

```
                1               5                  10                  15
```

<210> SEQ ID NO 43
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 43

```
Tyr Arg Xaa Tyr Arg Val Gly Arg Arg Xaa Tyr Xaa Lys Xaa Pro
1               5                   10                  15
```

<210> SEQ ID NO 44
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 44

```
Tyr Arg Xaa Val Arg Pro Val Arg Arg Xaa Val Tyr Xaa Lys Xaa Pro
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal

```
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 45

Tyr Arg Xaa Val Arg Gly Xaa Arg Arg Xaa Val Tyr Xaa Lys Xaa Pro
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 46

Tyr Arg Xaa Val Arg Gly Gly Arg Arg Xaa Val Tyr Xaa Lys Xaa Pro
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 47

Tyr Arg Xaa Val Arg Val Gly Arg Arg Xaa Val Tyr Xaa Lys Xaa Pro
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Cyclic template fixed peptidomimetic
```

```
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (4)..(4)
<223> OTHER INFORMATION: Xaa = t-BuG
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = t-BuG
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 48

Tyr Arg Xaa Xaa Arg Pro Val Arg Arg Xaa Xaa Tyr Xaa Lys Xaa Pro
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (4)..(4)
<223> OTHER INFORMATION: Xaa = t-BuG
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = t-BuG
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 49

Tyr Arg Xaa Xaa Arg Gly Gly Arg Arg Xaa Xaa Tyr Xaa Lys Xaa Pro
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
```

```
<221> NAME/KEY: MISC_FEATURE
<222> LOCATION: (4)..(4)
<223> OTHER INFORMATION: Xaa = t-BuG
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (11)..(11)
<223> OTHER INFORMATION: Xaa = t-BuG
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 50

Tyr Arg Xaa Xaa Arg Val Gly Arg Arg Xaa Xaa Tyr Xaa Lys Xaa Pro
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 51

Tyr Arg Xaa Cys Arg Gly Xaa Arg Arg Xaa Cys Tyr Xaa Lys Xaa Pro
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
```

```
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 52

Tyr Arg Xaa Cys Arg Gly Gly Arg Arg Xaa Cys Tyr Xaa Lys Xaa Pro
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 53

Tyr Arg Xaa Cys Arg Val Gly Arg Arg Xaa Cys Tyr Xaa Lys Xaa Pro
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 54
```

Tyr Arg Xaa Cys Arg Gly Xaa Tyr Arg Xaa Cys Tyr Gln Lys Xaa Pro
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 55

Tyr Arg Xaa Cys Arg Gly Xaa Trp Arg Xaa Cys Tyr Gln Lys Xaa Pro
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 56

Tyr Arg Xaa Cys Arg Gly Xaa Thr Arg Xaa Cys Tyr Gln Lys Xaa Pro
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)

```
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 57

Tyr Arg Xaa Cys Arg Gly Xaa Arg Arg Xaa Cys Tyr Arg Lys Xaa Pro
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 58

Tyr Arg Xaa Cys Arg Gly Xaa Arg Arg Xaa Cys Tyr His Lys Xaa Pro
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
```

```
<220> FEATURE:
<221> NAME/KEY: MISC_FEATURE
<222> LOCATION: (15)..(15)
<223> OTHER INFORMATION: Xaa = D-Pro

<400> SEQUENCE: 59

Tyr Arg Xaa Cys Arg Gly Xaa Arg Arg Xaa Cys Tyr Tyr Lys Xaa Pro
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 60

Tyr Arg Xaa Cys Arg Gly Xaa Arg Arg Xaa Cys Tyr Gln Gln Xaa Pro
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 61

Tyr Arg Xaa Cys Arg Gly Xaa Arg Arg Xaa Cys Tyr Gln Glu Xaa Pro
1               5                   10                  15

<210> SEQ ID NO 62
<211> LENGTH: 16
```

-continued

```
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 62

Gln Arg Xaa Cys Arg Gly Xaa Arg Arg Xaa Cys Tyr Gln Lys Xaa Pro
 1               5                  10                  15

<210> SEQ ID NO 63
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 63

Arg Arg Xaa Cys Arg Gly Xaa Arg Arg Xaa Cys Tyr Gln Lys Xaa Pro
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
```

```
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 64

His Arg Xaa Cys Arg Gly Xaa Arg Arg Xaa Cys Tyr Gln Lys Xaa Pro
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 65

Ile Arg Xaa Cys Arg Gly Xaa Arg Arg Xaa Cys Tyr Gln Lys Xaa Pro
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 66
```

Trp Arg Xaa Cys Arg Gly Xaa Arg Arg Xaa Cys Tyr Gln Lys Xaa Pro
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 67

Thr Arg Xaa Cys Arg Gly Xaa Arg Arg Xaa Cys Tyr Gln Lys Xaa Pro
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 68

Glu Arg Xaa Cys Arg Gly Xaa Arg Arg Xaa Cys Tyr Gln Lys Xaa Pro
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID

```
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 69

Tyr Arg Arg Cys Arg Gly Xaa Arg Arg Xaa Cys Tyr Gln Lys Xaa Pro
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 70

Tyr Arg His Cys Arg Gly Xaa Arg Arg Xaa Cys Tyr Gln Lys Xaa Pro
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 71

Tyr Arg Ile Cys Arg Gly Xaa Arg Arg Xaa Cys Tyr Gln Lys Xaa Pro
1               5                   10                  15
```

```
<210> SEQ ID NO 72
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 72

Tyr Arg Tyr Cys Arg Gly Xaa Arg Arg Xaa Cys Tyr Gln Lys Xaa Pro
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 73

Tyr Arg Trp Cys Arg Gly Xaa Arg Arg Xaa Cys Tyr Gln Lys Xaa Pro
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
```

-continued

```
<223> OTHER INFORMATION: Xaa = D-Pro

<400> SEQUENCE: 74

Tyr Arg Pro Cys Arg Gly Xaa Arg Arg Xaa Cys Tyr Gln Lys Xaa Pro
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 75

Tyr Arg Glu Cys Arg Gly Xaa Arg Arg Xaa Cys Tyr Gln Lys Xaa Pro
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = 4F-Phe
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 76

Tyr Arg Xaa Cys Arg Gly Xaa Xaa Arg Xaa Cys Tyr Gln Lys Xaa Pro
1               5                   10                  15

<210> SEQ ID NO 77
<211> LENGTH: 16
<212> TYPE: PRT
<213> ORGANISM: Artificial Sequence
<220> FEATURE:
```

```
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 77

Tyr Arg Xaa Cys Arg Gly Xaa Arg Arg Xaa Cys Tyr Asn Lys Xaa Pro
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 78

Tyr Arg Xaa Cys Arg Gly Xaa Arg Arg Xaa Cys Tyr Asp Lys Xaa Pro
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
```

```
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 79

Tyr Arg Xaa Cys Arg Gly Xaa Arg Arg Xaa Cys Tyr Lys Lys Xaa Pro
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 80

Tyr Arg Xaa Cys Arg Gly Xaa Arg Arg Xaa Cys Tyr Ala Lys Xaa Pro
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 81

Tyr Arg Xaa Cys Arg Gly Xaa Arg Arg Xaa Cys Tyr Ser Lys Xaa Pro
1               5                   10                  15
```

```
<210> SEQ ID NO 82
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 82

Tyr Arg Xaa Cys Arg Gly Xaa Arg Arg Xaa Cys Tyr Leu Lys Xaa Pro
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 83

Tyr Arg Xaa Cys Arg Gly Xaa Arg Arg Xaa Cys Tyr Met Lys Xaa Pro
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
```

```
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 84

Tyr Arg Xaa Cys Arg Gly Xaa Arg Arg Xaa Cys Tyr Gln Asn Xaa Pro
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 85

Tyr Arg Xaa Cys Arg Gly Xaa Arg Arg Xaa Cys Tyr Gln Asp Xaa Pro
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
```

```
<222> LOCATION: (15)..(15)
<223> OTHER INFORMATION: Xaa = D-Pro

<400> SEQUENCE: 86

Tyr Arg Xaa Cys Arg Gly Xaa Arg Arg Xaa Cys Tyr Gln Ala Xaa Pro
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 87

Tyr Arg Xaa Cys Arg Gly Xaa Arg Arg Xaa Cys Tyr Gln Ser Xaa Pro
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 88

Asp Arg Xaa Cys Arg Gly Xaa Arg Arg Xaa Cys Tyr Gln Lys Xaa Pro
1               5                   10                  15

<210> SEQ ID NO 89
<211> LENGTH: 16
<212> TYPE: PRT
<213> ORGANISM: Artificial Sequence
```

```
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 89

Ser Arg Xaa Cys Arg Gly Xaa Arg Arg Xaa Cys Tyr Gln Lys Xaa Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 90

Val Arg Xaa Cys Arg Gly Xaa Arg Arg Xaa Cys Tyr Gln Lys Xaa Pro
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
```

```
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 91

Met Arg Xaa Cys Arg Gly Xaa Arg Arg Xaa Cys Tyr Gln Lys Xaa Pro
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 92

Tyr Arg Asn Cys Arg Gly Xaa Arg Arg Xaa Cys Tyr Gln Lys Xaa Pro
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 93

Tyr Arg Asp Cys Arg Gly Xaa Arg Arg Xaa Cys Tyr Gln Lys Xaa Pro
1               5                   10                  15

<210> SEQ ID NO 94
<211> LENGTH: 16
<212> TYPE: PRT
<213> ORGANISM: Artificial Sequence
<220> FEATURE:
```

```
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 94

Tyr Arg Lys Cys Arg Gly Xaa Arg Arg Xaa Cys Tyr Gln Lys Xaa Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 95

Tyr Arg Ala Cys Arg Gly Xaa Arg Arg Xaa Cys Tyr Gln Lys Xaa Pro
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 96

Tyr Arg Ser Cys Arg Gly Xaa Arg Arg Xaa Cys Tyr Gln Lys Xaa Pro
```

<210> SEQ ID NO 97
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 97

Tyr Arg Leu Cys Arg Gly Xaa Arg Arg Xaa Cys Tyr Gln Lys Xaa Pro
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 98

Tyr Arg Val Cys Arg Gly Xaa Arg Arg Xaa Cys Tyr Gln Lys Xaa Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = 4F-Phe
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro

```
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 99

Tyr Arg Xaa Cys Arg Gly Xaa Arg Arg Xaa Cys Tyr Gln Lys Xaa Pro
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 100

Tyr Arg Met Cys Arg Gly Xaa Arg Arg Xaa Cys Tyr Gln Lys Xaa Pro
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 101

Tyr Arg Xaa Cys Ser Gly Xaa Arg Arg Xaa Cys Tyr Gln Lys Xaa Pro
1               5                   10                  15

<210> SEQ ID NO 102
<211> LENGTH: 16
```

```
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 102

Tyr Arg Ser Cys Arg Gly Xaa Arg Arg Trp Cys Tyr Xaa Asp Xaa Pro
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 103

Tyr Arg Xaa Cys Arg Gly Xaa Arg Arg Xaa Cys Tyr Xaa Glu Xaa Pro
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
```

```
<221> NAME/KEY: MISC_FEATURE
<222> LOCATION: (8)..(8)
<223> OTHER INFORMATION: Xaa = Dab
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 104

Tyr Arg Thr Cys Arg Gly Xaa Xaa Arg Xaa Cys Tyr Gln Lys Xaa Pro
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 105

Tyr His Xaa Cys Arg Gly Xaa Arg Arg Trp Cys Tyr Xaa Lys Xaa Pro
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 106
```

```
Tyr Lys Xaa Cys Arg Gly Xaa Arg Arg Trp Cys Tyr Xaa Lys Xaa Pro
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 107

Phe Arg Xaa Cys Arg Gly Xaa Arg Arg Trp Cys Tyr Xaa Lys Xaa Pro
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 108

Tyr Arg Xaa Cys Arg Gly Xaa Arg Arg Trp Cys Tyr Gln Lys Xaa Pro
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
```

<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = Dab
<220> FEATURE:
<221> NAME/KEY: MISC_FEATURE
<222> LOCATION: (15)..(15)
<223> OTHER INFORMATION: Xaa = D-Pro

<400> SEQUENCE: 109

Tyr Arg Xaa Cys Arg Gly Xaa Xaa Arg Trp Cys Tyr Gln Lys Xaa Pro
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = Dab
<220> FEATURE:
<221> NAME/KEY: MISC_FEATURE
<222> LOCATION: (15)..(15)
<223> OTHER INFORMATION: Xaa = D-Pro

<400> SEQUENCE: 110

Tyr Arg Thr Cys Arg Gly Xaa Xaa Arg Trp Cys Tyr Gln Lys Xaa Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (5)..(5)
<223> OTHER INFORMATION: Xaa = Dab
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 111

Tyr Arg Xaa Cys Xaa Gly Xaa Arg Arg Trp Cys Tyr Gln Lys Xaa Pro
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 112

Tyr Arg Xaa Cys Arg Gly Xaa Arg Arg Tyr Cys Tyr Xaa Lys Xaa Pro
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (12)..(12)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 113

Tyr Arg Xaa Cys Arg Gly Xaa Arg Arg Tyr Cys Xaa Tyr Lys Xaa Pro
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)

```
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 114

Gly Arg Xaa Cys Arg Gly Xaa Arg Arg Xaa Cys Tyr Xaa Lys Xaa Pro
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 115

Tyr Arg Xaa Cys Arg Gly Xaa Arg Arg Xaa Cys Tyr Gln Lys Xaa Pro
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
```

```
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro
<220> FEATURE:
<221> NAME/KEY: MISC_FEATURE
<222> LOCATION: (16)..(16)
<223> OTHER INFORMATION: Xaa = A8″-42

<400> SEQUENCE: 116

Tyr Arg Xaa Cys Arg Gly Xaa Arg Arg Trp Cys Tyr Xaa Lys Xaa Xaa
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (9)..(9)
<223> OTHER INFORMATION: Xaa = Orn
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 117

Tyr Arg Xaa Cys Arg Gly Xaa Arg Xaa Trp Cys Tyr Xaa Lys Xaa Pro
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = 4-PyrAla
<220> FEATURE:
<221> NAME/KEY: MISC_FEATURE
<222> LOCATION: (15)..(15)
<223> OTHER INFORMATION: Xaa = D-Pro
```

```
<400> SEQUENCE: 118

Tyr Arg Thr Cys Arg Gly Xaa Xaa Arg Trp Cys Tyr Gln Lys Xaa Pro
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (2)..(2)
<223> OTHER INFORMATION: Xaa = 4-PyrAla
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 119

Tyr Xaa Thr Cys Arg Gly Xaa Arg Arg Trp Cys Tyr Gln Lys Xaa Pro
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 120

Tyr His Thr Cys Arg Gly Xaa Arg His Trp Cys Tyr Gln Lys Xaa Pro
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
```

<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 121

Tyr Arg Xaa Cys Arg Gly Xaa Arg Arg Trp Cys Tyr Xaa Gln Xaa Pro
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = 4F-Phe
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 122

Tyr Arg Xaa Cys Arg Gly Xaa Xaa Arg Trp Cys Tyr Xaa Lys Xaa Pro
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 123

Tyr Arg Xaa Cys Arg Gly Xaa Arg Arg Trp Cys Tyr Xaa Lys Xaa Pro
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = IsOrn
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 124

Tyr Arg Xaa Cys Arg Gly Xaa Xaa Arg Xaa Cys Tyr Xaa Lys Xaa Pro
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = (Im)G
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)

```
<223> OTHER INFORMATION: Xaa = D-Pro

<400> SEQUENCE: 125

Tyr Arg Xaa Cys Arg Gly Xaa Xaa Arg Xaa Cys Tyr Xaa Lys Xaa Pro
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (9)..(9)
<223> OTHER INFORMATION: Xaa = (Pip)G
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 126

Tyr Arg Xaa Cys Arg Gly Xaa Arg Xaa Xaa Cys Tyr Xaa Lys Xaa Pro
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (14)..(14)
<223> OTHER INFORMATION: Xaa = NMeK
```

```
<220> FEATURE:
<221> NAME/KEY: MISC_FEATURE
<222> LOCATION: (15)..(15)
<223> OTHER INFORMATION: Xaa = D-Pro

<400> SEQUENCE: 127

Tyr Arg Xaa Cys Arg Gly Xaa Arg Arg Xaa Cys Tyr Xaa Xaa Xaa Pro
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 128

Tyr Arg Xaa Cys Arg Gly Xaa Arg Arg Trp Cys Tyr Xaa Lys Xaa Pro
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = NMeGly
<220> FEATURE:
<221> NAME/KEY: MISC_FEATURE
<222> LOCATION: (15)..(15)
<223> OTHER INFORMATION: Xaa = D-Pro

<400> SEQUENCE: 129

Tyr Arg Xaa Cys Arg Gly Xaa Arg Arg Xaa Cys Tyr Xaa Lys Xaa Pro
1               5                   10                  15
```

```
<210> SEQ ID NO 130
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 130

Tyr Arg Gln Cys Arg Gly Xaa Arg Arg Xaa Cys Tyr Xaa Lys Xaa Pro
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 131

Tyr Arg Thr Cys Arg Gly Xaa Arg Arg Xaa Cys Tyr Xaa Lys Xaa Pro
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
```

```
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 132

Tyr Arg Xaa Cys Arg Gly Xaa Arg Arg Xaa Cys Tyr Thr Lys Xaa Pro
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 133

Tyr Arg Xaa Cys Arg Gly Xaa Arg Arg Xaa Cys Tyr Thr Lys Xaa Pro
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = Dab
<220> FEATURE:
<221> NAME/KEY: MISC_FEATURE
```

```
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 134

Tyr Arg Xaa Cys Arg Gly Xaa Xaa Arg Xaa Cys Tyr Xaa Lys Xaa Pro
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = Dab
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 135

Tyr Arg Xaa Cys Arg Gly Xaa Xaa Arg Xaa Cys Tyr Xaa Lys Xaa Pro
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
```

-continued

```
<223> OTHER INFORMATION: Xaa = Cit
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 136

Tyr Arg Xaa Cys Arg Gly Xaa Xaa Arg Trp Cys Tyr Xaa Lys Xaa Pro
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 137

Tyr Arg Xaa Cys Arg Gly Xaa His Arg Trp Cys Tyr Xaa Lys Xaa Pro
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (5)..(5)
<223> OTHER INFORMATION: Xaa = (EA)G
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
```

```
<220> FEATURE:
<221> NAME/KEY: MISC_FEATURE
<222> LOCATION: (15)..(15)
<223> OTHER INFORMATION: Xaa = D-Pro

<400> SEQUENCE: 138

Tyr Arg Xaa Cys Xaa Gly Xaa Arg Arg Xaa Cys Tyr Xaa Lys Xaa Pro
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (9)..(9)
<223> OTHER INFORMATION: Xaa = (EA)G
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 139

Tyr Arg Xaa Cys Arg Gly Pro Arg Xaa Xaa Cys Tyr Xaa Lys Xaa Pro
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro
```

-continued

<400> SEQUENCE: 140

Tyr Arg Xaa Cys Arg Gly Xaa Arg Arg Xaa Cys Tyr Xaa Lys Xaa Pro
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 141

Tyr Arg Xaa Cys Arg Gly Xaa Arg Arg Xaa Cys Tyr Xaa Lys Xaa Pro
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (8)..(8)
<223> OTHER INFORMATION: Xaa = IPegDab
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 142

Tyr Arg Xaa Cys Arg Gly Xaa Xaa Arg Trp Cys Tyr Xaa Lys Xaa Pro
1               5                   10                  15

```
<210> SEQ ID NO 143
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 143

Tyr Arg Xaa Cys Arg Ala Xaa Arg Arg Trp Cys Tyr Xaa Lys Xaa Pro
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (10)..(10)
<223> OTHER INFORMATION: Xaa = 2-Nal
<220> FEATURE:
<221> NAME/KEY: MISC_FEATURE
<222> LOCATION: (15)..(15)
<223> OTHER INFORMATION: Xaa = D-Pro

<400> SEQUENCE: 144

Leu Arg Xaa Cys Arg Gly Xaa Arg Arg Xaa Cys Tyr Gln Lys Xaa Pro
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
```

```
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 145

Tyr Arg Thr Cys Arg Gly Xaa Arg Arg Tyr Cys Tyr Gln Lys Xaa Pro
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 146

Tyr Arg Thr Cys Arg Gly Xaa Arg Arg Tyr Cys Tyr Xaa Lys Xaa Pro
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 147

Tyr Arg Ile Cys Arg Gly Xaa Arg Arg Tyr Cys Tyr Gln Lys Xaa Pro
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
```

```
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Pro

<400> SEQUENCE: 148

Tyr Arg Tyr Cys Arg Gly Xaa Arg Arg Tyr Cys Tyr Gln Lys Xaa Pro
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: DISULFID
<222> LOCATION: (4)..(11)
<223> OTHER INFORMATION: Cys in pos. 4 and 11 form a disulfide bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (15)..(15)
<223> OTHER INFORMATION: Xaa = D-Gln

<400> SEQUENCE: 149

Tyr Arg Xaa Cys Arg Gly Xaa Arg Arg Tyr Cys Tyr Gln Lys Xaa Pro
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (1)..(1)
<223> OTHER INFORMATION: Xaa = Pip
<220> FEATURE:
<221> NAME/KEY: DISULFID
<222> LOCATION: (4)..(13)
<223> OTHER INFORMATION: Cys in pos. 4 and 13 form a disulfide bridge.
<220> FEATURE:
<221> NAME/KEY: MISC_FEATURE
<222> LOCATION: (8)..(8)
<223> OTHER INFORMATION: Xaa = D-Pro
<220> FEATURE:
<221> NAME/KEY: MISC_FEATURE
<222> LOCATION: (12)..(12)
<223> OTHER INFORMATION: Xaa = Cit
<220> FEATURE:
<221> NAME/KEY: MISC_FEATURE
<222> LOCATION: (16)..(16)
<223> OTHER INFORMATION: Xaa = D-Pro

<400> SEQUENCE: 150

Xaa Arg Tyr Cys Tyr Gln Lys Xaa Pro Tyr Arg Xaa Cys Arg Gly Xaa
1               5                   10                  15

<210> SEQ ID NO 151
<211> LENGTH: 16
<212> TYPE: PRT
<213> ORGANISM: Artificial Sequence
```

```
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 151

Tyr Arg Xaa Ser Arg Gly Xaa Arg Arg Trp Asn Tyr Xaa Lys Xaa Pro
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (4)..(4)
<223> OTHER INFORMATION: Xaa = Dab
<220> FEATURE:
<221> NAME/KEY: MISC_FEATURE
<222> LOCATION: (4)..(11)
<223> OTHER INFORMATION: Dab in pos. 4 and Glu in position 11 form a
      lactame bridge.
<220> FEATURE:
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 152

Tyr Arg Xaa Xaa Arg Gly Xaa Arg Arg Trp Glu Tyr Xaa Lys Xaa Pro
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = Cit
<220> FEATURE:
<221> NAME/KEY: MISC_FEATURE
<222> LOCATION: (4)..(11)
<223> OTHER INFORMATION: Glu in pos. 4 and Dab in position 11 form a
      lactame bridge.
<220> FEATURE:
```

```
<221> NAME/KEY: MISC_FEATURE
<222> LOCATION: (7)..(7)
<223> OTHER INFORMATION: Xaa = D-Pro
<220> FEATURE:
<221> NAME/KEY: MISC_FEATURE
<222> LOCATION: (11)..(11)
<223> OTHER INFORMATION: Xaa = Dab
<220> FEATURE:
<221> NAME/KEY: MISC_FEATURE
<222> LOCATION: (13)..(13)
<223> OTHER INFORMATION: Xaa = Cit
<220> FEATURE:
<221> NAME/KEY: MISC_FEATURE
<222> LOCATION: (15)..(15)
<223> OTHER INFORMATION: Xaa = D-Pro

<400> SEQUENCE: 153

Tyr Arg Xaa Glu Arg Gly Xaa Arg Arg Trp Xaa Tyr Xaa Lys Xaa Pro
1               5                   10                  15

<210> SEQ ID NO 154
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: MISC_FEATURE
<222> LOCATION: (3)..(3)
<223> OTHER INFORMATION: Xaa = 2-Nal
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: MISC_FEATURE
<222> LOCATION: (6)..(6)
<223> OTHER INFORMATION: Xaa = Cit
<220> FEATURE:
<221> NAME/KEY: DISULFID
<222> LOCATION: (8)..(13)
<223> OTHER INFORMATION: Cys in pos. 8 and 13 form a disulfide bridge.
<220> FEATURE:
<221> NAME/KEY: MISC_FEATURE
<222> LOCATION: (16)..(16)
<223> OTHER INFORMATION: Xaa = Cit
<220> FEATURE:
<221> NAME/KEY: MISC_FEATURE
<222> LOCATION: (20)..(20)
<223> OTHER INFORMATION: Xaa = D-Pro

<400> SEQUENCE: 154

Arg Arg Xaa Cys Tyr Xaa Lys Cys Tyr Lys Gly Tyr Cys Tyr Arg Xaa
1               5                   10                  15

Cys Arg Gly Xaa
            20

<210> SEQ ID NO 155
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: DISULFID
<222> LOCATION: (8)..(13)
<223> OTHER INFORMATION: Cys in pos. 8 and 13 form a disulfide bridge.
<220> FEATURE:
<221> NAME/KEY: MISC_FEATURE
<222> LOCATION: (16)..(16)
```

```
<223> OTHER INFORMATION: Xaa = Cit
<220> FEATURE:
<221> NAME/KEY: MISC_FEATURE
<222> LOCATION: (20)..(20)
<223> OTHER INFORMATION: Xaa = D-Pro

<400> SEQUENCE: 155

Arg Arg Trp Cys Tyr Gln Lys Cys Tyr Lys Gly Tyr Cys Tyr Arg Xaa
1               5                   10                  15

Cys Arg Gly Xaa
            20

<210> SEQ ID NO 156
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: MISC_FEATURE
<222> LOCATION: (16)..(16)
<223> OTHER INFORMATION: Xaa = Cit
<220> FEATURE:
<221> NAME/KEY: MISC_FEATURE
<222> LOCATION: (20)..(20)
<223> OTHER INFORMATION: Xaa = D-Pro

<400> SEQUENCE: 156

Arg Arg Trp Cys Tyr Gln Lys Gly Tyr Lys Gly Tyr Gly Tyr Arg Xaa
1               5                   10                  15

Cys Arg Gly Xaa
            20

<210> SEQ ID NO 157
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: MISC_FEATURE
<222> LOCATION: (10)..(10)
<223> OTHER INFORMATION: Xaa = D-Lys
<220> FEATURE:
<221> NAME/KEY: MISC_FEATURE
<222> LOCATION: (16)..(16)
<223> OTHER INFORMATION: Xaa = Cit
<220> FEATURE:
<221> NAME/KEY: MISC_FEATURE
<222> LOCATION: (20)..(20)
<223> OTHER INFORMATION: Xaa = D-Pro

<400> SEQUENCE: 157

Arg Arg Trp Cys Tyr Gln Lys Gly Tyr Xaa Gly Tyr Gly Tyr Arg Xaa
1               5                   10                  15

Cys Arg Gly Xaa
            20

<210> SEQ ID NO 158
<211> LENGTH: 20
```

```
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: MISC_FEATURE
<222> LOCATION: (10)..(10)
<223> OTHER INFORMATION: Xaa = D-Pro
<220> FEATURE:
<221> NAME/KEY: MISC_FEATURE
<222> LOCATION: (16)..(16)
<223> OTHER INFORMATION: Xaa = Cit

<400> SEQUENCE: 158

Arg Arg Trp Cys Tyr Gln Lys Gly Tyr Xaa Pro Tyr Gly Tyr Arg Xaa
1               5                   10                  15

Cys Arg Gly Pro
        20

<210> SEQ ID NO 159
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: MISC_FEATURE
<222> LOCATION: (10)..(10)
<223> OTHER INFORMATION: Xaa = D-Pro

<400> SEQUENCE: 159

Arg Arg Tyr Cys Tyr Gln Lys Gly Tyr Xaa Pro Tyr Gly Tyr Arg Thr
1               5                   10                  15

Cys Arg Gly Pro
        20

<210> SEQ ID NO 160
<211> LENGTH: 20
<212> TYPE: PRT
<213> ORGANISM: Artificial Sequence
<220> FEATURE:
<223> OTHER INFORMATION: Cyclic template fixed peptidomimetic
<220> FEATURE:
<221> NAME/KEY: DISULFID
<222> LOCATION: (4)..(17)
<223> OTHER INFORMATION: Cys in pos. 4 and 17 form a disulfide bridge.
<220> FEATURE:
<221> NAME/KEY: DISULFID
<222> LOCATION: (8)..(13)
<223> OTHER INFORMATION: Cys in pos. 8 and 13 form a disulfide bridge.
<220> FEATURE:
<221> NAME/KEY: MISC_FEATURE
<222> LOCATION: (20)..(20)
<223> OTHER INFORMATION: Xaa = D-Pro

<400> SEQUENCE: 160

Arg Arg Trp Cys Tyr Arg Lys Cys Tyr Lys Gly Tyr Cys Tyr Arg Lys
1               5                   10                  15

Cys Arg Gly Xaa
        20
```

TEMPLATE-FIXED BETA-HAIRPIN PEPTIDOMIMETICS WITH CXCR4 ANTAGONIZING ACTIVITY

CROSS-REFERENCE TO RELATED APPLICATIONS

The present application is a continuation application of U.S. application Ser. No. 12/828,998 which is a divisional application of U.S. application Ser. No. 10/555,088, issued as U.S. Pat. No. 7,786,078 filed on Oct. 31, 2005 and afforded a §371 date of Dec. 16, 2005, which U.S. application Ser. No. 10/555,088 is the National Stage filing in the U.S. of International Application No. PCT/EP2004/004535, filed Apr. 29, 2004, which claims priority to PCT/EP03/04640, filed May 2, 2003, the entire contents of all which are incorporated by reference herein.

FIELD OF THE INVENTION

The present invention provides template-fixed βhairpin peptidomimetics incorporating template-fixed chains of 12, 14 or 18 α-amino acid residues which, depending on their positions in the chains, are Gly, NMeGly, Pro or Pip, or of certain types, as defined hereinbelow. These template-fixed β-hairpin mimetics have CXCR4 antagonizing activity. In addition, the present invention provides an efficient synthetic process by which these compounds can, if desired, be made in parallel library-format. These β-hairpin peptidomimetics show improved efficacy, bioavailability, half-life and most importantly a significantly enhanced ratio between CXCR4 antagonizing activity on the one hand, and hemolysis on red blood cells and cytotoxicity on the other.

BACKGROUND OF THE INVENTION

To date the available therapies for the treatment of HIV infections have been leading to a remarkable improvement in symptoms and recovery from disease in infected people. Although the highly active anti retroviral therapy (HAART-therapy) which involves a combination of reverse transcriptase/protease inhibitor has dramatically improved the clinical treatment of individuals with AIDS or HIV infection there have still remained several serious problems including multi drug resistance, significant adverse effects and high costs. Particularly desired are anti HIV agents that block the HIV infection at an early stage of the infection, such as the viral entry.

It has recently been recognized that for efficient entry into target cells, human immunodeficiency viruses require the chemokine receptors CCR5 and CXCR4 as well as the primary receptor CD4 (N. Levy, *Engl. J. Med.*, 335, 29, 1528-1530). Accordingly, an agent which could block the CXCR4 chemokine receptors should prevent infections in healthy individuals and slow or halt viral progression in infected patients (*Science*, 1997, 275, 1261-1264).

Among the different types of CXCR4 inhibitors (M. Schwarz, T. N. C. Wells, A. E. I. Proudfoot, *Receptors and Channels*, 2001, 7, 417-428), one emerging class is based on naturally occurring cationic peptide analogues derived from Polyphemusin II which have an antiparallel 3-sheet structure, and a β-hairpin that is maintained by two disulfide bridges (H. Nakashima, M. Masuda, T. Murakami, Y. Koyanagi, A. Matsumoto, N. Fujii, N. Yamamoto, *Antimicrobial Agents and Chemoth.* 1992, 36, 1249-1255; H. Tamamura, M. Kuroda, M. Masuda, A. Otaka, S. Funakoshi, H. Nakashima, N. Yamamoto, M. Waki, A. Matsumotu, J. M. Lancelin, D. Kohda, S. Tate, F. Inagaki, N. Fujii, *Biochim. Biophys. Acta* 1993, 209, 1163; WO 95/10534 A1).

Synthesis of structural analogs and structural studies by nuclear magnetic resonance (NMR) spectroscopy have shown that the cationic peptides adopt well defined β-hairpins conformations, due to the constraining effect of the one or two disulfide bridges (H. Tamamura, M. Sugioka, Y. Odagaki, A. Omagari, Y. Kahn, S. Oishi, H. Nakashima, N. Yamamoto, S. C. Peiper, N. Hamanaka, A. Otaka, N. Fujii, *Bioorg. Med. Chem. Lett.* 2001, 359-362). These results show that the β-hairpin structure plays an important role in CXCR4 antagonizing activity.

Additional structural studies have also indicated that the antagonizing activity can also be influenced by modulating amphiphilic structure and the pharmacophore (H. Tamamura, A. Omagari, K. Hiramatsu, K. Gotoh, T. Kanamoto, Y. Xu, E. Kodama, M. Matsuoka, T. Hattori, N. Yamamoto, H. Nakashima, A. Otaka, N. Fujii, *Bioorg. Med. Chem. Lett.* 2001, 11, 1897-1902; H. Tamamura, A. Omagari, K. Hiramatsu, S. Oishi, H. Habashita, T. Kanamoto, K. Gotoh, N. Yamamoto, H. Nakashima, A. Otaka N. Fujii, *Bioorg. Med. Chem.* 2002, 10, 1417-1426; H. Tamamura, K. Hiramatsu, K. Miyamoto, A. Omagari, S. Oishi, H. Nakashima, N. Yamamoto, Y. Kuroda, T. Nakagawa, A. Otaki, N. Fujii, *Bioorg. Med. Chem. Letters* 2002, 12, 923-928).

A key issue in the design of CXCR4 antagonizing peptides is selectivity. The polyphemusin II derived analogs exert still a cytotoxicity despite improvements (K. Matsuzaki, M. Fukui, N. Fujii, K. Miyajima, *Biochim. Biophys. Acta* 1991, 259, 1070; A. Otaka, H. Tamamura, Y. Terakawa, M. Masuda, T. Koide, T. Murakami, H. Nakashima, K. Matsuzaki, K. Miyajima, T. Ibuka, M. Waki, A. Matsumoto, N. Yamamoto, N. Fujii *Biol. Pharm. Bull.* 1994, 17, 1669 and cited references above).

This cytotoxic activity essentially obviates its use in vivo, and represents a serious disadvantage in clinical applications. Before intravenous use can be considered, the general toxicity, protein-binding activity in blood serum, as well as protease stability become serious issues which must be adequately addressed.

Recently, it has been shown that the CXCR4-receptor is not only involved in the entry of HIV but also in the chemotactic activity of cancer cells, such as breast cancer metastasis or in metastasis of ovarian cancer (A. Muller, B. Homey, H. Soto, N. Ge, D. Catron, M. E. Buchanan, T. Mc Clanahan, E. Murphey, W. Yuan, S. N. Wagner, J. Luis Barrera, A. Mohar, E. Verastegui, A. Zlotnik, *Nature* 2001, 50, 410, J. M. Hall, K. S. Korach, Molecular Endocrinology, 2003, 1-47), Non-Hodgin's Lymphoma (F. Bertolini, C. DellAgnola, P. Manusco, C. Rabascio, A. Burlini, S. Monestiroli, A. Gobbi, G. Pruneri, G. Martinelli, *Cancer Research* 2002, 62, 3106-3112), or lung cancer (T. Kijima, G. Maulik, P. C. Ma, E. V. Tibaldi, R: E. Turner, B. Rollins, M. Sattler, B. E. Johnson, R. Salgia, *Cancer Research* 2002, 62, 6304-6311), melanoma, prostate cancer, kidney cancer, neuroblastomia, pancreatic cancer, multiple myeloma, chronic lymphocytic leukemia (H. Tamamura et al. *Febs Letters* 2003, 550 79-83, cited ref.) Blocking the chemotactic activity with a CXCR4 inhibitor should stop the migration of cancer cells.

The CXCR4 receptor has also been implicated in the growth and proliferation of tumors. It was shown that activation of the CXCR4 receptor was critical for the growth of both malignant neuronal and glial tumors, and small cell lung tumors. Moreover, systemic administration of the CXCR4 antagonist AMD3100 inhibits growth of intracranial glioblastoma and medulloblastoma xenografts by increasing apoptosis and decreasing the proliferation of tumor cells (Rubin J B, Kung A L, Klein R S, Chan J A, Sun Y, Schmidt K, Kieran M W, Luster A D, Segal R A. *Proc Natl Acad Sci USA.* 2003 100(23):13513-13518, Barbero S, Bonavia R, Bajetto A, Porcile C, Pirani P, Ravetti J L, Zona C L, Spaziante R, Florio T, Schettini G. Stromal *Cancer Res.* 2003, 63(8):1969-1974, Kijima T, Maulik G, Ma P C, Tibaldi E V, Turner R E, Rollins B, Sattler M, Johnson B E, Salgia R. *Cancer Res.* 2002; 62(21):6304-631 1, *Cancer Res.* 2002; 62(11):3106-3112.

The chemokine stromal cell-derived factor-1 (CXCL12/SDF-1) and its receptor CXCR4 are involved in trafficking of B cells and hematopoietic progenitors. It has been shown that the CXCR4 receptor plays an important role in the release of stem cells from the bone marrow to the peripheral blood. The receptor is for instance expressed on CD34+ cells, and has been implicated in the process of CD34+ cell migration and homing. This activity of the CXCR4 receptor could be very important for efficient apheresis collections of peripheral blood stem cell. Autologous peripheral blood cells provide a rapid and sustained hematopoietic recovery following autotransplantation after the administration of high-dose chemotherapy or radiotherapy in patients with haematological malignancies and solid tumors. (W C. Liles et al, *Blood* 2003, 102, 2728-2730).

There is increasing evidence that suggests that chemokines in general and the interaction between the chemoattractant CXCL12/stromal cell-derived factor-I alpha and its receptor CXCR4 in particular play a pivotal role in angiogenesis. Chemokines induce angiogenesis directly by binding their cognate receptors on endothelial cells or indirectly by promoting inflammatory cell infiltrates, which deliver other angiogenic stimuli. A number of proinflammatory chemokines including interleukin 8 (IL-8), growth-regulated oncogene, stromal cell-derived factor 1 (SDF-1), monocyte chemotactic protein 1 (MCP-1), eotaxin 1, and I-309 have been shown to act as direct inducers of angiogenesis. (Chen X, Beutler J A, McCloud T G, Loehfelm A, Yang L, Dong H F, Chertov O Y, Salcedo R, Oppenheim J J, Howard O M. *Clin Cancer Res.* 2003 9(8):3115-3123, Salcedo R, Oppenheim J J. *Microcirculation* 2003 (3-4):359-370)

It is well established that chemokines are involved in a number of inflammatory pathologies and some of them show a pivotal role in the modulation of osteoclast development. Immunostaining for SDF-1 (CXCL12) on synovial and bone tissue biopsies from both rheumatoid arthritis (RA) and osteoarthritis (OA) samples have revealed strong increases in the expression levels under inflammatory conditions. (Grassi F, Cristino S, Toneguzzi S, Piacentini A, Facchini A, Lisignoli G. *J Cell Physiol.* 2004; 199(2):244-251. It seems likely that the CXCR4 receptor plays an important role in inflammatory diseases e.g. such as rheumatoid arthritis, asthma, or multiple sclerose (K. R. Shadidi et al, *Scandinavian Journal of Immunology,* 2003, 57, 192-198, J. A. Gonzalo *J Immunol.* 2000, 165, 499-508, S. Hatse et al, *FEBS Letters* 2002 527, 255-262 and cited references).

The mediation of recruitment of immune cells to sites of inflammation should be stopped by a CXCR4 inhibitor.

In the compounds described below, a new strategy is introduced to stabilize beta-hairpin conformations in cyclic backbone-turn peptidomimetics exhibiting high CXCR4 antagonizing activity, being useful for efficient apheresis collections of peripheral blood stem cells, and having anticancer activity and anti inflammatory activity.

This involves transplanting the cationic and hydrophobic hairpin sequence onto a template, whose function is to restrain the peptide loop backbone into a hairpin geometry. The rigidity of the hairpin may be further influenced by introducing a disulfide bridge. Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), but such molecules have not previously been evaluated for development of CXCR4 antagonizing peptides. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112).

These methods allow the synthesis and screening of large hairpin mimetic libraries, which in turn considerably facilitates structure-activity studies, and hence the discovery of new molecules with highly potent CXCR4 antagonizing activity or anti cancer activity or anti inflammatory activity and low hemolytic activity to human red blood cells. β-Hairpin peptidomimetics obtained by the approach described here are useful as Anti-HIV agents, anticancer agents, as inhibitors of tumor growth or as apoptosis inducing agents, anti-metastasis agents, and anti inflammatory agents or as agents that can be used in apheresis collections of peripheral blood stem cells. The β-hairpin peptidomimetics can be used for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immunosuppression; or during apheresis collections of peripheral blood stem cells. The β-hairpin peptidomimetics can be used for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immunosuppression; or during apheresis collections of peripheral blood stem cells.

SUMMARY OF THE INVENTION

The β-hairpin peptidomimetics of the present invention are compounds of the general formula

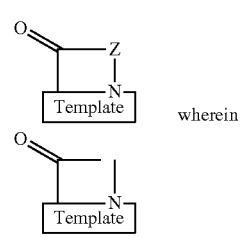

wherein is a group of one of the formulae

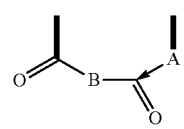

(a1)

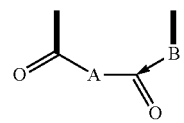

(a2)

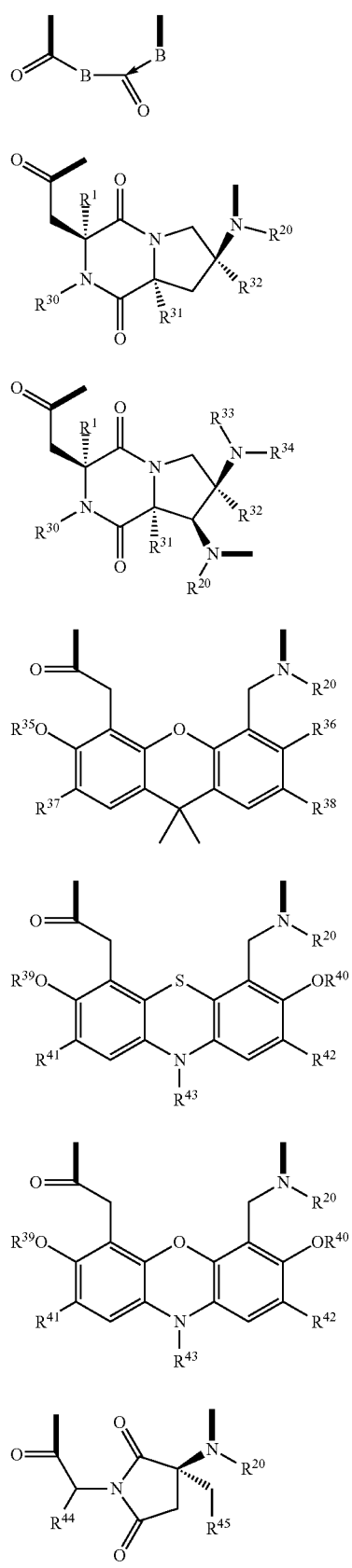
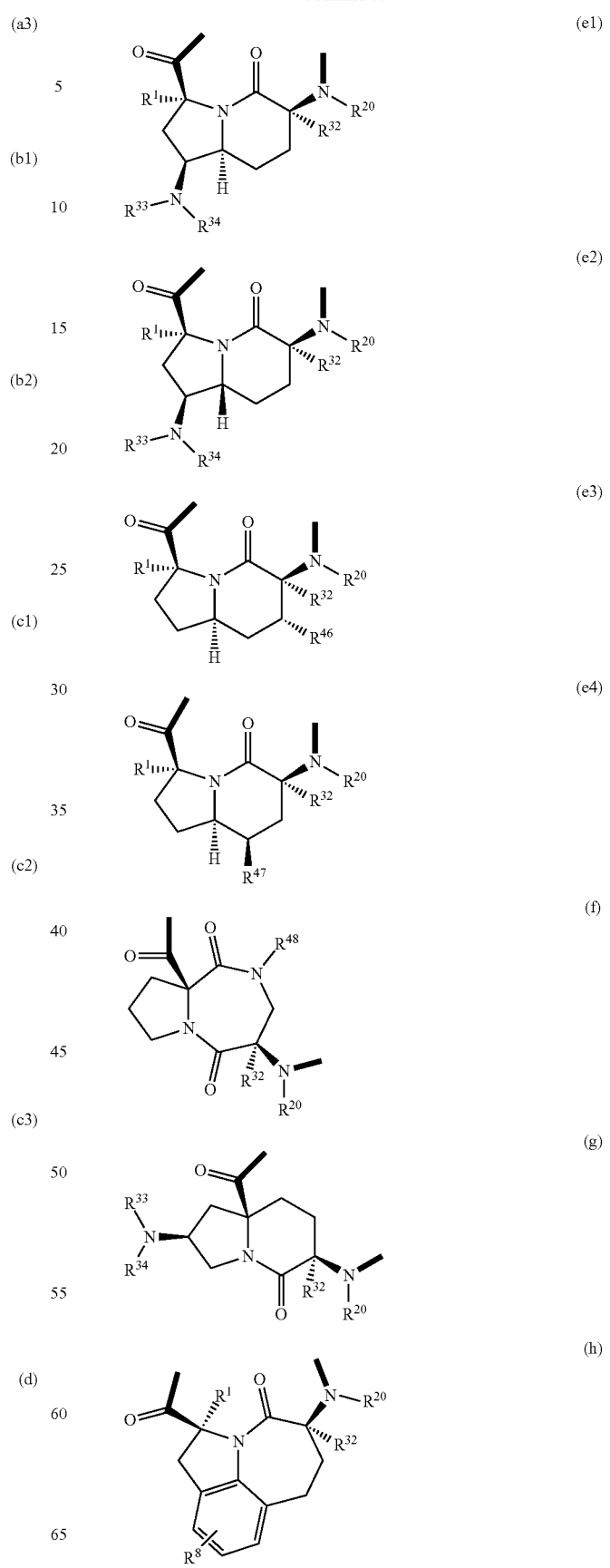

-continued
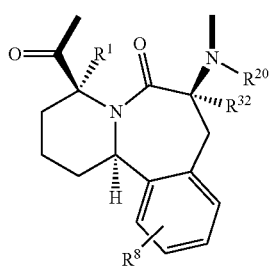
(i1)
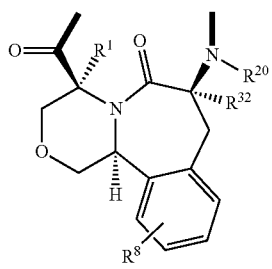
(i2)
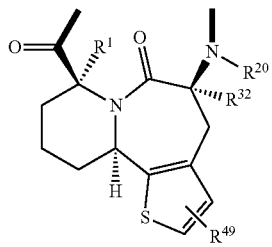
(i3)
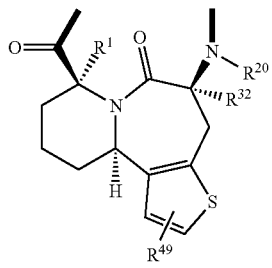
(i4)
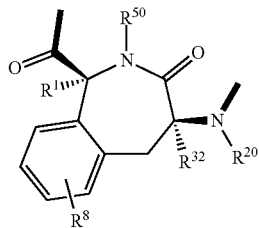
(j)
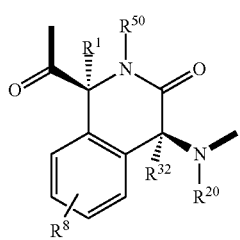
(k)
-continued
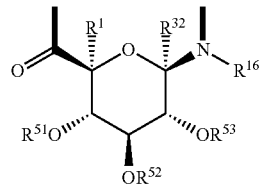
(l)
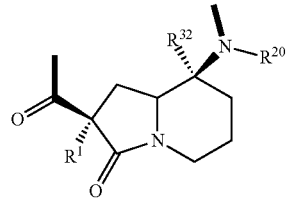
(m)
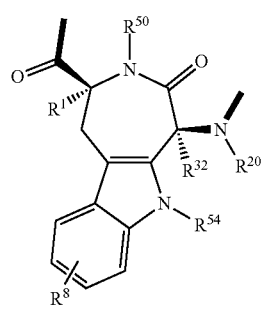
(n)
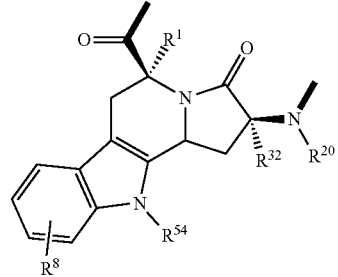
(o)
and
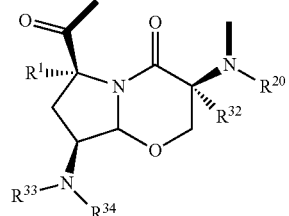
(p)
wherein
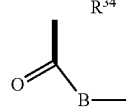
is Gly or the residue of an L-α-amino acid with B being a residue of formula —NR$^{20}$CH(R$^{71}$)— or the enantiomer of one of the groups A1 to A69 as defined hereinafter;

is a group of one of the formulae
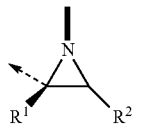 A1
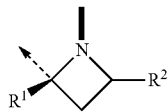 A2
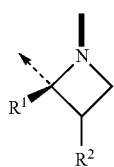 A3
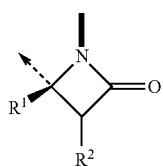 A4
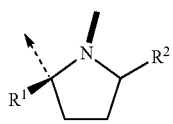 A5
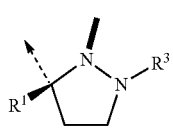 A6
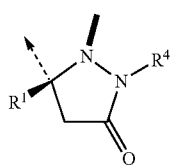 A7
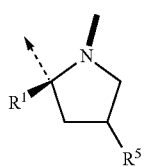 A8
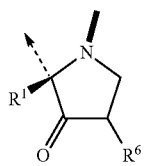 A9
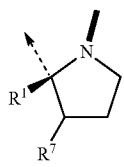 A10
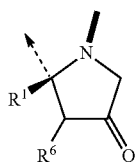 A11
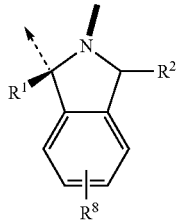 A12
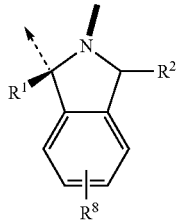 A13
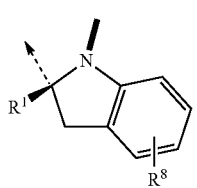 A14
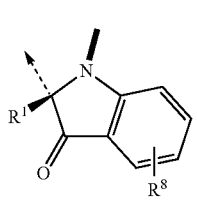 A15
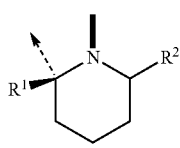 A16
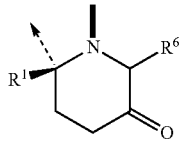 A17
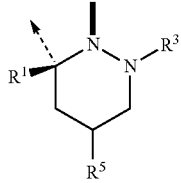 A17
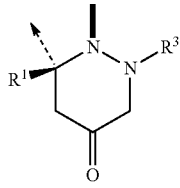 A18

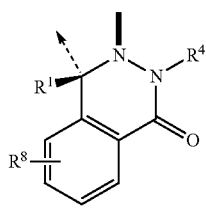
A19
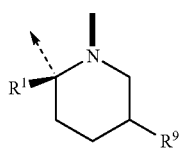
A20
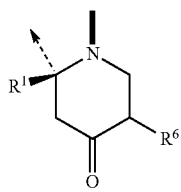
A21
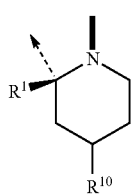
A22
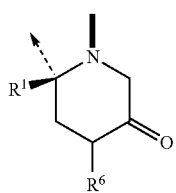
A23
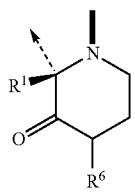
A24
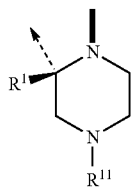
A25
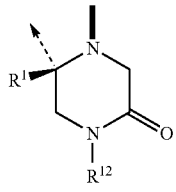
A26
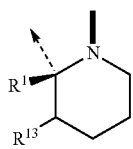
A27
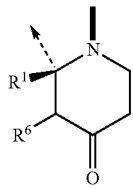
A28
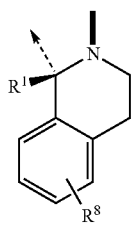
A29
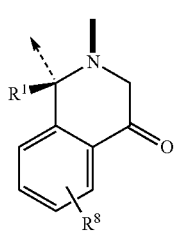
A30
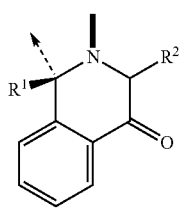
A31
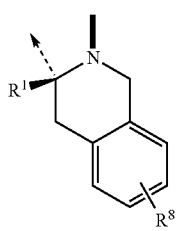
A32
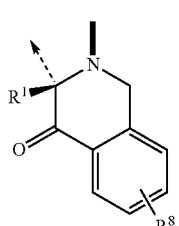
A33
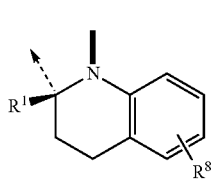
A34

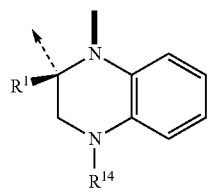 A35
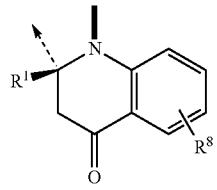 A36
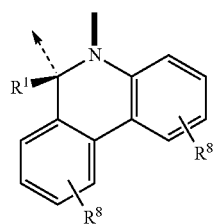 A37
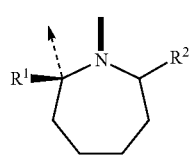 A38
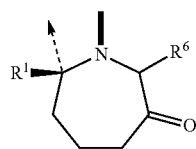 A39
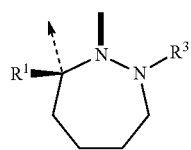 A40
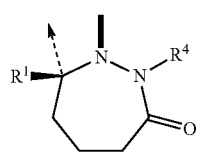 A41
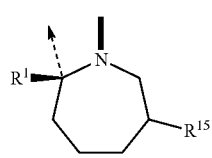 A42
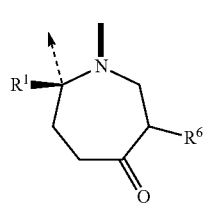 A43
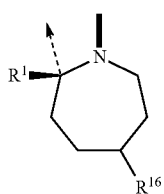 A44
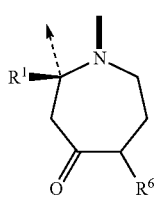 A45
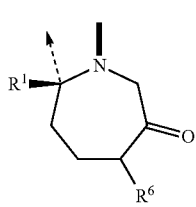 A46
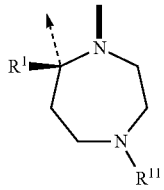 A47
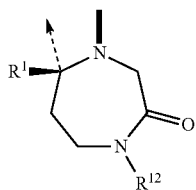 A48
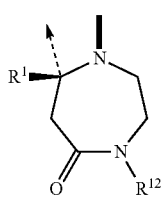 A49
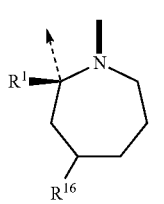 A50
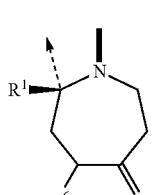 A51

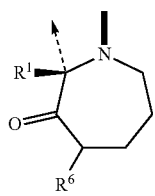 A52
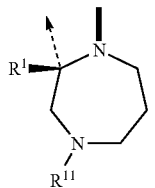 A53
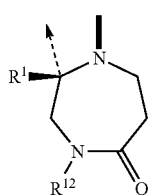 A54
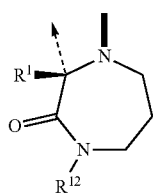 A55
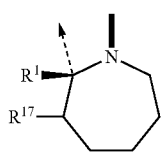 A56
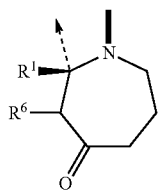 A57
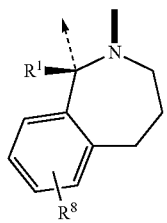 A58
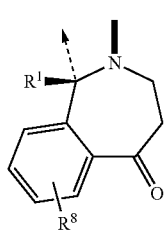 A59
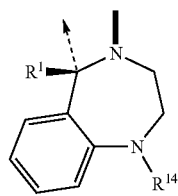 A60
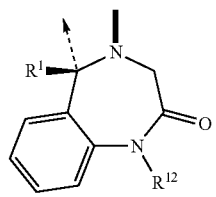 A61
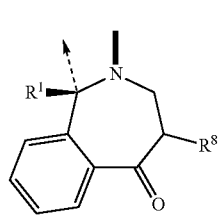 A62
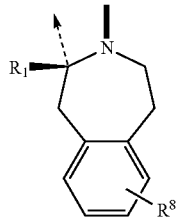 A63
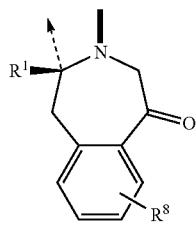 A64
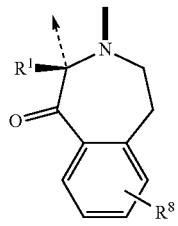 A65
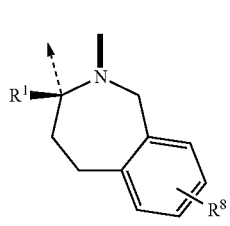 A66

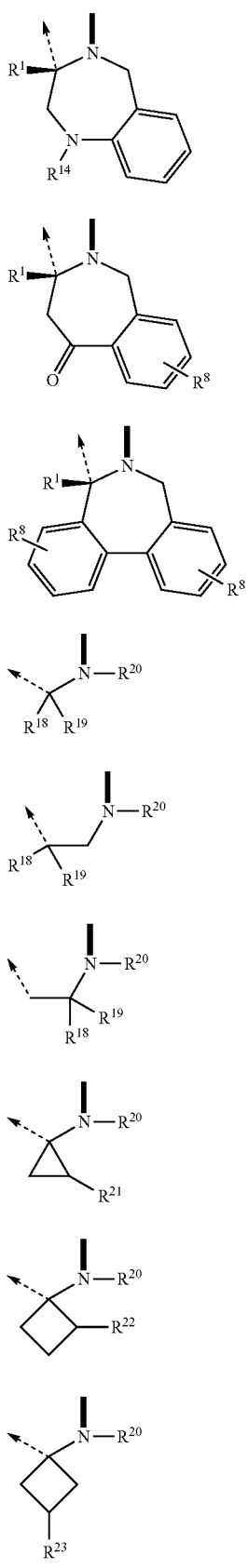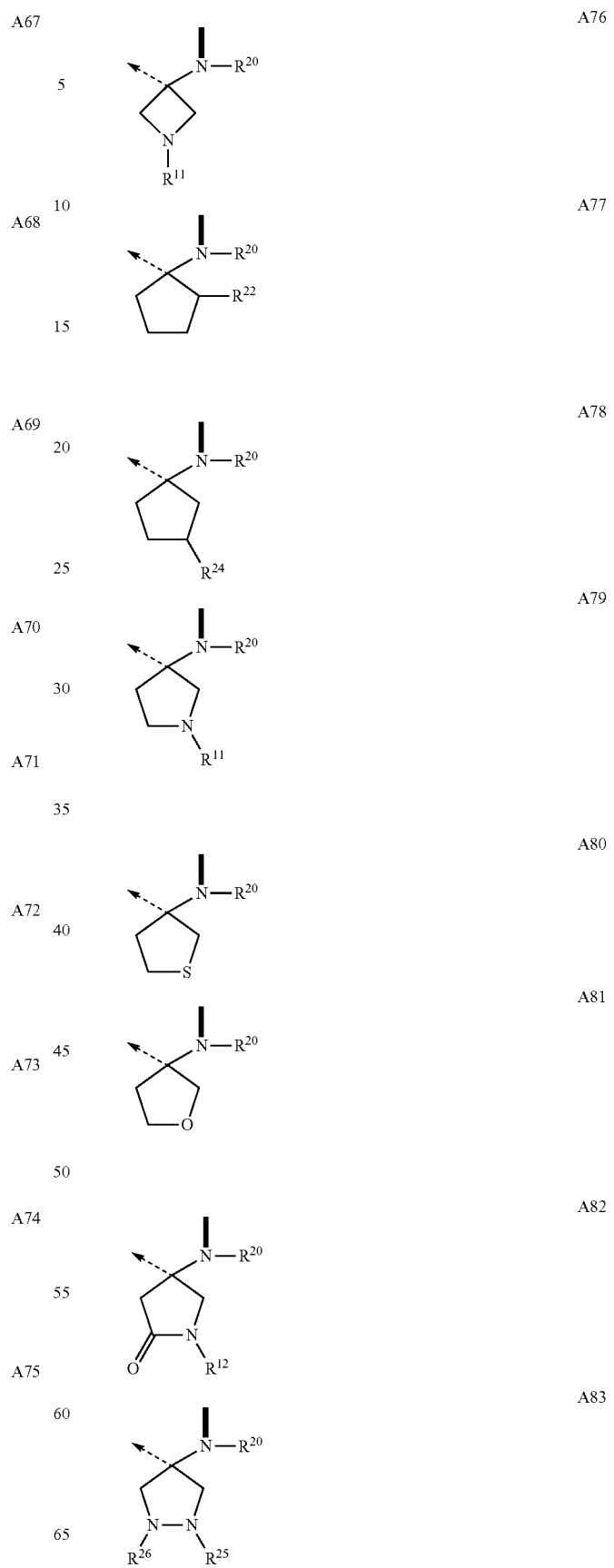

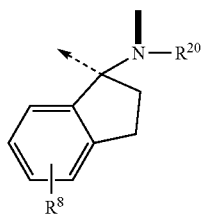 A84
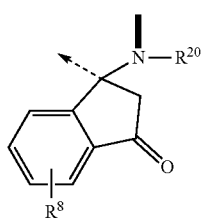 A85
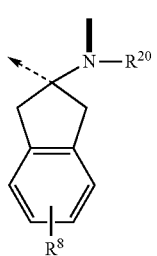 A86
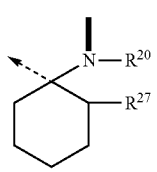 A87
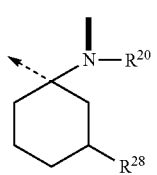 A88
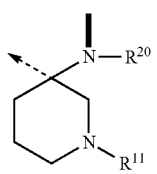 A89
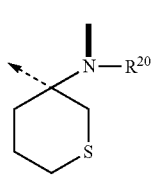 A90
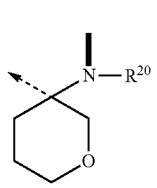 A91
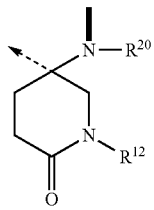 A92
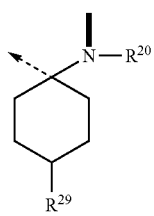 A93
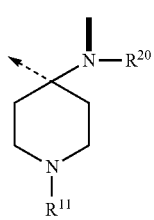 A94
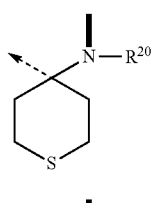 A95
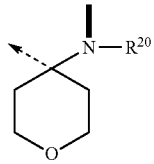 A96
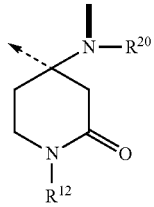 A97
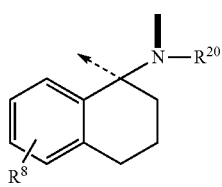 A98
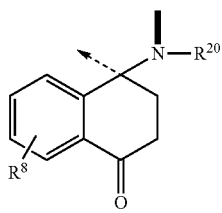 A99

-continued

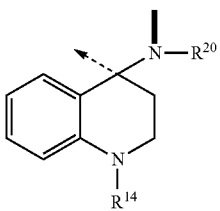
A100

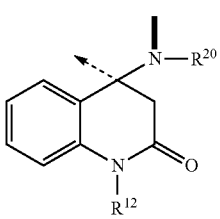
A101

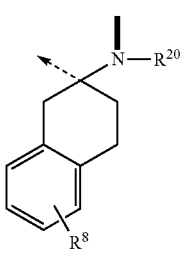
A102

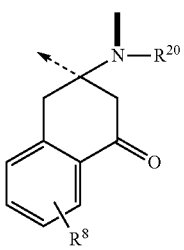
A103 and

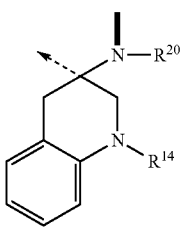
A104

$R^1$ is H; lower alkyl; or aryl-lower alkyl;

$R^2$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})COOR^{57}$; —$(CH_2)_o(CHR^{61})CONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^3$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^4$ is H; alkyl; alkenyl; —$(CH_2)_m(CHR^{61})_sOR^{55}$—; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^7$ is alkyl; alkenyl; —$(CH_2)_q(CHR^{61})_sOR^{55}$; —$(CH_2)_q(CHR^{61})_sNR^{33}R^{34}$; —$(CH_2)_q(CHR^{61})_sOCONR^{33}R^{75}$; —$(CH_2)_q(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_r(CHR^{61})_sC_6H_4R^8$;

$R^8$ is H; Cl; F; $CF_3$; $NO_2$; lower alkyl; lower alkenyl; aryl; aryl-lower alkyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})PO(OR^{60})_2$; —$(CH_2)_o(CHR^{61})_sSO_2R^{62}$; or —$(CH_2)_o(CHR^{61})_sCOR^{64}$;

$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(C_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{10}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})OCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{11}$ is H—; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{12}$ is H; alkyl; alkenyl; —$(CH_2)_m(CHR^{61})_sOR^{55}$; —$(CH_2)_m(CHR^{61})_sSR^{56}$; —$(CH_2(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_r(CHR^{61})_sC_6H_4R^8$;

$R^{13}$ is alkyl; alkenyl; —$(CH_2)_q(CHR^{61})_sOR^{55}$; —$(CH_2)_q(CHR^{61})_sSR^{56}$; —$(CH_2)_q(CHR^{61})_sNR^{33}R^{34}$; —$(CH_2)_q(CHR^{61})_sOCONR^{33}R^{74}$; —$(CH_2)_q(CHR^{61})_sNR^{20}CONR^{33}R^{82}$; —$(CH_2)_q(CHR^{61})_sCOOR^{57}$; —$(CH_2)_q(CHR^{61})_sCONR^{58}R^{59}$; —$(CH_2)_q(CHR^{61})_sPO(OR^{60})_2$; —$(CH_2)_q(CHR^{61})_sSO_2R^{62}$; or —$(CH_2)_q(CHR^{61})_sC_6H_4R^8$;

$R^{14}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_o$ $CONR^{33}R^{75}$; —$(CH_2)_m(CHR^{61})_sNR^{20}CONR^{33}R^{82}$; —$(CH_2)_q(CHR^{61})_sCOOR^{57}$; —$(CH_2)_q(CHR^{61})_s$ $CONR^{58}R^{59}$; —$(CH_2)_q(CHR^{61})_sPO(OR^{60})_2$; —$(CH_2)_q$ $(CHR^{61})_sSOR^2$; or —$(CH_2)_q(CHR^{61})_sC_6H_4R^8$;

$R^{15}$ is alkyl; alkenyl; —$(CH_2)_o(CHR^{61})_sOR^{55}$; —$(CH_2)_o$ $(CHR^{61})_sSR^{56}$; —$(CH_2)_o(CHR^{61})_sNR^{33}R^{34}$; —$(CH_2)_o$ $CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^6$ is alkyl; alkenyl; —$(CH_2)_o(CHR^{61})_sOR^{55}$; —$(CH_2)_o$ $(CHR^{61})_sSR^{56}$; —$(CH_2)_o(CHR^{61})_sNR^{33}R^{34}$; —$(CH_2)_o$ $(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{17}$ is alkyl; alkenyl; —$(CH_2)_q(CHR^{61})OR^{55}$; —$(CH_2)_q$ $(CHR^{61})_sSR^{56}$; —$(CH_2)_q(CHR^{61})_sNR^{33}R^{34}$; —$(CH_2)_q$ $(CHR^{61})_sOCONR^{33}R^{75}$; —$(CH_2)_q(CHR^{61})_s$ $NR^{20}CONR^{33}R^{82}$; —$(CH_2)_q(CHR^{61})_sCOOR^{57}$; —$(CH_2)_q(CHR^{61})_sCONR^{58}R^{59}$; —$(CH_2)_q(CHR^{61})_s$ $PO(OR^{60})_2$; —$(CH_2)_q(CHR^{61})_sSO_2R^{62}$; or —$(CH_2)_q$ $(CHR^{61})_sC_6H_4R^8$;

$R^{18}$ is alkyl; alkenyl; —$(CH_2)_p(CHR^{61})_sOR^{55}$; —$(CH_2)_p$ $(CHR^{61})_sSR^{56}$; —$(CH_2)_p(CHR^{61})_sNR^{33}R^{34}$; —$(CH_2)_p$ $(CHR^{61})_sOCONR^{33}R^{75}$; —$(CH_2)_p(CHR^{61})_s$ $NR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_5$ $PO(OR^{60})_2$; —$(CH_2)_p(CHR^{61})_sSO_2R^{62}$; or —$(CH_2)_p$ $(CHR^{61})_sC_6H_4R^8$;

$R^{19}$ is lower alkyl; —$(CH_2)_p(CHR^{61})_sOR^{55}$; —$(CH_2)_p$ $(CHR^{61})_sSR^{56}$; —$(CH_2)_p(CHR^{61})_sNR^{33}R^{34}$; —$(CH_2)_p$ $(CHR^{61})_sOCONR^{33}R^{75}$; —$(CH_2)_p(CHR^{61})_s$ $NR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_s$ $PO(OR^{60})_2$; —$(CH_2)_p(CHR^{61})_sSO_2R^{62}$; or —$(CH_2)_p$ $(CHR^{61})_sC_6H_4R^8$; or $R^{18}$ and $R^{19}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{20}$ is H; alkyl; alkenyl; or aryl-lower alkyl;

$R^{21}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{22}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{24}$ is alkyl; alkenyl; —$(CH_2)_o(CHR^{61})_sOR^{55}$; —$(CH_2)_o$ $(CHR^{61})_sSR^{56}$; —$(CH_2)_o(CHR^{61})_sNR^{33}R^{34}$; —$(CH_2)_o$ $(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{24}$ is alkyl; alkenyl; —$(CH_2)_o(CHR^{61})_sOR^{55}$; —$(CH_2)_o$ $(CHR^{61})_sSR^{56}$; —$(CH_2)_o(CHR^{61})_sNR^{33}R^{34}$; —$(CH_2)_o$ $(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}SR^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{25}$ is H; alkyl; alkenyl; —$(CH_2)_o(CHR^{61})_sOR^{55}$; —$(CH_2)_m(CHR^{61})_sSR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{26}$ is H; alkyl; alkenyl; —$(CH_2)_m(CHR^{61})SOR^{55}$; —$(CH_2)_m(CHR^{61})SR^{56}$; —$(CH_2)_m(CHR^{61})_rNR^{33}R^{34}$; —$(CH_2)_m(CHR^{61})_sOCoNR^{33}R^{75}$; —$(CH_2)_m(CHR^{61})_s$ $NR^{20}CONR^{33}R^{34}$; —$(CH_2)_m(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$; or $R^{25}$ and $R^{26}$ taken together can form: —$(CH_2)_{2-6}$—; —$(CH_2)_rO(CH_2)_r$—; —$(CH_2)_rS(CH_2)_r$—; or —$(CH_2)_r$ $NR^{57}(CH_2)_r$—;

$R^{27}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_s$ $CONR^{58}R^{59}$; —$(CH_2)_o(CHR^{61})_sOCONR^{33}R^{75}$; —$(CH_2)_o(CHR^{61})_sNR^{20}CONR^{33}R^{82}$; —$(CH_2)_o$ $(CHR^{61})_sPO(OR^{60})_2$; —$(CH_2)_o(CHR^{61})$ $SO_2R^{62}$; or —$(CH_2)_o(CHR^{61})_sC_6H_4R^8$;

$R^{28}$ is alkyl; alkenyl; —$(CH_2)_o(CHR^{61})_s$—$OR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_s$ $NR^{20}CONR^{58}R^{59}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{29}$ is alkyl; alkenyl; —$(CH_2)_o(CHR^{61})_sOR^{55}$; —$(CH_2)_o$ $(CHR^{61})_sSR^{56}$; —$(CH_2)_o(CHR^{61})_sNR^{33}R^{34}$; —$(CH_2)_o$ $(CHR^{61})_sOCONR^{33}R^{75}$; —$(CH_2)_o(CHR^{61})_s$ $NR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_s$ $PO(OR^{60})_2$; —$(CH_2)_o(CHR^{61})_sSO_2R^{62}$; or —$(CH_2)_o$ $(CHR^{61})_sC_6H_4R^8$;

$R^{30}$ is H; alkyl; alkenyl; or aryl-lower alkyl;

$R^{31}$ is H; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_s$ $OCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_s$ $CONR^{58}R^{59}$, —$(CH_2)_o(CHR^{61})_sPO(OR^{60})_2$; —$(CH_2)_o$ $(CHR^{61})_sSO_2R^{62}$; or —$(CH_2)_o(CHR^{61})_sC_6H_4R^8$;

$R^{32}$ is H; lower alkyl; or aryl-lower alkyl;

$R^{33}$ is H; alkyl, alkenyl; —$(CH_2)_m(CHR^{61})_sOR^{55}$; —$(CH_2)_m(CHR^{61})_sNR^{34}R^{63}$; —$(CH_2)_m(CHR^{61})_s$ $OCONR^{75}R^{82}$; —$(CH_2)_m(CHR^{61})_sNR^{20}CONR^{78}R^{82}$; —$(CH_2)_o(CHR^{61})_sCOR^{64}$; —$(CH_2)_o(CHR^{61})_s$— $CONR^{58}R^{59}$, —$(CH_2)_o(CHR^{61})_sPO(OR^{60})_2$; —$(CH_2)_o$ $(CHR^{61})_sSO_2R^{62}$; or —$(CH_2)_o(CHR^{61})_sC_6H_4R^8$;

$R^{34}$ is H; lower alkyl; aryl, or aryl-lower alkyl;

$R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_s$ $OCONR^{33}R^{75}$; —$(CH_2)_m(CHR^{61})_sNR^{20}CONR^{33}R^{82}$; $(CH_2)_p(CHR^{61})_sCOOR^{57}$; —$(CH_2)_p(CHR^{61})_s$ $CONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl, —$(CH_2)_o(CHR^{61})_sOR^{55}$; —$(CH_2)_o(CHR^{61})_sNR^{33}R^{34}$, —$(CH_2)_o(CHR^{61})_sOCONR^{33}R^7$; —$(CH_2)_p(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{37}$ is H; F; Br; Cl; $NO_2$; $CF_3$; lower alkyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{38}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^7$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; —$(CH_2)_p(CHR^{61})_sOR^{55}$; —$(CH_2)_p(CHR^{61})NR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{42}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})NR^{20}CONR^{33}R^{82}$; —$(CH_2)_p(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{43}$ is H; alkyl; alkenyl; —$(CH_2)_m(CHR^{61})OR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})COOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_2SO_2R^{62}$; or —$(CH_2)_o(CHR^{61})_sC_6H_4R^8$;

$R^{44}$ is alkyl; alkenyl; —$(CH_2)_r(CHR^{61})_sOR^{55}$; —$(CH_2)_r(CHR^{61})_sSR^{56}$; —$(CH_2)_r(CHR^{61})_sNR^{33}R^{34}$; —$(CH_2)_r(CHR^{61})_sOCONR^{33}R^{75}$; —$(CH_2)_r(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR)_2$; —$(CH_2)_r(CHR^{61})_sSO_2R^{62}$; or —$(CH_2)_r(CHR^{61})_sC_6H_4R^8$;

$R^{45}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_s(CHR^{61})_sCONR^{58}R^{59}$; —$(CH_2)_s(CHR^{61})_sPO(OR^{60})_2$; —$(CH_2)_s(CHR^{61})_sSO_2R^{62}$; or —$(CH_2)_s(CHR^{61})_sC_6H_4R^8$;

$R^{46}$ is H; alkyl; alkenyl; or —$(CH_2)_o(CHR^{61})_pC_6H_4R^8$;

$R^{47}$ is H; alkyl; alkenyl; or —$(CH_2)_o(CHR^{61})_sOR^{55}$;

$R^{48}$ is H; lower alkyl; lower alkenyl; or aryl-lower alkyl;

$R^{49}$ is H; alkyl; alkenyl; —$(CHR^{61})_sCOOR^{57}$; $(CHR^{61})_sCONR^{58}R^{59}$; $(CHR^{61})_sPO(OR^{60})_2$; $(CHR^{61})_sSOR^{62}$; or $(CHR^{61})_sC_6H_4R^8$;

$R^{50}$ is H; lower alkyl; or aryl-lower alkyl;

$R^{51}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$—$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{52}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{62})_pPO(OR^{60})_2$; —$(CH_2)_p(CHR^{61})_sSO_2R^{62}$; or —$(CH_2)_p(CHR^{61})_sC_6H_4R^8$;

$R^{53}$ is H; alkyl; alkenyl; —$(CH_2)_m(CHR^{61})_sOR^{55}$; —$(CH_2)_m(CHR^{61})SR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{61}$; or —$(CH_2)_p(CHR^{61})_sC_6H_4R^8$;

$R^{54}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})COOR^{57}$; —$(CH_2)_o(CHR^{61})_sCONR^{58}R^{59}$; or —$(CH_2)_o(CHRR^{61})_sC_6H_4R^8$;

$R^{55}$ is H; lower alkyl; lower alkenyl; aryl-lower alkyl; —$(CH_2)_m(CHR^{61})_sOR^{57}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})_s$—$COR^{64}$; —$(CH_2)_o(CHR^{61})COOR^{57}$; or —$(CH_2)_o(CHR^{61})_sCONR^{58}R^{59}$;

$R^{56}$ is H; lower alkyl; lower alkenyl; aryl-lower alkyl; —$(CH_2)_m(CHR^{61})OR^{57}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})_s$—$COR^{64}$; or —$(CH_2)_o(CHR^{61})_sCONR^{58}R^{59}$, $R^{57}$ is H; lower alkyl; lower alkenyl; aryl lower alkyl; or heteroaryl lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; —$(CH_2)_mOR^{55}$; —$(CH_2)_mNR^{33}R^{34}$; —$(CH_2)_mOCONR^{75}R^{82}$; —$(CH_2)_mNR^{20}CONR^{75}R^{82}$; —$(CH_2)_oCOOR^{37}$; —$(CH_2)_oNR^{58}R^{59}$; or —$(CH_2)_oPO(COR^{60})_2$;

$R^{62}$ is lower alkyl; lower alkenyl; aryl, heteroaryl; or aryl-lower alkyl;

$R^{63}$ is H; lower alkyl; lower alkenyl; aryl, heteroaryl; aryl-lower alkyl; heteroaryl-lower alkyl; —$COR^{64}$; —$COOR^{57}$; —$CONR^{58}R^{59}$; —$SO_2R^{62}$; or —$PO(OR^{60})_2$ $R^{34}$ and $R^{63}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{64}$ is H; lower alkyl; lower alkenyl; aryl; heteroaryl; aryl-lower alkyl; heteroaryl-lower alkyl; —$(CH_2)_p(CHR^{61})_sOR^{65}$; —$(CH_2)_p(CHR^{61})_sSR^{66}$; or —$(CH_2)_p(CHR^{61})_sNR^{34}R^{63}$; —$(CH_2)_p(CHR^{61})_sOCONR^{75}R^{82}$; —$(CH_2)_p(CHR^{61})NR^2CONR^{78}R^{82}$;

$R^{65}$ is H; lower alkyl; lower alkenyl; aryl, aryl-lower alkyl; heteroaryl-lower alkyl; —$COR^{17}$; —$COOR^{57}$; or —$CONR^{58}R^{59}$;

$R^{66}$ is H; lower alkyl; lower alkenyl; aryl; aryl-lower alkyl; heteroaryl-lower alkyl; or —$CONR^{58}R^{59}$;

m is 2-4; o is 0-4; p is 1-4; q is 0-2; r is 1 or 2; s is 0 or 1;

Z is a chain of n α-amino acid residues, n being the integer 12, 14 or 18 and the positions of said amino acid residues in said chain being counted starting from the N-terminal amino acid, whereby these amino acid residues are, depending on their position in the chains, Gly, NMeGly, Pro or Pip, or of formula -A-CO—, or of formula —B—CO—, or of one of the types C: —$NR^{20}CH(R^{72})CO$—;
D: —$NR^{20}CH(R^{73})CO$—;
E: —$NR^{20}CH(R^{74})CO$—;
F: —$NR^{20}CH(R^{84})CO$—; and
H: —$NR^{20}$—$CH(CO$—$)$—$(CH_2)_{4-7}$—$CH(CO$—$)$—$NR^{20}$—; —$NR^{20}$—$CH(CO$—$)$—$(CH_2)_p SS(CH_2)_p CH(CO$—$)$—$NR^{20}$—; —$NR^{20}$—$CH(CO$—$)$-$(-(CH_2)_p$ $NR^{20}CO(CH_2)_p$—$CH(CO$—$)$—$NR^{20}$—; and —$NR^{20}$—$CH(CO$—$)$-$(-CH_2)_p NR^{20}CONR^{20}(CH_2)_p$—$CH(CO$—$)$—$NR^{20}$—;

I: —$NR^{86}CH_2CO$—;

$R^{71}$ is lower alkyl; lower alkenyl; —$(CH_2)_p(CHR^{61})_s OR^{75}$; —$(CH_2)_p(CHR^{61})_s SR^{75}$; —$(CH_2)_p(CHR^{61})_s NR^{33}R^{34}$; —$(CH_2)_p(CHR^{61})_s OCONR^{33}R^{75}$; —$(CH_2)_p(CHR^{61})_s N^{20}CONR^{33}R^{82}$; —$(CH_2)_o(CHR^{61})_s COOR^{75}$; —$(CH_2)_p CONR^{58}R^{59}$; —$(CH_2)_p PO(OR^{62})_2$; —$(CH_2)_p SO_2 R^{62}$; or —$(CH_2)_o$—$C_6 R^{67}R^{68}R^{69}R^{70}R^{76}$;

$R^{72}$ is H, lower alkyl; lower alkenyl; —$(CH_2)_p(CHR^{61})_s OR^{85}$; or —$(CH_2)_p(CHR^{61})_s SR^{85}$;

$R^{73}$ is —$(CH_2)_o R^{77}$; —$(CH_2)_r O(CH_2)_o R^{77}$; —$(CH_2)_r S(CH_2)_o R^{77}$; or —$(CH_2)_r NR^{20}(CH_2)_o R^{77}$;

$R^{74}$ is —$(CH_2)_p NR^{78}R^{79}$; —$(CH_2)_p NR^{77}R^{80}$; —$(CH_2)_p C(=NR^{80})NR^{78}R^{79}$; —$(CH_2)_p C(=NOR^{50})NR^{78}R^{79}$; —$(CH_2)_p C(=NNR^{78}R^{79})NR^{78}R^{79}$; —$(CH_2)_p NR^{80}C(=NR^{80})NR^{78}R^{79}$; —$(CH_2)_p N=C(NR^{78}R^{80})NR^{79}R^{80}$; —$(CH_2)_p C_6 H_4 NR^{78}R^{79}$; —$(CH_2)_p C_6 H_4 NR^{77}R^{80}$; —$(CH_2)_p C_6 H_4 C(=NR^{80})NR^{78}R^{79}$; —$(CH_2)_p C_6 H_4 C(=NOR^{50})NR^{78}R^{79}$; —$(CH_2)_p C_6 H_4 C(=NNR^{78}R^{79})NR^{78}R^{79}$; —$(CH_2)_p C_6 H_4 NR^{80}C(=NR^{80})NR^{78}R^{79}$; —$(CH_2)_p C_6 H_4 N=C(NR^{78}R^{80})NR^{79}R^{80}$; —$(CH_2)_r O(CH_2)_m NR^{78}R^{79}$; —$(CH_2)_r O(CH_2)_m NR^{77}R^{80}$; —$(CH_2)_r O(CH_2)_p C(=NR^{80})NR^{78}R^{79}$; —$(CH_2)_r O(CH_2)_p C(=NOR^{50})NR^{78}R^{79}$; —$(CH_2)_r O(CH_2)_p C(=NNR^{78}R^{79})NR^{78}R^{79}$; —$(CH_2)_r O(CH_2)_m NR^{80}C(=NR^{80})NR^{78}R^{79}$; —$(CH_2)_r O(CH_2)_m N=C(NR^{78}R^{80})NR^{79}R^{80}$; —$(CH_2)_r O(CH_2)_p C_6 H_4 CNR^{78}R^{79}$; —$(CH_2)_r O(CH_2)_p C_6 H_4 C(=NR^{80})NR^{78}R^{79}$; —$(CH_2)_r O(CH_2)_p C_6 H_4 C(=NOR^{50})NR^{78}R^{79}$; —$(CH_2)_r O(CH_2)_p C_6 H_4 C(NNR^{78}R^{79})NR^{78}R^{79}$; —$(CH_2)_r O(CH_2)_p C_6 H_4 NR^{80}C(=NR^{80})NR^{78}R^{79}$; —$(CH_2)_r S(CH_2)_m NR^{78}R^{79}$; —$(CH_2)_r S(CH_2)_m NR^{77}R^{80}$; —$(CH_2)_r S(CH_2)_p C(=NR^{80})NR^{78}R^{79}$; —$(CH_2)_r S(CH_2)_p C(=NOR^{50})NR^{78}R^{79}$; —$(CH_2)_r S(CH_2)_p C(=NNR^{78}R^{79})NR^{78}R^{79}$; —$(CH_2)_r S(CH_2)_m NR^{80}C(=NR^{80})NR^{78}R^{79}$; —$(CH_2)_r S(CH_2)_m N=(NR^{78}R^{79})NR^{79}R^{80}$; —$(CH_2)_r S(CH_2)_p C_6 H_4 CNR^{78}R^{79}$; —$(CH_2)_r S(CH_2)_p C_6 H_4 C(=NR^{80})NR^{78}R^{79}$; —$(CH_2)_r S(CH_2)_p C_6 H_4 C(=NOR^{50})NR^{78}R^{79}$; —$(CH_2)_r S(CH_2)_p C_6 H_4 C(=NNR^{78}R^{79})NR^{78}R^{79}$; —$(CH_2)_r S(CH_2)_p C_6 H_4 NR^{80}C(=NR^{80})NR^{78}R^{79}$; —$(CH_2)_p NR^{80}COR^{64}$; —$(CH_2)_p NR^{80}COR^{77}$; —$(CH_2)_p NR^{80}CONR^{78}R^{79}$; —$(CH_2)_p C_6 H_4 NR^{80}CONR^{78}R^{79}$; or —$(CH_2)_p NR^{20}CO$—$[(CH_2)_u$—$X]_t$—$CH_3$ where X is —O—; —$NR^{20}$—, or —S—; u is 1-3, and t is 1-6;

$R^{75}$ is lower alkyl; lower alkenyl; or aryl-lower alkyl;

$R^{33}$ and $R^{75}$ taken together can form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—;

$R^{75}$ and $R^{82}$ taken together can form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—;

$R^{76}$ is H; lower alkyl; lower alkenyl; aryl-lower alkyl; —$(CH_2)_o R^{72}$; —$(CH_2)_o SR^{72}$; —$(CH_2)_o NR^{33}R^{34}$; —$(CH_2)_o OCONR^{33}R^{75}$; —$(CH_2)_o NR^{20}CONR^{33}R^{82}$; —$(CH_2)_o COOR^{75}$, —$(CH_2)_o CONR^{58}R^{59}$; —$(CH_2)_o PO(OR^{60})_2$; —$(CH_2)_p SO_2 R^{62}$; or —$(CH_2)_o COR^{64}$;

$R^{77}$ is —$C_6 R^{67}R^{68}R^{69}R^{70}R^{76}$; or a heteroaryl group of one of the formulae

H1

[structure with O ring and $R^{82}$]

H2

[structure with O ring, methyl, and $R^{82}$]

H3

[structure with S ring and $R^{82}$]

H4

[structure with S ring, methyl, and $R^{82}$]

H5

[structure with N-imidazole ring, $R^{81}$, $R^{82}$]

H6

[structure with imidazole ring, $R^{83}$, $R^{81}$]

H7

[structure with imidazole ring, $R^{83}$, $R^{81}$]

H8

[structure with pyrrole ring, $R^{81}$, $R^{82}$]

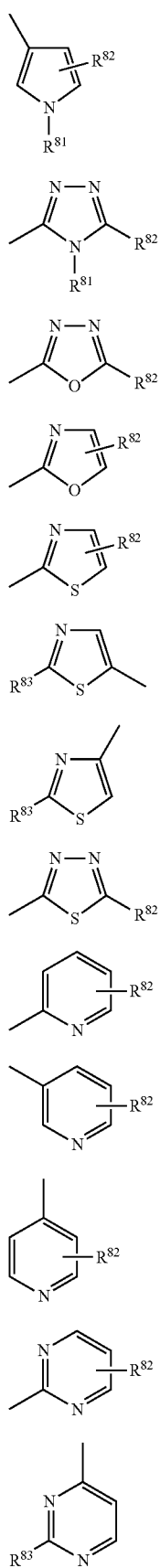
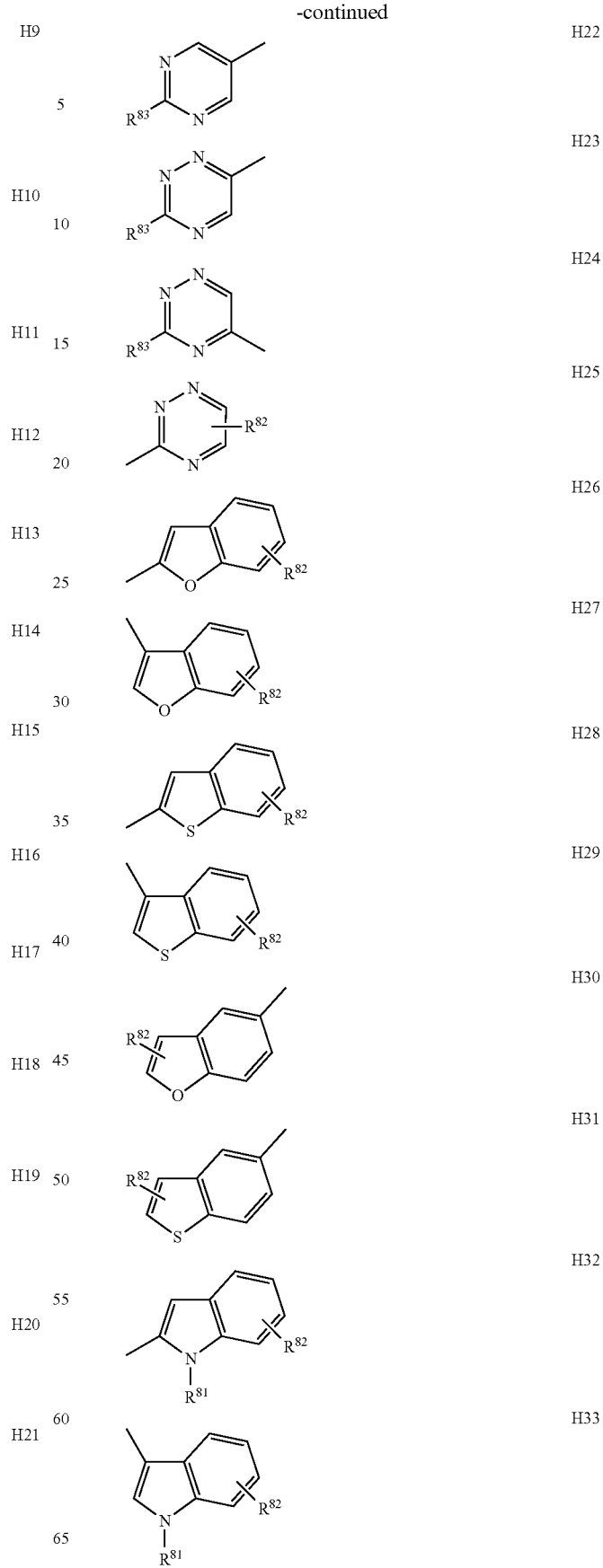

-continued
H34 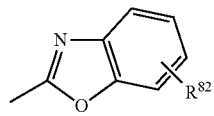
H35 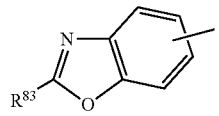
H36 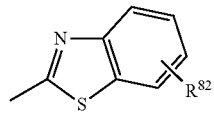
H37 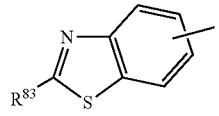
H38 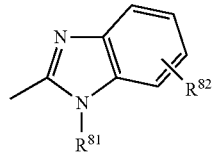
H39 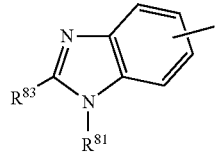
H40 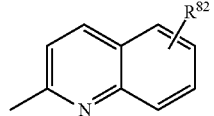
H41 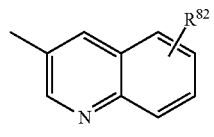
H42 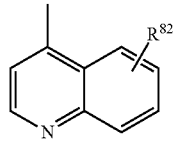
H43 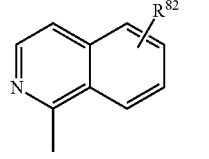
H44 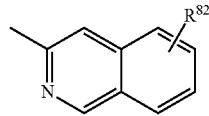
-continued
H45 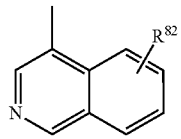
H46 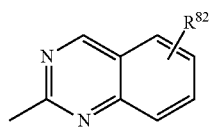
H47 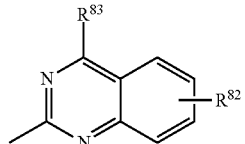
H48 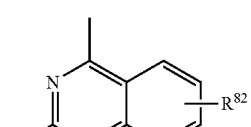
H49 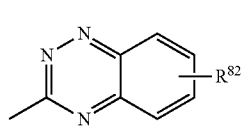
H50 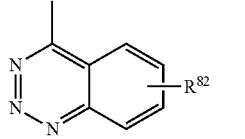
H51 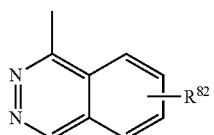
H52 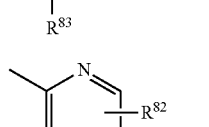
H53 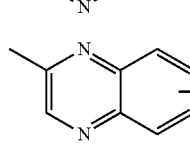
H54 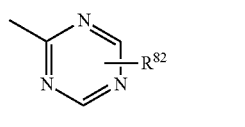
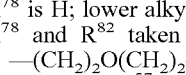
$R^{78}$ is H; lower alkyl; aryl; or aryl-lower alkyl;
$R^{78}$ and $R^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
$R^{79}$ is H; lower alkyl; aryl; or aryl-lower alkyl; or
$R^{78}$ and $R^{79}$, taken together, can be —(CH$_2$)$_{2-7}$—; —(CH$_2$)$_2$O(CH$_2$)$_2$—; or —(CH$_2$)$_2$NR$^{57}$(CH$_2$)$_2$—;
$R^{80}$ is H; or lower alkyl;

$R^{81}$ is H; lower alkyl; or aryl-lower alkyl;

$R^{82}$ is H; lower alkyl; aryl; heteroaryl; or aryl-lower alkyl;

$R^{33}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{83}$ is H; lower alkyl; aryl; or $-NR^{78}R^{79}$;

$R^{84}$ is $-(CH_2)_m(CHR_{61})_sOH$; $-(CH_2)pCOOR_{80}$; $-(CH_2)_m(CHR_{61})_sSH$; $-(CH_2)_pCONR^{78}R^{79}$; $-(CH_2)_pNR^{80}CONR^{78}R^{79}$; $-(CH_2)_p C_6H_4CONR^{78}R^{79}$; or $-(CH_2)_p C_6H_4NR^{80}CONR^{78}R^{79}$;

$R^{85}$ is lower alkyl; or lower alkenyl;

$R^{86}$ is $R^{74}$; $-(CH_2)_oR^{77}$; $-(CH_2)_o-CHR^{33}R^{75}$; or $-[(CH_2)_u-X']_t-(CH_2)_vNR^{78}R^{79}$; or $-[(CH_2)_u-X']_t-(CH_2)_v-(=NR^{80})NR^{78}R^{79}$ where X is $-O-$, $-NR^{20}-$, $-S-$; or $-OCOO-$, u is 1-3, t is 1-6, and v is 1-3;

with the proviso that in said chain of n α-amino acid residues Z if n is 12, the amino acid residues in positions 1 to 12 are:

P1: of type C or of type D or of type E or of type F, or the residue is Pro or Pip;

P2: of type E, or of type F or the residue is Gly, NMeGly, Pro or Pip;

P3; or of type E, of type F;

P4: of type C, or of type D, or of type F, or the residue is Gly or NMeGly;

P5: of type E, or of type D, or of type C, or of type F, or of formula -A-CO— or the residue is Gly. NMeGly, Pro or Pip;

P6: of type E, or of type F, or of formula —B—CO—, or the residue is Gly or NMeGly;

P7: of type C, or of type E or of type F;

P8: of type D, or of type C, or the residue is Pro or Pip;

P9: of type C, or of type D or of type F, or the residue is Gly or NMeGly;

P10: of type D, or of type C, or the residue is Pro or Pip;

P11: of type E or of type F or the residue is Gly or NMeGly; and

P12: of type C or of type D or of type E or of type F, or the residue is Pro or Pip; or P4 and P9 and/or P2 and P11, taken together, can form a group of type H;

at P4, P6. P9 also D-isomers being possible; and if n is 14, the amino acid residues in positions 1 to 14 are:

P1: of type C, or of type D, or of type E, or of type F, or the residue is Gly or NMeGly or Pro or Pip;

P2: of type E, or of type F, or of type I, or of type D;

P3: of type E, or of type F; or of type D, or of type C, or the residue is Gly, NMeGly, Pro Pip;

P4: of type D, or of type C or of type F, or of type E;

P5: of type E, or of type F, or of type C or of type I;

P6: of type C, or of type D, or of type F, or the residue is Gly, NMeGly, Pro or Pip;

P7: of type C, or of type D, or of formula A-CO—, or the residue is Gly, NMeGly. Pro Pip;

P8: of type E, or of Type F, or of formula B—CO— or of type I, or of type D, or the residue is Pro Pip;

P9: of type F, or of type E, or of type I, or of type D, or the residue is Pro or Pip;

P10: of type F, or of type D, or of type C;

P11: of type D, or of type C, or of type F, or of type E, or the residue is Pro or Pip;

P12: of type C, or of type D, or of type E, or of type F;

P13: of type F, or of type E, or the residue is Gly. NMeGly, Pro or Pip; and

P14; or of type F or of type E or of type C; or

P2 and P13 and/or P4 and P11, take together, can form a group of type H;

at P4, P7, P8 and P11 D-isomers being possible;

with the further proviso that the amino acid residue in P1 is Gly or NMeGly or Pip; and/or the amino acid residue in P2 is of type F or of type I; and/or the amino acid residue in P3 is of type F, or it is Gly, NMeGly. Pro or Pip;

and/or the amino acid residue in P4 is of type F; and/or the amino acid residue in P5 is of type C or of type F or of type 1; and/or the amino acid residue in P6 is of type C or of type D, or it is Gly or NMeGly;

and/or the amino acid residue in P7 is of type C or of type D, or it is Pro. Pip or NMeGly; and/or the amino acid residue in P8 is of type I or of type D, or it is Pro or Pip; and/or the amino acid residue in P9 is of type F or of type I, or it is Pip; and/or the amino acid residue in P10 is of type F; and/or the amino acid residue in P11 is of type C, or it is Pip; and/or the amino acid residue in P12 is of type C or of type F; and/or the amino acid residue in P13 is of type F, or it is Gly, NMeGly or Pip; and/or P2 and P13, taken together, form a group of type H; and/or P4 and P11, taken together, form a group of type H; and/or the amino acid residue in P4 is a D-isomer, and/or the amino acid residue in P11 is a D-isomer, and if n is 18, the amino acid residues in positions 1 to 18 are:

P1: of type D, or of type E, or of type C, or of type F;

P2: of type E, or of type F, or of type D;

P3: of type C, or of type D;

P4: of type E, or of type D, or of type F;

P5: of type D, or of type C, or of type E;

P6: of type C, or of type E, or of type F;

P7: of type C, or of type D, or of type E or of type F;

P8: of type F, or of type E, or the residue is Gly or NMeGly;

P9: of type C, or of type D, or of type F;

P10: of type C, or of type E, or of formula -A-CO—, or the residue is Pro or Pip;

P11: of type C, or of type E, or of formula —B—CO—, or the residue is Gly, NMeGly, Pro or Pip;

P12: of type D, or of type C, or type F;

P13: of type E, or of type F, or the residue is Gly or NMeGly;

P14: of type C, or of type D, or of type F;

P15: of type E, or of type F;

P16: of type D, or of type E, or of type F;

P17: of type E, or of type F; and
P18: of type C, or of type D, or of type E, or of type F; or
P4 and P17 and/or P6 and P15 and/or P8 and P13, taken together, can form a group of type H;
at P10, P11 and P12 also D-isomers being possible; and pharmaceutically acceptable salts thereof.

DETAILED DESCRIPTION OF THE INVENTION

In accordance with the present invention these β-hairpin peptidomimetics can be prepared by a process which comprises
  (a) coupling an appropriately functionalized solid support with an appropriately N-protected derivative of that amino acid which in the desired end-product is in position 5, 6 or 7 if n is 12, or which in the desired end-product is in position 6, 7 or 8 if n is 14, or which in the desired end-product is in position 8, 9 or 10 if n is 18, any functional group which may be present in said N-protected amino acid derivative being likewise appropriately protected;
  (b) removing the N-protecting group from the product thus obtained;
  (c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;
  (d) removing the N-protecting group from the product thus obtained;
  (e) repeating steps (c) and (d) until the N-terminal amino acid residue has been introduced;
  (f) coupling the product thus obtained with a compound of the general formula

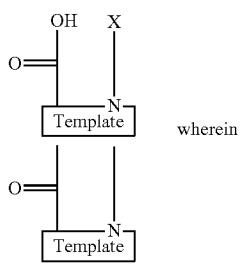

II wherein is as defined above and X is an N-protecting group or, alternatively, if

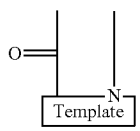

is to be group (a1) or (a2), above,
  (fa) coupling the product obtained in step (e) with an appropriately N-protected derivative of an amino acid of the general formula

HOOC—B—H    III or

HOOC-A-H    IV wherein B and A are as defined above, any functional group which may be present in said N-protected amino acid derivative being likewise appropriately protected;
  (fb) removing the N-protecting group from the product thus obtained; and
  (fc) coupling the product thus obtained with an appropriately N-protected derivative of an amino acid of the above general formula IV and, respectively, III, any functional group which may be present in said N-protected amino acid derivative being likewise appropriately protected; and, respectively, if

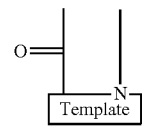

is to be group (a3), above,
  (fa') coupling the product obtained in step (e) with an appropriately N-protected derivative of an amino acid of the above general formula III, any functional group which may be present in said N-protected amino acid derivative being likewise appropriately protected;
  (fb') removing the N-protecting group from the product thus obtained; and
  (fc') coupling the product thus obtained with an appropriately N-protected derivative of an amino acid of the above general formula III, any functional group which may be present in said N-protected amino acid derivative being likewise appropriately protected;
  (g) removing the N-protecting group from the product obtained in step (f) or (fc) or (fc');
  (h) coupling the product thus obtained with an appropriately N-protected derivative of that amino acid which in the desired end-product is in position 12 if n is 12, or in position 14 if n is 14, or in position 18 if n is 18, any functional group which may be present in said N-protected amino acid derivative being likewise appropriately protected;
  (i) removing the N-protecting group from the product thus obtained;
  (j) coupling the product thus obtained with an appropriately N-protected derivative of that amino acid which in the desired end-product is one position farther away from position 12 if n is 12 or in position 14 if n is 14, or from position 18 if n is 18, any functional group which may be present in said N-protected amino acid derivative being likewise appropriately protected;
  (k) removing the N-protecting group from the product thus obtained;
  (l) repeating steps (j) and (k) until all amino acid residues have been introduced;
  (m) if desired, selectively deprotecting one or several protected functional group(s) present in the molecule and appropriately substituting the reactive group(s) thus liberated;
  (n) if desired, forming one, two or three interstrand linkage(s) between side-chains of appropriate amino acid residues at opposite positions of the β-strand region;

(o) detaching the product thus obtained from the solid support;

(p) cyclizing the product cleaved from the solid support;

(q) removing any protecting groups present on functional groups of any members of the chain of amino acid residues and, if desired, any protecting group(s) which may in addition be present in the molecule; and (r) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Alternatively, the peptidomimetics of the present invention can be prepared by (a') coupling an appropriately functionalized solid support with a compound of the general formula

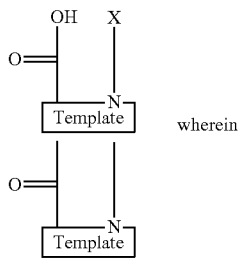   II wherein is as defined above and X is an N-protecting group or, alternatively, if

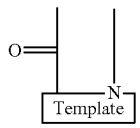

is to be group (a1) or (a2), above.

(a'a) coupling said appropriately functionalized solid support with an appropriately N-protected derivative of an amino acid of the general formula

HOOC—B—H      III or

HOOC-A-H      IV wherein B and A are as defined above, any functional group which may be present in said N-protected amino acid derivative being likewise appropriately protected;

(a'b) removing the N-protecting group from the product thus obtained; and (a'c) coupling the product thus obtained with an appropriately N-protected derivative of an amino acid of the above general formula IV and, respectively, III, any functional group which may be present in said N-protected amino acid derivative being likewise appropriately protected; and, respectively, if

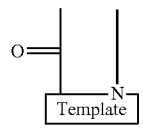

is to be group (a3), above, (a'a') coupling the product obtained in step (e) with an appropriately N-protected derivative of an amino acid of the above general formula II, any functional group which may be present in said N-protected amino acid derivative being likewise appropriately protected;

(a'b') removing the N-protecting group from the product thus obtained; and (a'c') coupling the product thus obtained with an appropriately N-protected derivative of an amino acid of the above general formula III, any functional group which may be present in said N-protected amino acid derivative being likewise appropriately protected;

(b') removing the N-protecting group from the product obtained in step (a'), (a'c) or (a'c');

(c') coupling the product thus obtained with an appropriately N-protected derivative of that amino acid which in the desired end-product is in position 12 if n is 12, or in position 14 if n is 14, or in position 18 if n is 18, any functional group which may be present in said N-protected amino acid derivative being likewise appropriately protected;

(d') removing the N-protecting group from the product thus obtained;

(e') coupling the product thus obtained with an appropriately N-protected derivative of that amino acid which in the desired end-product is one position farther away from position 12 if n is 12, or from position 14 if n is 14, or from position 18 if n is 18, any functional group which may be present in said N-protected amino acid derivative being likewise appropriately protected;

(f') removing the N-protecting group from the product thus obtained;

(g') repeating steps (e') and (f') until all amino acid residues have been introduced;

(h') if desired, selectively deprotecting one or several protected functional group(s) present in the molecule and appropriately substituting the reactive group(s) thus liberated;

(i') if desired forming one, two or three interstrand linkage(s) between side-chains of appropriate amino acid residues at opposite positions of the β-strand region;

(j') detaching the product thus obtained from the solid support;

(k') cyclizing the product cleaved from the solid support;

(l') removing any protecting groups present on functional groups of any members of the chain of amino acid residues and, if desired, any protecting group(s) which may in addition be present in the molecule; and (m') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Introducing an amino acid residue of type I can, alternatively, be effected by coupling with a leaving group-containing acylating agent, such as bromo, chloro or iodo acetic acid, followed by nucleophilic displacement with an amine of the formula $H_2N-R^{86}$ which, if necessary, is appropriately protected.

The peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^7$.

The structural element -A-CO— designates amino acid building blocks which in combination with the structural element —B—CO— form templates (a1) and (a2). The structural element —B—CO— forms in combination with another structural element —B—CO— template (a3). Preferably template (a3) is present only in formula I wherein n is 18 in chain Z. Templates (a) through (p) constitute building blocks which have an N-terminus and a C-terminus oriented in space in such a way that the distance between those two groups may lie between 4.0-5.5 A. A peptide chain Z is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5 A the template will induce the H-bond network necessary for the formation of a β-hairpin conformation in the peptide chain Z. Thus template and peptide chain form a β-hairpin mimetic.

The β-hairpin conformation is highly relevant for the CXCR4 antagonizing activity of the β-hairpin mimetics of the present invention. The β-hairpin stabilizing conformational properties of the templates (a) through (p) play a key role not only for the selective CXCR4 antagonizing activity but also for the synthesis process defined hereinabove, as incorporation of the templates at the beginning or near the middle of the linear protected peptide precursors enhances cyclization yields significantly.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are -$^D$A1-CO—$^L$B—CO— to $^D$A69-CO—$^L$B—CO—. Thus, for example, $^D$Pro-$^L$Pro constitutes the prototype of templates (a1). Less preferred, but possible are combinations -$^L$A1-CO—$^D$B—CO— to $^L$A69-CO—$^D$B—CO— forming templates (a2). Thus, for example, $^L$Pro-$^D$Pro constitutes the prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^7$ are:

$R^2$: H; lower alkyl; lower alkenyl; $(CH_2)_mOR^{55}$ (where $R^{55}$: lower alkyl; or lower alkenyl); $(CH_2)_mSR^{56}$ (where $R^{56}$: lower alkyl; or lower alkenyl); $(CH_2)_m NR^{33}R^{34}$ (where $R^{33}$: lower alkyl; or lower alkenyl; $R^{34}$: H; or lower alkyl; $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together from: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —(CH$_2$)$_m$NR$^{20}$CONR$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_2$N(R$^{20}$)COR$^{64}$ (where R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkenyl; lower alkenyl; or lower alkoxy).

R$^4$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^3$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkenyl; lower alkenyl; or lower alkoxy).

R$^5$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; R$^{57}$: where H; or lower alkyl); (CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: alkyl; alkenyl; aryl; and aryl-lower alkyl; heteroaryl-lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkenyl; or lower alkoxy).

R$^6$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{59}$R$^{59}$ (where R$^{58}$: lower alkyl; or lower alkenyl; and R$^{59}$: H; or lower alkyl; or F$^{58}$ and R$^{59}$ taken together from: (CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkenyl; lower alkenyl; or lower alkoxy).

R$^7$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_q$NR$^{20}$CONR$^{33}$R$^{82}$ (where R$^{20}$: H; or lower lower alkyl; R$^{33}$: H; or lower alkyl; or lower alkyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); $(CH_2)rSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; $-(CH_2)_o$ $OR^{55}$ (where $R^{55}$: lower alkyl; or lower alkenyl); $(CH_2)_o$ $SR^{56}$ (where $R^{56}$: lower alkyl; or lower alkenyl); $-(CH_2)NR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_o$ $OCONR^{33}R^{75}$ (where $R^{33}$: H; or lower alkyl; or lower alkenyl; $R^{75}$: lower alkyl; or $R^{33}$ and $R^{75}$ taken together from: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together from: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^9$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_o$ $NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2$ $O(CH_2)-$; $-(CH_2)_2S(CH_2)_2-$; or $-(CH_2)_2NR^{57}(CH_2)_2-$; where $R^{57}$: H; or lower alkyl); $-(CH_2)_oPO$ $(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; $-(CH_2)_mOR^{55}$ (where $R^{55}$: lower alkyl; or lower alkenyl); $-(CH_2)_m$ $SR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; $-(CH_2)_mOR^{55}$ (where $R^{55}$: lower alkyl; or lower alkenyl); $-(CH_2)_m$ $SR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S$ $(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH)_rPO(OR^{60})_2$ (where $R^{60}$: lower alkyl; or lower alkenyl); —$(CH_2)_oSO_2R^6$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{13}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_rSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{14}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O$ $(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_mN$ $(R^{20})COR^{64}$ (where: $R^{64}$ (where: $R^{20}$: H; lower alkyl; $R^{64}$: lower alkyl; or lower alkenyl); —$(CH_2)_oCOOR^{57}$ (where $R^{57}$: lower alkyl; or lower alkenyl); —$(CH_2)_o$ $CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH)_oPO(OR^{60})_2$ (where $R^{60}$: lower alkyl; or lower alkenyl); —$(CH_2)_o$ $SO_2R^{62}$ (where $R^{62}$: lower alkyl; or lower alkenyl); —$(CH_2)_qC_6H_4R^8$ (where $R^8$: H; F; Cl; CF$_3$; lower alkyl; lower alkenyl; or lower alkoxy).

$R^{15}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{34}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl); or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl; —$(CH_2)_oNR^{20}CONR^{33}R^{82}$ (where $R^{20}$: H; or lower lower alkyl; $R^{33}$: H; or lower alkyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); $(CH_2)_oN(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_oCOOR^{57}$ (where $R^{57}$: lower alkyl; or lower alkenyl); —$(CH_2)_o$ $CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_o$ $SO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{16}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_2OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$) where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—$(CH_2)_2S(CH_2)_2$—;

or —(CH$_2$)$_2$NR$^{57}$(CH$_2$)$_2$—; where R$^{57}$: H; or lower lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{17}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: lower alkyl; alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); —(CH$_2$)$_q$N (R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Most preferred are building blocks of type A8':

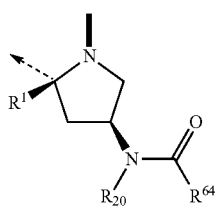

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-aminopropyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chain α-substituted α-amino acids, building blocks A71 and A72 to the corresponding 1-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers,* 1968, 6, 1425-1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids". *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Miller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900: D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schinholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for R$^{20}$ in A70 to A104 are H or lower alkyl with methyl being most preferred. Preferred values for R$^{18}$, R$^{19}$ and R$^{21}$-R$^{29}$ in building blocks A70 to A104 are the following:

R$^{18}$: lower alkyl.

R$^{19}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$ NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)—; —(CH$_2$)$_2$S(CH$_2$—; or —(CH$_2$)$_2$ NR$^{57}$(CH$_2$)$_2$—; where R$^{57}$: H; or lower alkyl); —(CH$_2$)$_p$ NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_pSO_2R^{62}$ (where $R^{62}$: lower alkyl; or lower alkenyl); or —$(CH_2)_oC_6H_4R^8$ (where $R^8$: H; F; Cl; $CF_3$; lower alkyl; lower alkenyl; or lower alkoxy).

$R^{21}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{22}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^3$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{87}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF; lower alkyl; lower alkenyl; or lower alkoxy).

$R^{23}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_o$ $COOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2\text{-}6}$—; —$(CH_2)_2O$ $(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_oPO$ $(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy);

$R^{24}$: lower alkyl; lower alkenyl; —$(CH_2)_oOR^{55}$ (where $R^{55}$: lower alkyl; or lower alkenyl); —$(CH_2)SR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_o$ $COOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2\text{-}6}$—; —$(CH_2)_2O$ $(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_oPO$ $(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy);

$R^{25}$: H; lower alkyl; lower alkenyl; —$(CH_2)_mOR^{55}$ (where $R^{55}$: lower alkyl; or lower alkenyl); —$(CH_2)_m$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2\text{-}6}$—; —$(CH_2)_2O(CH_2)_2$—; —$(CH_2)_2S$ $(CH_2$—; or —$(CH_2)_2NR^{57}(CH_2)_2$—; where $R^{57}$: H; or lower alkyl); —$(CH_2)_mCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$ $(CH_2)_2$—; where $R^{57}$: H; or lower alkyl); —$(CH_2)_m$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_m$N$(R^{20})$COR$^{64}$ (where: $R^{20}$: H; or lower alkyl; $R^{64}$: lower alkyl; or lower alkenyl); —$(CH_2)_o$COOR$^{57}$ (where $R^{57}$: lower alkyl; or lower alkenyl); —$(CH_2)_o$CONR$^{58}$R$^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$PO$(OR^{60})_2$ (where $R^{60}$: lower alkyl; or lower alkenyl); —$(CH_2)_o$SO$_2$R$^{62}$ (where $R^{62}$: lower alkyl; or lower alkenyl); or —$(CH_2)_q$C$_6$H$_4$R$^8$ (where $R^8$: H; F; Cl; CF$_3$; lower alkyl; lower alkenyl; or lower alkoxy).

$R^{26}$: H; lower alkyl; lower alkenyl; —$(CH_2)_m$OR$^{55}$ (where $R^{55}$: lower alkyl; or lower alkenyl); —$(CH_2)_m$NR$^{33}$R$^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_m$OCONR$^{33}$R$^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_m$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_m$N$(R^{20})$COR$^{64}$ (where: $R^{20}$: H; or lower alkyl; $R^{64}$: lower alkyl; or lower alkenyl); —$(CH_2)_o$COOR$^{57}$ (where $R^{57}$: lower alkyl; or lower alkenyl); —$(CH_2)_o$CONR$^{58}$R$^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$PO$(OR^{60})_2$ (where $R^{60}$: lower alkyl; or lower alkenyl); —$(CH_2)_o$SO$_2$R$^{62}$ (where $R^{62}$: lower alkyl; or lower alkenyl); or —$(CH_2)_q$C$_6$H$_4$R$^8$ (where $R^8$: H; F; Cl; CF$_3$; lower alkyl; lower alkenyl; or lower alkoxy).

Alternatively, $R^{25}$ and $R^{26}$ taken together can be —$(CH_2)_{2-6}$—; —$(CH_2)_2$O $(CH_2)_2$—; —$(CH_2)_2$S$(CH_2)_2$—; or —$(CH_2)_2$NR$^{57}$$(CH_2)_2$—; where $R^{57}$: H; or lower alkyl).

$R^{27}$: H; lower alkyl; lower alkenyl; —$(CH_2)_o$OR$^{55}$ (where $R^{55}$: lower alkyl; or lower alkenyl); —$(CH_2)_o$SR$^{56}$ (where $R^{56}$: lower alkyl; or lower alkenyl); —$(CH_2)_o$NR$^{33}$R$^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2$O$(CH_2)_2$—; —$(CH_2)_2$S $(CH_2)_2$—; or —$(CH_2)_2$N$^{57}$$(CH_2)_2$—; where $R^{57}$: H; or lower alkyl); —$(CH_2)_o$OCONR$^{33}$R$^{75}$ (where $R^{33}$: H; or lower alkyl; or lower alkenyl; $R^{75}$: lower alkyl; or $R^{33}$ and $R^{75}$ taken together form: —$(CH_2)_2$—; —; —$(CH_2)_2$O$(CH_2)_2$—; —$(CH_2)_2$S$((CH_2)_2$—; or —$(CH_2)_2$NR$^{57}$ $(CH_2)_2$—; where $R^{57}$: H; or lower alkyl); —$(CH_2)_o$ NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$O$(CH_2)_2$—; —$(CH_2)_2$S $(CH_2)_2$—; or —$(CH_2)_2$NR$^{57}$$(CH_2)_2$—; where $R^{57}$: H; or lower alkyl); —$(CH_2)_o$N$(R^{20})$COR$^{64}$ (where: $R^{20}$: H; or lower alkyl; $R^{64}$: lower alkyl; or lower alkenyl); —$(CH_2)_o$COOR$^{57}$ (where $R^{57}$: lower alkyl; or lower alkenyl); —$(CH_2)_o$CONR$^{58}$R$^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2$O$(CH_2)_2$—; —$(CH_2)_2$S $(CH_2)_2$—; or —$(CH_2)_2$NR$^{57}$$(CH_2)_2$—; where $R^{57}$: H; or lower alkyl); —$(CH_2)_o$PO$(OR^{60})_2$ (where $R^{60}$: lower alkyl; or lower alkenyl); —$(CH_2)_o$SO$_2$R$^{62}$ (where $R^{62}$: lower alkyl; or lower alkenyl); or —$(CH_2)_q$C$_6$H$_4$R$^8$ (where $R^8$: H; F; Cl; CF$_3$; lower alkyl; lower alkenyl; or lower alkoxy).

$R^{28}$: lower alkyl; lower alkenyl; —$(CH_2)_o$OR$^{55}$ (where $R^{55}$: lower alkyl; or lower alkenyl); —$(CH_2)_o$SR$^{56}$ (where $R^{56}$: lower alkyl; or lower alkenyl); —$(CH_2)_o$NR$^{33}$R$^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2$O$(CH_2)_2$—; —$(CH_2)_2$S $(CH_2)_2$—; or —$(CH_2)_2$NR$^{57}$$(CH_2)_2$—; where $R^{57}$: H; or lower alkyl); —$(CH_2)_o$OCONR$^{33}$R$^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$N$(R^{20})$COR$^{64}$ (where: $R^{20}$: H; or lower alkyl; $R^{64}$: lower alkyl; or lower alkenyl); —$(CH_2)_o$COOR$^{57}$ (where $R^{57}$: lower alkyl; or lower alkenyl); —$(CH_2)_o$CONR$^{58}$R$^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2$O$(CH_2)_2$—; —$(CH_2)_2$S $(CH_2)_2$—; or —$(CH_2)_2$NR$^{57}$$(CH_2)_2$—; where $R^{57}$: H; or lower alkyl); —$(CH_2)_o$PO$(OR^{60})_2$ (where $R^{60}$: lower alkyl; or lower alkenyl); —$(CH)_o$SO$_2$R$^{62}$ (where $R^{62}$: lower alkyl; or lower alkenyl); or —$(CH_2)_q$C$_6$H$_4$R$^8$ (where $R^8$: H; F; Cl; CF$_3$; lower alkyl; lower alkenyl; or lower alkoxy).

$R^{29}$: lower alkyl; lower alkenyl; —$(CH_2)_o$OR$^{55}$ (where $R^{55}$: lower alkyl; or lower alkenyl); —$(CH_2)_o$SR$^{56}$ (where $R^{56}$: lower alkyl; or lower alkenyl); —$(CH_2)_o$NR$^{33}$R$^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2$O$(CH_2)_2$—; —$(CH_2)_2$S $(CH_2)_2$—; or —$(CH_2)_2$NR$^{57}$$(CH_2)_2$—; where $R^{57}$: H; or lower alkyl); —$(CH_2)_o$OCONR$^{33}$R$^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where $R^{57}$: H; or lower alkyl); —$(CH_2)_o$N$(R^{20})$COR$^{64}$ (where: $R^{20}$: H; or lower alkyl; $R^{64}$: lower alkyl; or lower alkenyl); particularly favored are NR$^{20}$CO lower-alkyl ($R^{20}$=H; or lower alkyl); —$(CH_2)_o$ COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

For templates (b) to (p), such as (b1) and (c1), the preferred values for the various symbols are the following:

R$^8$: H; F; Cl; CF$_3$; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{20}$: H; or lower alkyl.

R$^{30}$: H, methyl.

R$^{31}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); (—(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_r$C$_6$H$_4$R$^8$ (where R$^8$: H; F; Cl; CF$_3$; lower alkyl; lower alkenyl; or lower alkoxy); most preferred is 13 CH$_2$CONR$^{58}$R$^{59}$ (R$^{58}$: H; or lower alkyl; R$^{59}$: lower alkyl; or lower alkenyl).

R$^{32}$: H, methyl.

R$^{33}$: lower alkyl; lower alkenyl; —(CH$_2$)$_m$OR$^{55}$ (where R$^{55}$: lower alkyl; or lower alkenyl); —(CH$_2$)$_m$NR$^{34}$R$^{63}$ (where R$^{34}$: lower alkyl; or lower alkenyl; R$^{63}$: H; or lower alkyl; or R$^{34}$ and R$^{63}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_m$OCONR$^{75}$R$^{82}$ (where R$^{75}$: lower alkyl; or lower alkenyl; R$^{82}$: H; or lower alkyl; or R$^{75}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{78}$R$^{82}$ (where R$^{20}$: H; or lower lower alkyl; R$^{78}$: H; or lower alkyl; or lower alkenyl; R$^{82}$: H; or lower alkyl; or R$^{78}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{34}$: H; or lower alkyl.

R$^{35}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{28}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{36}$: lower alkyl; lower alkenyl; or aryl-lower alkyl.

R$^{37}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$-; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H;

or lower alkyl; or lower alkenyl; $R^{75}$: lower alkyl; or $R^{33}$ and $R^{75}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pN(R^{20})COR^{64}$ (where: $R^{20}$: H; or lower alkyl; $R^{64}$: lower alkyl; or lower alkenyl); $—(CH_2)_oCOOR^{57}$ (where $R^{57}$: lower alkyl; or lower alkenyl); $—(CH)_oCONR^{58}R^{59}$ (where $R^{58}$: lower alkyl, or lower alkenyl; and $R^{59}$: H; lower alkyl; or $R^{58}$ and $R^{59}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_oPO(OR^{60})_2$ (where $R^{60}$: lower alkyl; or lower alkenyl); $—(CH_2)_oSO_2R^{62}$ (where $R^{62}$: lower alkyl; or lower alkenyl); or $—(CH_2)_qC_6H_4R^8$ (where $R^8$: H; F; Cl; $CF_3$; lower alkyl; lower alkenyl; or lower alkoxy).

$R^{38}$: H; lower alkyl; lower alkenyl; $—(CH)_pOR^{55}$ (where $R^{55}$: lower alkyl; or lower alkenyl); $—(CH_2)_pNR^{33}R^{34}$ (where $R^{33}$: lower alkyl; or lower alkenyl; $R^{34}$: H; or lower alkyl; or $R^{33}$ and $R^{34}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH)_pOCONR^{33}R^{75}$ (where $R^{33}$: H; or lower alkyl; or lower alkenyl; $R^{75}$: lower alkyl; or $R^{33}$ and $R^{78}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl; $—(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2$; where $R^{57}$: H; or lower alkyl); $—(CH_2)_pN(R^{20})COR^{64}$ (where: $R^{20}$: H; or lower alkyl; $R^{64}$: lower alkyl; or lower alkenyl); $—(CH_2)_oCOOR^{57}$ (where $R^{57}$: lower alkyl; or lower alkenyl); $—(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_oPO(OR^{60})_2$ (where $R^{60}$: lower alkyl; or lower alkenyl); $—(CH_2)_oSO_2R^{62}$ (where $R^{62}$: lower alkyl; or lower alkenyl); or $—(CH_2)_qC_6H_4R^8$ (where $R^8$: H; F; Cl; $CF_3$; lower alkyl; lower alkenyl; or lower alkoxy).

$R^{39}$: H; lower alkyl; lower alkenyl; $—(CH_2)_mOR^{55}$ (where $R^{55}$: lower alkyl; or lower alkenyl); $—(CH_2)_mN(R^{20})COR^{64}$ (where: $R^{20}$: H; or lower alkyl; $R^{64}$: lower alkyl; or lower alkenyl); $—(CH_2)_oCOOR^{57}$ (where $R^{57}$: lower alkyl; or lower alkenyl); $—(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl).

$R^{40}$: lower alkyl; lower alkenyl; or aryl-lower alkyl.

$R^{41}$: H; lower alkyl; lower alkenyl; $—(CH_2)_pOR^{55}$ (where $R^{55}$: lower alkyl; or lower alkenyl); $—(CH_2)_pNR^{33}R^{34}$ (where $R^{33}$: lower alkyl; or lower alkenyl; $R^{34}$: H; or lower alkyl; or $R^{33}$ and $R^{34}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pN(R^{20})COR^{64}$ (where: $R^{20}$: H; or lower alkyl; $R^{64}$: lower alkyl; or lower alkenyl); $—(CH_2)_oCOOR^{57}$ (where $R^{57}$: lower alkyl; or lower alkenyl); $—(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_oPO(OR^{60})_2$ (where $R^{60}$: lower alkyl; or lower alkenyl); $—(CH_2)_oSO_2R^{62}$ where $R^{62}$: lower alkyl; or lower alkenyl); or $—(CH_2)_qC_6H_4R^8$ (where $R^8$: H; F; Cl; $CF_3$; lower alkyl; lower alkenyl; or lower alkoxy).

$R^{42}$: H; lower alkyl; lower alkenyl; $—(CH_2)_pOR^{55}$ (where $R^{55}$: lower alkyl; or lower alkenyl); $—(CH_2)_pNR^{33}R^{34}$ (where $R^{33}$: lower alkyl; or lower alkenyl; $R^{34}$: H; or lower alkyl; or $R^{33}$ and $R^{34}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_pN(R^{20})COR^{64}$ (where: $R^{20}$: H; or lower alkyl; $R^{64}$: lower alkyl; or lower alkenyl); $—(CH_2)_oCOOR^{57}$ (where $R^{57}$: lower alkyl; or lower alkenyl); $—(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_oPO(OR^{60})_2$ (where $R^{60}$: lower alkyl; or lower alkenyl); $—(CH_2)_oSO_2R^{62}$ (where $R^{62}$: lower alkyl; or lower alkenyl); or $—(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; $—(CH_2)_mOR^{55}$ (where $R^{55}$: lower alkyl; or lower alkenyl); $—(CH_2)_mSR^{56}$ (where $R^{56}$: lower alkyl; or lower alkenyl); $—(CH_2)_mNR^{33}R^{34}$ (where $R^{33}$: lower alkyl; or lower alkenyl; $R^{34}$: H; or lower alkyl; or $R^{33}$ and $R^{34}$ taken together form: $—(CH_2)_{2-6}—$; $—(CH_2)_2O(CH_2)_2—$; $—(CH_2)_2S(CH_2)_2—$; or $—(CH_2)_2NR^{57}(CH_2)_2—$; where $R^{57}$: H; or lower alkyl); $—(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $—(CH_2)_{2-6}—$; $—(CH_2)(CH_2)_2—$; $—(CH_2)_2S(CH_2)_2—$; or $—(CH_2)_2NR^{57}(CH_2)_2—$; where $R^{57}$: H; or lower alkyl); $—(CH_2)_mNR^{20}CONR^{33}R^{82}$ where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $—(CH_2)_{2-6}—$; $—(CH_2)_2O$ $(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2S(CH_2)_2$—; or —$(CH_2)_2$ $NR^{57}(CH_2)_2$—; where $R^{57}$: H; or lower alkyl); —$(CH_2)_p$ $NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$—; where $R^{57}$: H; or lower alkyl); or —$(CH_2)_o$ $C_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_p$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sSR^{56}$ (where $R^{56}$: lower alkyl; or lower alkenyl); —$(CH_2)_s$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_s$ $NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_sN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$—; where $R^{57}$: H; or lower alkyl); or —$(CH_2)_s$ $C_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); or $(CH_2)_sC_6H_4R^8$ (where $R^8$: H; F; Cl; $CF_3$; lower alkyl; lower alkenyl; or lower alkoxy).

$R^{50}$: H; methyl.

$R^{51}$: H; lower alkyl; lower alkenyl; —$(CH_2)_mOR^{55}$ (where $R^{55}$: lower alkyl; or lower alkenyl); —$(CH_2)_m$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{52}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$ NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); or —(CH$_2$)$_r$C$_6$H$_4$R$^8$ (where R$^8$: H; F; Cl; CF$_3$; lower alkyl; lower alkenyl; or lower alkoxy).

$R^{53}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{58}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); or —(CH$_2$)$_r$C$_6$H$_4$R$^8$ (where R$^8$: H; F; Cl; CF$_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with R$^{22}$ being H, A75, A76, A77 with R$^{22}$ being H, A78 and A79.

The building block —B—CO— within templates (a1), (a2) and (a3) designates an L-amino acid residue. Preferred values for B are: —NR$^{20}$CH(R$^{71}$)— and enantiomers of groups A5 with R$^2$ being H, A8, A22, A25, A38 with R$^2$ being H, A42, A47, and A50. Most preferred are Ala L-Alanine
Arg L-Arginine
Asn L-Asparagine
Cys L-Cysteine
Gln L-Glutamine
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert-Butylglycine
4AmPhe L-para-Aminophenylalanine
3AnPhe L-meta-Aminophenylalanine
2AmPhe L-ortho-Aminophenylalanine
Phe(mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
C$_4$al L-3-Cyclobutylalanine
C$_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine
Dpr L-2,3-Diaminopropionic acid
A$_2$Bu L-2,4-Diaminobutyric acid
Dbu (S)-2,3-Diaminobutyric acid
Abu γ-Aminobutyric acid (GABA)
Aba ε-Aminohexanoic acid
Aib α-Aminoisobutyric acid
Y(Bzl) L-O-Benzyltyrosine
Bip L-Biphenylalanine
S(Bzl) L-O-Benzylserine
T(Bzl) L-O-Benzylthreonine
hCha L-Homo-cyclohexylalamine
hCys L-Homo-cysteine
hSer L-Homo-serine
hArg L-Homo-arginine
hPhe L-Homo-phenylalanine
Bpa L-4-Benzoylphenylalanine
Pip L-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methyaline
MeLeu L-N-Methylleucine In addition, the most preferred values for B also include groups of type A8" of (L)-configuration:

A8"

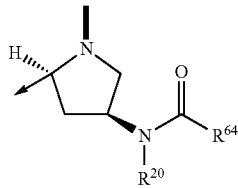

wherein $R^{20}$ is H or lower alkyl and $R^{64}$ is alkyl; alkenyl; —[(CH$_2$)$_2$u-X]$_t$—CH$_3$ (where X is —O—; —NR$^{20}$—, or —S—; u=1-3, and t=1-6), aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-amino-propyl (A8"-25); 5-amino-pentyl (A8"-26); methyl (A8"-27); ethyl (A8"¹-28); isopropyl (A8"-29); isobutyl (A8"-30); n-propyl (A8"-31); cyclohexyl (A8"-32); cyclohexylmethyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl)phenyl (A8"-39); n-nonyl (A8"-40); CH$_3$—OCH$_2$CH$_2$—OCH$_2$— (A8"-41) and CH$_3$—(OCH$_2$CH$_2$)$_2$—OCH$_2$— (A8"-42).

The peptidic chain Z of the β-hairpin mimetics described herein is generally defined in terms of amino acid residues belonging to one of the following groups:

Group C —NR$^{20}$CH(R$^{72}$)CO—; "hydrophobic: small to medium-sized"
Group D —NR$^{20}$CH(R$^{73}$)CO—; "hydrophobic: large aromatic or heteroaromatic"
Group E —NR$^{20}$CH(R$^{74}$)CO—; "polar-cationic" and "urea-derived"
Group F —NR$^{20}$CH(R$^{84}$)CO—; "polar-non-charged or anionic"
Group H —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$; —NR$^{20}$—CH(CO—)-(—(CH$_2$)$_p$ NR$^{20}$CO(CH$_2$)$_p$—CH(CO—)—NR$^{20}$—; and —NR$^{20}$—CH(CO—)-(—(CH$_2$)$_p$NR$^{20}$CONR$^{20}$(CH$_2$)$_p$—CH (CO—)—NR$^{20}$—; "interstrand linkage"
Group I —NR$^{86}$CH$_2$CO—; "polar-cationic or hydrophobic"

Furthermore, the amino acid residues in chain Z can also be of formula -A-CO— or of formula —B—CO— wherein A and B are as defined above. Finally, Gly can also be an amino acid residue in chain Z, and Pro can be an amino acid residue in chain Z, too, with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated n-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. The most widely known linkage is the disulfide bridge formed by cysteines and homocysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, Ill., 1984; Ahmed et al. J. Biol. Chem. 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

Group I comprises glycine having the amino group substituted by chains containing polar-cationic or hydrophobic residues according to the general definition for substituent $R^{86}$. Polar-cationic refers to a basic side chain which is protonated at physiological pH. A hydrophobic residue refers to an amino acid side chain that is uncharged at physiological pH and that is repelled by aqueous solution.

As mentioned earlier, positions for interstrand linkages are, if n is 12, positions P4 and P9; and/or P2 and P11 taken together; if n is 14, positions P2 and P13 and/or P4 and P11; and, if n is 18, positions P4 and P17 and/or P6 and P15 and/or P8 and P13 taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:
Cit L-Citrulline
Orn L-Ornithine
tBuA L-t-Butylalanine
Sar Sarcosine
Pen L-Penicillamine
t-BuG L-tert.-Butylglycine
4AmPhe L-para-Aminophenylalanine
3AmPhe L-meta-Aminophenylalanine
2AmPhe L-ortho-Aminophenylalanine
Phe(mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
C$_4$al L-3-Cyclobutylalanine
C$_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic 1,2,3,4-Tetrahydroisoquinoline-3-carboxylic acid
Thi L-β-2-Thienylalanine
Tza L-2-Thiazolylalanine
Mso L-Methionine sulfoxide
AcLys N-Acetyllysine
A$_2$Bu 2,4-Diaminobutyric acid
Dbu (S)-2,3-Diaminobutyric acid
Abu γ-Aminobutyric acid (GABA)
Aha ε-Aminohexanoic acid
Aib α-Aminoisobutyric acid
Y(Bzl) L-O-Benzyltyrosine
Bip L-(4-phenyl)phenylalanine
S(Bzl) L-O-Benzylserine
T(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L-4-Benzoylphenylalanine
4-AmPyrr1 (2S,4S)-4-Amino-pyrrolidine-L-carboxylic acid
4-AmPyrr2 (2S,4R)-4-Amino-pyrrolidine-L-carboxylic acid
4-PhePyrr1 (2S,5R)-4-Phenyl-pyrrolidine-L-carboxylic acid
4-PhePyrr2 (2S,5S)-4-Phenyl-pyrrolidine-L-carboxylic acid
5-PhePyrr1 (2S,5R)-5-Phenyl-pyrrolidine-L-carboxylic acid
5-PhePyrr2 (2S,5S)-5-Phenyl-pyrrolidine-L-carboxylic acid
Pro(4-OH) 1 (4S)-Hydroxyproline
Pro(4-OH)$_2$ (4R)-Hydroxyproline
Pip L-Pipecolic acid
$^D$Pip D-Pipecolic acid
OctG L-Octylglycine
NGly N-Methylglycine
MePhe L-N-Methylphenylalanine
MeNle L-N-Methylnorleucine
MeAla L-N-Methylalanine
MeIle L-N-Methylisoleucine
MeVal L-N-Methylvaline
MeLeu L-N-Methylleucine
DimK L-(N',N'Dimethyl)-lysine
Lpzp L-piperazinic acid
Dpzp D-piperazinic acid
Isom L-(N',N'-diisobutyl)-ornithine
PipAla L-2-(4'-piperidinyl)-alanine
PirrAla L-2-(3'-pyrrolidinyl)-alanine
Ampc 4-Amino-piperidine-4-carboxylic acid NMeR L-N-Methylarginine
NMeK L-N-Methyllysine
NMePhe L-N-Methylphenylalanine
IPegK  L-2-Amino-6-{2-[2-(2-methoxy-ethoxy)ethoxy]acetylamino}-hexanoic acid
SPegK L-2-Amino-6-[2-(2methoxy-ethoxy)-acetylamino]-hexanoic acid
Dab L-1,4-Diamino-butyric acid
IPegDab L-2-Amino-4{2-[2-(2-methoxy-ethoxy)-ethoxy]-acetylamino}-butyric acid
SPegDab  L-2-Amino-4[2-(2-methoxy-ethoxy)-acetylamino]butyric acid
4-PyrAla L-2-(4'Pyridyl)-alanine
OmPyr  L-2-Amino-5-[(2'carbonylpyrazine)]amino-pentanoic acid
BnG N-Benzylglycine
(4-OH)BnG N-4-Hydroxy-benzylglycine
IaG N-Isoamylglycine
IbG N-Isobutlyglycine
(EA)G N-(2-Aminoethyl)glycine
(PrA)G N-(3-Amino-n-propyl)glycine
(BA)G N-(4-Amino-n-butyl)glycine
(PeA)G N-(5-Amino-n-pentyl)glycine
$(PEG_3-NH_2)G$ N—[(CH$_2$)$_3$O—(CH$_2$—CH$_2$O)$_2$—(CH$_2$)$_3$—NH$_2$]glycine
(Pyrr)G N-{2-[2'-(1'-methyl-pyrrolidinyl)]-ethyl}-glycine
(Dimp)G N-[2-(N',N'-Dimethylamino)-propyl]-glycine
(Im)G N-[3-(1'-imidazolyl)-propyl]-glycine
(Pip)G N-{3-[1'-(4'-methylpiperazinyl)]-propyl}-glycine
(Dime)G N-[2-(N',N'-Dimethylamino)-ethyl]-glycine
  Particularly preferred residues for group C are:
Ala L-Alanine
Ile L-Isoleucine
Leu L-Leucine
Met L-Methionine
Val L-Valine
tBuA L-t-Butylalanine
t-BuG L-tert.-Butylglycine
Cha L-Cyclohexylalanine
C$_4$al L-3-Cyclobutylalanine
C$_5$al L-3-Cyclopentylalanine
Nle L-Norleucine
hCha L-Homo-cyclohexylalanine
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methylvaline
MeLeu L-N-Methylleucine
  Particularly preferred residues for group D are:
His L-Histidine
Phe L-Phenylalanine
Trp L-Tryptophan
Tyr L-Tyrosine
Phg L-Phenylglycine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Thi L-2-Thienylalanine
Tza L-2-Thiazolylalanine
Y(Bzl) L-O-Benzyltyrosine
Bip L-Biphenylalanine
S(Bzl) L-O-Benzylserine
T(Bzl) L-O-Benzylthreonine
hPhe L-Homo-phenylalanine
Bpa L-4-Benzoylphenylalanine
PirrAla L-2-(3'-pyrrolidinyl)-alanine
NMePhe L-N-Methylphenylalanine
4-PyrAla L-2-(4'Pyridyl)-alanine
  Particularly preferred residues for group E are
Arg L-Arginine
Lys L-Lysine
Orn L-Ornithine
Dpr L-2,3-Diaminopropionic acid
Dbu (S)-2,3-Diaminobutyric acid
Phe(pNH$_2$) L-para-Aminophenylalanine
Phe(mNH$_2$) L-meta-Aminophenylalanine
Phe(oNH$_2$) L-ortho-Aminophenylalanine
hArg L-Homo-arginine
Phe(mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
DimK L-(N',N'Dimethyl)-lysine
Isom L-(N',N'-diisobutyl)-ornithine
NMeR L-N-Methylarginine
NMeK L-N-Methyllysine
IPegK  L-2-Amino-6-{2-[2-(2-methoxy-ethoxy)ethoxy]acetylamino}-hexanoic acid
SPegK L-2-Amino-6-[2-(2methoxy-ethoxy)-acetylamino]-hexanoic acid
Dab L-1,4-Diamino-butyric acid
IPegDab L-2-Amino-4{2-[2-(2-methoxy-ethoxy)-ethoxy]-acetylamino}-butyric acid
SPegDab  L-2-Amino-4[2-(2-methoxy-ethoxy)-acetylamino]butyric acid
OmPyr  L-2-Amino-5-[(2'carbonylpyrazine)]amino-pentanoic
PipAla L-2-(4'-piperidinyl)-alanine
  Particularly preferred residues for group F are
Asn L-Asparagine
Asp L-Aspartic acid
Cys L-Cysteine
Gln L-Glutamine
Glu L-Glutamic acid
Ser L-Serine
Thr L-Threonine
Cit L-Citrulline
Pen L-Penicillamine
AcLys L-N-Acetyllysine
hCys L-Homo-cysteine
hSer L-Homo-serine
  Particularly preferred residues for group I are
(EA)G N-(2-Aminoethyl)glycine
(PrA)G N-(3-Amino-n-propyl)glycine
(BA)G N-(4-Amino-n-butyl)glycine
(PeA)G N-(5-Amino-n-pentyl)glycine
(EGU)G N-(2-Guanidinoethyl)glycine
(PrGU)G N-(3-Guanidino-n-propyl)glycine
(BGU)G N-(4-Guanidino-n-butyl)glycine
(PeGU)G N-(5-Guanidino-n-pentyl)glycine
$(PEG_3-NH_2)G$ N—[(CH$_2$)$_3$O—(CH$_2$—CH$_2$O)$_2$—(CH$_2$)$_3$—NH$_2$]glycine
(Pyrr)G N-{2-[2'-(1'-methyl-pyrrolidinyl)]-ethyl}-glycine
(Dimp)G N-[2-(N',N'-Dimethylamino)-propyl]-glycine
(Im)G N-[3-(1'-imidazolyl)-propyl]-glycine
(Pip)G N-{3-[1'-(4'-methylpiperazinyl)]-propyl}-glycine
(Dime)G N-[2-(N',N'-Dimethylamino)-ethyl]-glycine Generally, the peptidic chain Z within the β-hairpin mimetics of the invention comprises 12, 14 or 18 amino acid residues. The positions P1 to P12 and, respectively, to P14, or P18 of each amino acid residue in the chain Z are unequivocally defined as follows: P1 represents the first amino acid in the chain Z that is coupled with its N-terminus to the C-terminus of the templates (b)-(p), or of group —B—CO— in template (a1), or of group -A-CO— in template (a2), or of the group —B—CO— forming the C-terminus of template (a3); and P12 and, respectively, P14 or P18 represents the last amino acid in the chain Z that is coupled with its C-terminus to the N-terminus of the templates (b)-(p), or of group -A-CO— in template (a1), or of group —B—CO— in template (a2), or of the group —B—CO— forming the N-terminus of template (a3). Each of the positions P1 to P12 and, respectively, to P14 or P18 will preferably contain an amino acid residue belonging to one of the above types C D, E, F, I, H, or of formula -A-CO— or of formula —B—CO—, or being Gly, NMeGly, Pro or Pip as follows:

If n is 12 the α-amino acid residues in positions 1 to 12 of the chain Z are preferably:
P1: of type C, or of type D, or of type F, or the residue is Pro or Pip;
P2: of type E, or of type F, or the residue is Gly, NMeGly, Pro or Pip;
P3: or of type E, of type F;
P4: of type C, or of type D, or of type F, or the residue is Gly or NMeGly;
P5: of type E, or of type D, or of type F, or the residue is Gly, NMeGly, Pro or Pip;
P6: of type E, or of type F, or of formula —B—CO—, or the residue is Gly or NMeGly;
P7: of type E, or of type F;
P8: of type D, or of type C, or the residue is Pro or Pip;
P9: of type C, or of type D, or of type F, or the residue is Gly or NMeGly;
P10: of type D, or of type C, or the residue is Pro or Pip;
P11: of type E, or of type F, or the residue is Gly or NMeGly; and
P12: of type E or of type F, or the residue is Pro or Pip; or
P4 and P9, taken together, form a group of type H;
at P4, P6, P9 also D-isomers being possible.

If n is 12, the α-amino acid residues in positions 1 to 12 are most preferably:
P1: Tyr;
P2: Arg, Gly;
P3: Cit;
P4: Val, Phe, Gly, Ile, Thr, Gln, Cys;
P5: Arg;
P6: Arg, $^D$Arg;
P7: Arg;
P8: Trp, 2-Nal;
P9: Val, Phe, Gly, Ile, Thr, Gln, Cys;
P10: Tyr;
P11: Cit, Gly; and
P12: Lys; or
Cys at P4 and P9 form a disulfide bridge.

If n is 14, the α-amino acid residues in positions 1 to 14 of the chain Z are preferably:
P1: of type C, or of type D, or of type E, or of type F, or the residue is Gly or NMeGly or Pro or Pip;
P2: of type E, or of type D, or of type F;
P3: of type E, or of type F, or of type D, or of type C, or the residue is Pro or Pip;
P4: of type D, or of type C, or of type F;
P5: of type E, or of type F, or of type I;
P6: of type C, or of type D, or of type F, or the residue is Gly, NMeGly, Pro or Pip;
P7: of type C, or of type D, or of formula -A-CO—, or the residue is Gly, NMeGly, Pro or Pip;
P8: of type E, or of Type F, or of type D, or of type I, or thr residue is Pro or Pip;
P9: of type F, or of type E, or of type D, or of type I, or the residue is Pro or Pip;
P10: of type F, or of type D, or of type C;
P11: of type D, or of type C, or of type F, or of type E;
P12: of type C, or of type D, or of type F;
P13: of type F, or of type E, or of type D, or of type C, or of type I, or the residue is Gly or NMeGly; and
P14; or of type F, or of type E, or of type C; or
P2 and P13 and/or P4 and P11, taken together, form a group of type H;
at P4, P7, P8 or P11 D-isomers being possible;
with the proviso that
the amino acid residue in P1 is Gly or NMeGly or Pip; and/or
the amino acid residue in P2 is of type F; and/or
the amino acid residue in P3 is of type F, or it is Pro or Pip; and/or
the amino acid residue in P4 is of type F; and/or
the amino acid residue in P5 is of type F, or of type I; and/or
the amino acid residue in P6 is of type C, or of type D, or it is NMeGly or Pip; and/or
the amino acid residue in P7 is of type C, or of Type D, or it is NMeGly, Pro or Pip; and/or
the amino acid residue in P8 is of type D, or of type I, or it is Pro or Pip and/or
the amino acid residue in P9 is of type F, or of type I, or it is Pip; and/or
the amino acid residue in P10 is of type F; and/or
the amino acid residue in P11 is of type C; and/or
the amino acid residue in P12 is of type C, or of type F; and/or
the amino acid residue in P13 is of type F, or it is Gly or NMeGly; and/or P4 and P11, taken together, form a group of type H; and/or
the amino acid residue in P4 is a D-isomer; and/or
the amino acid residue in P11 is a D-isomer.

If n is 14, the α-amino acid residues in positions 1 to 14 are most preferably:
P1: Tyr, Gln, Arg, His, Ile, Trp, Thr, Glu, Ser, Val, Met, Phe, Gly, Asp, Leu, Pip;
P2: Arg, His, Lys, 4-PyrAla;
P3: Cit; Arg, His, Ile, Tyr, Trp, Pro, Glu, Asn, Asp, Lys, Ala, Leu, Val, 4F-Phe, Met, Ser, Thr, Gln, Tyr;
P4: Val, Phe, Tyr, t-BuG, Cys, Ser, Dab, Glu;
P5: Arg, Dab, Ser, (EA)G;
P6: Pro, Gly, Phe, Val, Cit, Ala;
P7: $^D$Pro, Pro, Gly, Val;
P8: Arg, Tyr, Trp, Thr, 4F-Phe, Dab, 4-PyrAla, Isorn, (Im)G, Cit, His, IpegDab, $^D$Pro;
P9: Arg, (Pip)G, (EA)G, Orn, Pro;
P10: 2-Nal, Trp, Tyr;
P11: Phe, Tyr, Val, t-BuG, Cys, Asn, Glu, Dab, Arg;
P12: Tyr, Cit;
P13: Cit, Gln, Arg, His, Tyr, Asn, Asp, Lys, Ala, Ser, Leu, Met, NMeGly, Thr, Cys; and
P14: Lys, Glu, Gln, Asn, Asp, Ala, Ser, NMeK;
with the Proviso that
the amino acid residue in P1 is Pip or Gly; and or
the amino acid residue in P3 is Glu, Asn, Asp, Thr, or Gln; and/or
the amino acid residue in P4 is Cys, Ser, or Glu; and/or the amino acid residue in P5 is Ser or (EA)G; and/or
the amino acid residue in P6 is Phe, Val, or Ala; and/or
the amino acid residue in P7 is Val, Pro, or $^D$Pro; and/or
the amino acid residue in P8 is Tyr, Trp, 4F-Phe, 4-PyrAla, (Im)G, His or $^D$Pro; and/or
the amino acid residue in P9 is (EA)G; and/or
the amino acid in P10 is Val or t-BuG; and/or
the amino acid residue in P12 is Tyr or Cit; and/or
the amino acid residue in P13 is Glu, Gln, Asp, Asn, Ser, Thr, Cys, or NMeGly; and/or
Cys at P4 and P11 form a disulfide bridge; and/or
Glu at P4 and Dab at P11 form a lactam bridge; and/or
Dab at P4 and Glu at P11 form a lactam bridge If n is 18, the amino acid residues in position 1-18 are most preferably:
P1: of type D, or of type E;
P2: of type E, or of type F;
P3: of type C, or of type D;
P4: of type E, or of type F;
P5: of type D, or of type E;
P6: of type E, or of type F;
P7: of type E, or of type F;
P8: of type E, or of type F, or the residue is Gly or NMeGly;
P9: of type D;
P10: of type E, or of formula -A1-A69-CO—, or the residue is Pro or Pip;
P11: of type E, or of formula —B—CO—, or the residue is Gly, NMeGly, Pro or Pip;
P12: of type D;
P13: of type F, or of type E, or the residue is Gly or NMeGly;
P14: of type C, or of type D;
P15: of type E, or of type F;
P16: of type E or of type F;
P17: of type E, or of type F; and
P18: of Type C or of type D or of type E or of Type F; or P4 and P17 and/or P6 and P15 and/or P8 and P13, taken together, form a group of type H;
at P10, P11 and P12 also D-isomers being possible.

If n is 18, the α-amino acid residues in positions 1 to 18 are most preferably:
P1: Arg;
P2: Arg;
P3: 2-Nal, Trp, Tyr;
P4: Cys;
P5: Tyr;
P6: Cit, Gln, Arg;
P7: Lys;
P8: Cys, Gly;
P9: Tyr;
P10: Lys, $^D$Lys, $^D$Pro;
P11: Gly, Pro, $^D$Pro;
P12: Tyr;
P13: Cys, Gly;
P14: Tyr;
P15: Arg;
P16: Cit, Thr, Lys;
P17: Cys; and
P18: Arg; or
Cys at P4 and P17 and/or at P8 and P13 form a disulfide bridge.

Particularly preferred β-peptidomimetics of the invention include those described in Examples 21, 22, 38, 45, 51, 52 53, 55, 56, 60, 61, 68, 75, 84, 85, 87, 101, 102, 105, 110, 120, 132, 147, 151, 152 and 160.

The processes of the invention can advantageously be carried out as parallel array syntheses to yield libraries of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acid conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido) aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as a parallel array syntheses the processes of the invention can be advantageously carried out as described herein below but it will be immediately apparent to those skilled in the art how these procedures will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2: 7) for 30 min.

Suitable protecting groups for amino acids and, respectively, for their residues are, for example,
for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph Phenyl
Pac Phenacyl
Allyl
Tse trimethylsilylethyl
Tce trichloroethyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf Pentamethyldihydrobenzofuran-5-sulfonyl
for the hydroxy group (as is present e.g. in the side-chain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/2% piperidine in DMF can be used.

N-substituted glycine derivatives (type 1) used as building blocks for the construction of certain compounds of formula I are derived from 9-fluorenylmethoxycarbonyl-(Fmoc)-protected amino acid derivatives or, alternatively, built up in two steps from leaving group-containing glycine precursors, such as bromo, chloro or iodo acetic acid, and suitable primary amine building blocks $NH_2$—$R^{86}$. The first synthesis step consists of the attachment of the leaving group-containing acetylating agent, such as bromo acetic acid, to the resin bound intermediate through formation of the amide bond. The second reaction step—the nucleophilic displacement—is accomplished using the primary amine building blocks, wherein the residues are, if necessary, suitably protected with groups as described above for side chains of amino acids.

For the incorporation of the N-substituted glycine derivatives as building blocks into the template-fixed β-hairpin loop mimetics the general synthesis procedure for assembling the hairpin mimetics is used as described herein.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, J. Am. Chem. Soc. 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, Kinig & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-dimethylamino)-phosphonium hexafluorophosphate (BOP, Castro et al., *Tetrahedron Lett.* 1975, 14, 1219-1222; Synthesis, 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-) 1,1,3,3-tetramethyluronium teraflouroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;
2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group for which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. For the formation of the pegylated amino acids such as IPegK, or SPegK, preferably a solution of 5 equivalents of HATU (N-[(dimethylamino)-1H-1,2,3-triazolo[4,5-b]pyridin-1-ylmethylene]-N-methylmethanaminium hexafluorophosphate N-oxide) in dry DMF and a solution of 10 equivalents of DIPEA (Diisopropyl ethaylamine) in dry DMF and 5 equivalents of 2-[2-(2-methoxyethoxy)ethoxy]acetic acid (IPeg) and, respectively, 2-(2-methoxyethoxy)acetic acid (sPeg), is applied to the liberated amino group of the appropriate amino acid side chain for 3 h. The procedure is thereafter repeated for another 3 h with a fresh solution of reagents after filtering and washing the resin.

Before this fully protected linear peptide is detached from the solid support, it is also possible, if desired, to form (an) interstrand linkage(s) between side-chains of appropriate amino acid residues at opposite positions of the β-strand region.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of disulfide bridges preferably a solution of 10 equivalents of iodine solution is applied in DMF or in a mixture of $CH_2Cl_2$/MeOH for 1.5 h which is repeated is repeated for another 3 h with a fresh iodine solution after filtering of the iodine solution, or in a mixture of DMSO and acetic acid solution, buffered with 5% with $NaHCO_3$ to pH 5-6 for 4 h, or in water after adjusted to pH 8 with ammonium hydroxide solution by stirring for 24 h, or in a solution of NMP and tri-n-butylphosphine (preferably 50 eq.).

For the formation of lactam bridges preferably a solution of 2 equivalents of HATU (N-[(dimethylamino)-1H-1,2,3-triazolo[4,5-b]pyridin-1-ylmethylene]-N-methylmethan-aminium hexafluorophosphate N-oxide) in dry DMF and a solution of 4 equivalents of DIPEA (Diisopropyl ethaylamine) in dry DMF is applied for 16 h.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Alternatively the detachment and complete deprotection of the fully protected peptide from the solid support can be achieved manually in glass vessels.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula I is obtained as end-product. Depending on its purity, this peptide derivative can be used directly for biological assays, or it has to be further purified, for example by preparative HPLC.

As mentioned earlier, it is thereafter possible, if desired, to convert a fully deprotected product of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The template starting materials of formula II used in the processes of the invention, pre-starting materials therefor, and the preparation of these starting and pre-starting materials are described in International Application PCT/EP02/01711 of the same applicants, published as WO 02/070547 A1.

The starting materials of formula $H_2NR^{86}$ are known or can be prepared by methods which are well known in the art.

The β-hairpin peptidomimetics of the invention can be used in a wide range of applications in order to prevent HIV infections in healthy individuals and slow or halt viral progression in infected patients, or where cancer is mediated or resulting from the CXCR4 receptor activity, or where immunological diseases are mediated or resulting from CXCR4 receptor activity, or the β-hairpin peptidomimetics of the invention can be used to treat immuno suppression, or they can be used during apheresis collections of peripheral blood stem cells.

The β-hairpin peptidomimetics may be administered per se or may be applied as an appropriate formulation together with carriers, diluents or excipients well known in the art.

When used to treat or prevent HIV infections or cancer such as breast cancer, brain cancer, prostate cancer, lung cancer, kidney cancer, neuroblastoma, non-hodgkin's lymphoma, ovarian cancer, multiple myeloma, chronic lyphomphocytic leukemia, pancreatic cancer, melanoma, angiogenesis, and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung disease (ILD), idiopathic pulmonary fibrosis, ILD associated with rheumatoid arthritis, systemic lupus erythematosus, ankylosing sponylitis, systemic sclerosis, Sjogren's syndrome, systemic anaphylaxis or hypersensitivity responses, drug allergies, rheumatoid arthritis, psoriatic arthritis, systemic lupus erythematosus, myasthenia gravis, juvenile onset diabetes, glomerulonephritis, autoimmune throiditis, graft rejection, including allograft rejection or graft-versus-host disease, inflammatory bowel diseases, inflammatory dermatoses; or to treat immunosuppression, including immunosuppression induced by chemotherapy, radiation therapy or graft/transplantation rejection, the β-hairpin peptidomimetics can be administered singly, as mixtures of several, β-hairpin peptidomimetics, in combination with other anti-HIV agents, or antimicrobial agents or anti cancer agents or anti-inflammatory agents, or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol;

cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the, β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethyluronium hexafluorophosphate (Knorr et al. *Tetrahedron Lett.* 1989, 30, 1927-1930);
HOBt: 1-hydroxybenzotriazole;
DIEA: diisopropylethylamine;
HOAT: 7-aza-1-hydroxybenzotriazole;
HATU: O-(7-aza-benzotriazole-1-yl)-N,N,N',N'-tetramethyluronoium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2Cl_2$ (2.5 ml) and allowed to swell at room temperature under constant stirring for 30 min. The resin was treated with 0.415 mMol (1 eq) of the first suitably protected amino acid residue (see below) and 284 µl (4 eq) of diisopropylethylamine (DIEA) in $CH_2Cl_2$ (2.5 ml), the mixture was shaken at 25° C. for 4 hours. The resin colour changed to purple and the solution remained yellowish. The resin was shaken ($CH_2Cl_2$/MeOH/DIEA:17/2/1), 30 ml for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours. Loading was typically 0.6-0.7 mMol/g.

The following preloaded resins were prepared: Fmoc-ProO-chlorotritylresin, Fmoc-$^D$ProO-chlorotritylresin, and Fmoc-S-(4-S-Alloc-amino)-ProO-chlorotritylresin.

Synthesis of the Fully Protected Peptide Fragment

The synthesis was carried out using a Syro-peptide synthesizer (Multisyntech) using 24 to 96 reaction vessels. In each vessel were placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min. |
| 3 | 40% piperidine/DMF | 1 × 5 min. |
| 4 | DMF, wash | 5 × 2 min. |
| 5 | 5 equiv. Fmoc amino acid/DMF + 5 eq. HBTU + 5 eq. HOBt + 5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid.

Pegylation of Side Chain Amino Functions with 2-[2-(2-methoxyethoxy)ethox]acetic acid and 2-(2-methoxyethoxy)acetic acid The resin (0.040 mmol) containing the peptide was swollen in 5 ml of freshly distilled $CH_2Cl_2$ for 30 min and then the palladium catalyst $Pd(PPh_3)_4$, 14 mg, 0.3 eq, was added followed by $PhSiH_3$, 0.8 mmol, 20 eq. The resin was shaken for 2 h and the reaction solution was filtered off. The reaction was repeated again by employing the same amount of reagents and after 2 h the resin was washed with $CH_2Cl_2$ and DMF and finally with $Et_2O$. The resin was swollen again in freshly distilled $CH_2Cl_2$ (2 ml) for 30 min, the solvent was filtered off and the resin swollen in DMF for 1 h. A solution of DIPEA (10 eq) in 1 ml of DMF was added followed by the addition of 2-[2-(2-methoxyethoxy)ethoxy]acetic acid or 2-(2-methoxyethoxy)acetic acid (5 eq) and finally by a solution of HATU (5 eq) in 1 ml of DMF. The resin was shaken for 3 h and the reaction solution was filtered off. The reaction was repeated again by employing the same amount of reagents and after 3 h the resin was washed with $CH_2Cl_2$ and DMF and finally with $Et_2O$.

The pegylation procedure was performed optionally, after the synthesis of the fully protected peptide fragment had been terminated, and then subsequently either Procedure A, Procedure B or Procedure C, as described hereinbelow, was adopted, depending on whether no intertrand linkages or disulfide, β-strand linkages or lactam β-strand linkages were to be formed.

Procedure A: Cyclization and Work Up of Backbone Cyclized Peptides

Cleavage of the Fully Protected Peptide Fragment

After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. The filtrate was evaporated to dryness and the product was fully deprotected [cleavage mixture containing 95% trifluoroacetic acid (TFA), 2.5% water and 2.5% triisopropylsilane (TIS)] to be analyzed by reverse phase-HPLC (column $C_{18}$) and ESI-MS to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 mMol, 3 eq.) of HATU, 14.9 mg (0.110 mMol, 3 eq) of HOAt and 1 ml (0.584 mMol) of 10% DIEA in DMF (v/v) were added, and the mixture was vortexed at 20° C. for 16 hours and subsequently concentrated under high vacuum. The residue was partitioned between $CH_2Cl_2$ and $H_2O$/$CH_3CN$ (90/10: v/v). The $CH_2Cl_2$ phase was evaporated to yield the fully protected cyclic peptide.

Deprotection and Purification of the Cyclic Peptide

The cyclic peptide obtained was dissolved in 1 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The residue was dissolved in a solution of $H_2O$/acetic acid (75/25: v/v) and the mixture was extracted with di-isopropylether.

The water phase was dried under vacuum and then the product was purified by preparative reverse phase HPLC.

After lyophilisation the products were obtained as white powders and analysed by ESI-MS. The analytical data comprising purity after preparative HPLC and ESI-MS are shown in Tables 1, 2 and 3.

Analytical Method 1:

Analytical HPLC retention times (RT, in minutes) were determined using a VYDAC 218MS5215 column with the following solvents A ($H_2O$+0.02% TFA) and B ($CH_3CN$) and the gradient: 0 min: 92% A, 8% B; 8 min: 62% A 38% B; 9-12 min: 0% A, 100% B.

Analytical Method 2:

Analytical HPLC retention times (RT, in minutes) were determined using an EX (s.n. 217808-2 column with the following solvents A ($H_2O+0.02\%$ TFA) and B ($CH_3CN$) and the gradient: 0 min: 95% A, 5% B; 8 min: 30% A 70% B; 9 min: 0% A, 100% B; 9-12 min: 95% A, 5% B.

Procedure B: Cyclization and Work Up of Backbone Cyclized Peptides Having Disulfide β-Strand Linkages Formation of Disulfide β-Strand Linkage After completion of the synthesis, the resin was swelled in 3 ml of dry DMF for 1 h. Then 10 eq. of iodine solution in DMF (6 ml) were added to the reactor, followed by stirring for 1.5 h. The resin was filtered and a fresh solution of iodine (10 eq.) in DMF (6 ml) was added, followed by stirring for another 3 h. The resin was filtered and washed with DMF (3×) and $CH_2Cl_2$ (3×).

Backbone Cyclization, Cleavage and Purification of the Peptide

After formation of the disulfide β-strand linkage, the resin was suspended in 1 ml (0.39 mMol) of 1% TFA in $CH_2Cl_2$ (v/v) for 3 minutes and filtered, and the filtrate was neutralized with 1 (1.17 mMol, 3 eq.) of 20% DIEA in $CH_2Cl_2$ (v/v). This procedure was repeated twice to ensure completion of the cleavage.

The volatiles were removed and 6 ml dry DMF were added to the tube. Then 2 eq. of HATU in dry DMF (1 ml) and 4 eq. of DIPEA in dry DMF (1 ml) were added to the peptide, followed by stirring for 16 h. The volatiles were evaporated to dryness. The crude cyclised peptide was dissolved in 7 ml of $CH_2Cl_2$ and extracted with 10% acetonitrile in $H_2O$ (4.5 ml) three times. The $CH_2Cl_2$ layer was evaporated to dryness. To deprotect the peptide fully, 3 ml of cleavage cocktail TFA:TIS:$H_2O$ (95:2.5:2.5) were added, and the mixture was kept for 2.5 h. The volatiles were evaporated to dryness and the crude peptide was dissolved in 20% AcOH in water (7 ml) and extracted with isopropyl ether (4 ml) for three times. The aqueous layer was collected and evaporated to dryness, and the residue was purified by preparative reverse phase HPLC.

After lyophilisation the products were obtained as white powders and analysed by ESI-MS analytical method 1 or 2. The analytical data comprising purity after preparative HPLC and ESI-MS are shown in Tables and 1, 2 and 3.

Procedure C: Cyclization and Work Up of Backbone Cyclized Peptides Having Lactam β-Strand Linkages Formation of Lactam β-Strand Linkage 0.036 mmol of the resin was taken in a reactor and swelled in dry DMF for 1 hr. To this 41.60 mg (1 eq.) of $Pd(PPh_3)_4$ and 0.133 ml (30 eq.) of $PhSiH_3$ were added and stirred overnight. The resin was filtered and washed thoroughly with DCM and DMF. The resin was swelled again in dry DMF for 1 hr. To this 1 ml DIPEA solution in DMF (24.64 μL of DIPEA in 1 ml DMF, 4 eq.) was added followed by 1 ml HATU solution in DMF (27.37 mg of HATU, 2 eq.) and the final volume of the reaction mixture was 7 ml and stirred overnight. The resin was washed thoroughly with DMF, $CH_2Cl_2$, DF, $CH_2Cl_2$.

Backbone Cyclization, Cleavage and Purification of the Peptide

The peptide was cleaved from the resin by 1% TFA in DCM and evaporated to dryness and 8 ml of dry DMF added to the tube. 2 equivalents of HATU in dry DMF (1 ml) and 4 equivalents of DIPEA in dry DMF (1 ml) were added to the peptide and stirred for 16 h. The volatiles were evaporated to dryness. The crude cyclised peptide was dissolved in 7 ml of DCM and extracted with 10% acetonitrile in $H_2O$ (4.5 ml) three times. The DCM layer was evaporated to dryness.

The crude cyclised peptide was dissolved in 7 ml of $CH_2Cl_2$ and extracted with 10% acetonitrile in $H_2O$ (4.5 ml) three times. The $CH_2Cl_2$ layer was evaporated to dryness. To deprotect the peptide fully, 3 ml of cleavage cocktail TFA:TIS:$H_2O$ (95:2.5:2.5) were added, and the mixture was kept for 2.5 h. The volatiles were evaporated to dryness and the crude peptide was dissolved in 20% AcOH in water (7 ml) and extracted with isopropyl ether (4 ml) for three times. The aqueous layer was collected and evaporated to dryness, and the residue was purified by preparative reverse phase HPLC.

After lyophilisation the products were obtained as white powders and analysed by ESI-MS analytical method 1 or 2. The analytical data comprising purity after preparative HPLC and ESI-MS are shown in Tables 1, 2 and 3.

Examples 1-6 and 8-11 (n=12) are shown in Table 1. The peptides were synthesized starting with the amino acid Pro which was grafted to the resin. Starting resin was Fmoc-ProO-chlorotrityl resin, which was prepared as described above. The linear peptides were synthesized on solid support according to the procedure described above in the following sequence: Resin-Pro-$^D$Pro-P12-P11-P10-P9-P8-P7-P6-P5-P4-P3-P2-P1. Thereafter they were cleaved from the resin, cyclized, deprotected and purified as indicated in procedure A.

HPLC-retention times (minutes) were determined using the gradient method 1 as described above:

Ex. 1 (4.98); Ex. 2 (4.62); Ex. 3 (5.63); Ex. 4 (5.33); Ex. 5 (5.12), Ex. 6 (4.75); Ex. 8 (5.08); Ex. 9 (6.17); Ex. 10 (6.28); Ex. 11 (6.57).

Examples 7 and 12-14 (n=12) are shown in Table 1, The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-$^D$Pro-P12-P11-P10-P9-P8-P7-P6-P5-P4-P3-P3-P2-P. Thereafter the disulfide bridges were formed and the peptides were cleaved from the resin, cyclized, deprotected and purified as indicated in procedure B.

HPLC-retention times (minutes) were determined using the gradient method 1 described above:

Ex. 7 (4.48); Ex. 12 (4.83); Ex. 13 (5.30); Ex. 14 (4.08).

Examples 15-50 (n=14) are shown in Table 2. The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-$^D$Pro-P14-P13-P12-P11-P10-P9-P8-P7-P6-P5-P4-P3-P2-P1. Thereafter they were cleaved from the resin, cyclized, deprotected and purified as indicated in procedure A.

HPLC-retention times (minutes) were determined using the gradient method 1 described above:

Ex. 15 (5.35); Ex. 16 (5.48); Ex. 17 (5.85); Ex. 18 (5.78); Ex. 19 (4.82); Ex. 20 (5.33); Ex. 21 (5.77), Ex. 22 (5.85); Ex. 23 (6.22); Ex. 24 (6.22); Ex. 25 (4.48); Ex. 26 (5.08); Ex. 27 (6.17); Ex. 28 (6.28); Ex. 29 (6.57); Ex. 30 (6.73); Ex. 31 (5.60); Ex. 32 (5.58); Ex. 33 (5.85); Ex. 34 (6.20); Ex. 35 (6.33); Ex. 36 (5.43); Ex. 37 (5.85); Ex. 38 (5.92); Ex. 39 (5.47); Ex. 40 (6.0, 6.37)*; Ex. 41 (5.13); Ex. 42 (5.00); Ex. 43 (5.00); Ex. 44 (5.33, 5.67)*, Ex. 45 (5.03); Ex. 46 (4.75); Ex. 47

(5.27); Ex. 48 (5.65, 6.08)*; Ex. 49 (5.03); Ex. 50 (5.75). * double peaks which show correct MS.

Examples 51-115, 117-141, 143-148 (n=14) are shown in Table 2. The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-$^D$Pro-P14-P13-P12-P11-P10-P9-P8-P7-P6-P5-P4-P3-P2-P1. Thereafter the disulfide bridges were formed, and the peptides were cleaved from the resin, cyclized, deprotected and purified as indicated in procedure B.

HPLC-retention times (minutes) were determined using the gradient method 1 for examples Ex 51-53, 138-139, for examples 54-115, 117-137, 140-141, 143-148 gradient method 2, as described above:

Ex. 51 (4.68); Ex. 52 (4.67); Ex. 53 (5.05), Ex. 54 (3.16), Ex. 55 (3.41), Ex. 56 (3.07), Ex. 57 (2.95), Ex. 58 (2.99), Ex. 59 (3.18), Ex. 60 (3.16), Ex. 61 (3.27), Ex. 62 (2.91), Ex. 63 (2.88), Ex. 64 (2.88), Ex. 65 (2.98), Ex. 66 (3.17), Ex. 67 (2.93), Ex. 68 (2.91), Ex. 69 (2.90), Ex. 70 (2.88), Ex. 71 (3.08), Ex. 72 (3.00), Ex. 73 (3.14), Ex. 74 (3.02), Ex. 75 (2.99), Ex. 76 (3.56), Ex. 77 (3.14), Ex. 78 (3.18), Ex. 79 (3.02), Ex. 80 (3.18), Ex. 81 (3.13), Ex. 82 (3.38), Ex. 83 (3.27), Ex. 84 (3.32), Ex. 85 (3.37), Ex. 86 (3.57), Ex. 87 (3.35), Ex. 88 (3.08), Ex. 89 (3.10), Ex. 90 (3.14), Ex. 91 (3.18), Ex. 92 (3.17), Ex. 93 (3.25), Ex. 94 (3.10), Ex. 95 (3.18), Ex. 96 (3.15), Ex. 97 (3.31), Ex. 98 (3.26), Ex. 99 (3.32), Ex. 100 (3.28), Ex. 101 (3.83), Ex. 102 (3.00), Ex. 103 (3.29), Ex. 104 (2.98), Ex. 105 (2.77), Ex. 106 (2.74), Ex. 107 (3.000, Ex. 108 (2.81), Ex. 109 (2.69, 2.75), Ex. 110 (2.76, 2.82*), Ex. 111 (2.73, 2.78), Ex. 112 (2.71), Ex. 113 (2.51), Ex. 114 (2.97), Ex. 115 (2.95), Ex. 117 (2.70), Ex. 118 (2.78), Ex. 119 (2.83), Ex. 120 (2.80), Ex. 121 (3.09), Ex. 122 (3.45), Ex. 123 (2.82), Ex. 124 (3.29), Ex. 125 (3.27), Ex. 126 (3.19), Ex. 127 (3.05), Ex. 128 (3.86), Ex. 129 (4.76), Ex. 130 (4.43), Ex. 131 (4.57), Ex. 132 (4.45), Ex. 133 (4.39), Ex. 134 (4.27), Ex. 135 (4.33), Ex. 136 (2.75), Ex. 137 (2.72), Ex. 138 (4.75), Ex. 139 (4.25), Ex. 140 (4.77), Ex. 141 (3.27), Ex. 143 (3.01), Ex. 144 (3.24), Ex. 145 (2.84), Ex. 146 (2.80), Ex. 147 (2.91), Ex. 148 (2.76). *double peaks which show correct MS.

Example 116 (n=14) is shown in Table 2. The peptide was synthesized starting with the amino acid Pro which was grafted to the resin. Starting resin was Fmoc-S-(4S-Alloc-amino)-ProO-chlorotrityl resin, which was prepared as described above. The linear peptide was synthesized on solid support according to procedure described above in the following sequence: Resin-S-(4-S-Alloc-amino)Pro-$^D$Pro-P14-P13-P12-P11-P10-P9-P8-P7-P6-P5-P4-P3-P2-P1. Then the pegylation procedure was applied using 2-[2-(2-methoxyethoxy)ethoxy]acetic acid resulting in $^D$ProA8"-42 as the template. Thereafter the disulfide bridge was formed, and the peptide was cleaved from the resin, cyclized, deprotected and purified as indicated in procedure B.

HPLC-retention time (minutes) was determined using gradient method 2 as described above: Ex. 116 (3.00).

Example 142 (n=14) is shown in Table 2. The peptide was synthesized starting with the amino acid Pro which was grafted to the resin. Starting resin was Fmoc-ProO-chlorotrityl resin, which was prepared as described above. The linear peptide was synthesized on solid support according to procedure described above in the following sequence: Resin-Pro-$^D$Pro-P14-P13-P12-P11-P10-P9-P8-P7-P6-P5-P4-P3-P3-P2-P1. Then the pegylation procedure was applied using 2-[2-(2-methoxyethoxy)ethoxy]acetic acid. Thereafter the disulfide bridge was formed, and the peptide was cleaved from the resin, cyclized, deprotected and purified as indicated in procedure B.

HPLC-retention time (minutes) was determined using the gradient method 2 as described above: Ex. 142 (3.18).

Example 149 (n=14) is shown in Table 2. The peptide was synthesized starting with the amino acid Pro which was grafted to the resin. Starting resin was Fmoc-ProO-chlorotrityl resin, which was prepared as described above. The linear peptide was synthesized on solid support according to procedure described above in the following sequence: Resin-Pro-$^D$Gln-P14-P13-P12-P11-P10-P9-P8-P7-P6-P5-P4-P3-P3-P2-P1. Thereafter the disulfide bridge was formed, and the peptide was cleaved from the resin, cyclized, deprotected and purified as indicated in procedure B.

HPLC-retention time (minutes) was determined using the gradient method 2 as described above: Ex. 149 (2.76).

Example 150 (n=14) is shown in table 2. The peptide was synthesized starting with the amino acid $^D$Pro which was grafted to the resin. Starting resin was Fmoc-$^D$ProO-chlorotrityl resin, which was prepared as described above. The linear peptide was synthesized on solid support according to procedure described above in the following sequence: Resin-$^D$Pro-Gly-P14-P13-P12-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the gradient method 2 as described above: Ex. 150 (2.61).

Example 151 (n=14) is shown in Table 2. The peptide was synthesized starting with the amino acid Pro which was grafted to the resin. Starting resin was Fmoc-ProO-chlorotrityl resin, which was prepared as described above. The linear peptide was synthesized on solid support according to procedure described above in the following sequence: Resin-Pro-$^D$Pro-P14-P13-P12-P11-P10-P9-P8-P7-P6-P5-P4-P3-P3-P2-P1. Thereafter the peptide was cleaved from the resin, cyclized, deprotected and purified as indicated in procedure A.

HPLC-retention time (minutes) was determined using gradient method 2 as described above: Ex. 151 (2.86).

Examples 152-153 (n=14) are shown in Table 2. The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-$^D$-Pro-P14-P13-P12-P11-P10-P9-P8-P7-P6-P5-P4-P3-P2-P1. Thereafter the lactam bridges were formed, and the peptides were cleaved from the resin, cyclized, deprotected and purified as indicated in procedure C.

HPLC-retention times (minutes) were determined using the gradient method 2 as described above:

Ex. 152 (2.87), Ex. 153 (2.87, 2.88*). *double peaks which show correct MS.

Examples 154-155 (n=18) are shown in Table 3. The peptides were synthesized starting with the amino acid $^D$Pro which was grafted to the resin. Starting resin was Fmoc-$^D$ProO-chlorotrityl resin, which was prepared as described above. The linear peptides were synthesized on solid support according to procedure described above in the following sequence: Resin-$^D$Pro-Gly-P18-P17-P16-P15-P14-P13-

P12-P11-P10-P9-P8-P7-P6-P5-P4-P3-P2-P1. Thereafter the disulfide bridges were formed using the following procedure:

For the formation of the disulfide bridge at position P4 and P17 the protected cyclic peptide (36 µmol) was swelled in dry DMF for 1 h. The DMF was drained off and was replaced by 2 ml NMP and 444 µl tri-n-butylphosphine (50 eq.) under argon. The resin was shaken for 2 h.

The solvents were removed and the resin was washed once with 5 ml NMP. Thereafter the resin was shaken again with 2 ml NMP and 444 µl tri-n-butylphosphine (50 eq.) under argon for 2 h. The resin was washed with DMF and transferred with 90 ml DMF into a 250 ml flask. 1 mmol (330 mg) [$K_3Fe(CN)_6$] in 10 ml water was added and the suspension was agitated gently overnight at 25° C. in the dark. The resin was transferred into a reactor and was washed with once with 7 ml water and twice with 5 ml DMF.

For the formation of the second disulfide bridge at position P8 and P13 the peptide was treated with 9 eq. (83 mg) iodine in 6 ml dry DMF for 2 h. The resin was washed once with DMF and the treatment with 9 eq. (83 mg) iodine in 6 ml DMF was repeated. The resin was washed three times with 5 ml DMF followed by three times with 5 ml $CH_2Cl_2$. The peptide was then cleaved from the resin, cyclized, deprotected and purified as indicated in procedure B.

HPLC-retention times (minutes) were determined using the gradient method 2 as described above: Ex. 154 (3.18), Ex. 155 (3.06).

Purity: %-purity of compounds after prep. HPLC: Ex. 154 (97), Ex. 155 (95).

Mass: [M+3H]/3: Ex. 154 (785.4), Ex. 155 (875.4).

Examples 156-157 (n=18) are shown in Table 3. The peptides were synthesized starting with the amino acid $^D$Pro which was grafted to the resin. Starting resin was Fmoc-$^D$ProO-chlorotrityl resin, which was prepared as described above. The linear peptides were synthesized on solid support according to procedure described above in the following sequence: Resin-$^D$Pro-Gly-P18-P17-P16-P15-P14-P13-P12-P11-P10-P9-P8-P7-P6-P5-P4-P3-P2-P1. Thereafter the disulfide bridges were formed, and the peptides were cleaved from the resin, cyclized, deprotected and purified as indicated in procedure B.

HPLC-retention times (minutes) were determined using the gradient method 2 as described above: Ex. 156 (3.00), Ex. 157 (2.98).

Purity: %-purity of compounds after prep. HPLC: Ex. 156 (95), Ex. 157 (76)

Mass: [M+3H]/3: Ex. 156 (845.5), Ex. 157(848.8)

Examples 158-159 (n=18) are shown in Table 3. The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-Gly-P18-P17-P16-P15-P14-P13-P12-P11-P10-P9-P8-P7-P6-P5-P4-P3-P2-P1. Thereafter the disulfide bridges were formed, and the peptides were cleaved from the resin, cyclized, deprotected and purified as indicated in procedure B.

HPLC-retention times (minutes) were determined using the gradient method 2 as described above: Ex. 158 (3.41), Ex. 159 (3.25)

Purity: %-purity of compounds after prep. HPLC: Ex. 158 (95), Ex. 159 (83)

Mass: [M+3H]/3: Ex. 158 (848.8), Ex. 159 (822.1).

Examples 160 (n=18) is shown in Table 3. The peptide was synthesized starting with the amino acid $^D$Pro which was grafted to the resin. Starting resin was Fmoc-$^D$ProO-chlorotrityl resin, which was prepared as described above. The linear peptide was synthesized on solid support according to procedure described above in the following sequence: Resin-$^D$Pro-Gly-P18-P17-P16-P15-P14-P13-P12-P11-P10-P9-P8-P7-P6-P5-P4-P3-P2-P1. Thereafter the following procedure was used:

The peptide (36 µmol) was cleaved from the resin by 1% TFA in $CH_2Cl_2$ After evaporation to dryness 8 ml of dry DMF were added to the tube. Then 2 eq. of HATU in dry DMF (1 ml) and 4 eq. of DIPEA in dry DMF (1 ml) were added and stirring was effected for 16 h. The volatiles were evaporated to dryness. The crude cyclised peptide was dissolved in 7 ml of DCM and extracted with 10% acetonitrile in $H_2O$ (4.5 ml) three times. The organic layer was evaporated to dryness. To deprotect the peptide fully, 3 ml of cleavage cocktail TFA:TIS:$H_2O$ (95:2.5:2.5) was added and kept for 3 h. The volatiles were evaporated to dryness and the crude peptide was dissolved in 20% acetic acid in water (7 ml) and extracted with isopropyl ether (4 ml) for three times. The aqueous layer was diluted up to 200 ml with water. The pH was adjusted to pH 8 with ammonium hydroxide solution. The reaction mixture was shaken for 24 h. The solution was acidified with acetic acid to pH 5, evaporated to dryness, and purified by HPLC.

HPLC-retention time (minutes) was determined using the gradient method 2 as described above: Ex. 160 (2.92)

Purity: %-purity of compounds after prep. HPLC: Ex. 160 (93)

Mass: [M+3H]/3: Ex. 160 (785.3).

TABLE 1

Examples n = 12

| Example | Sequ. ID | P1 | P2 | P3 | P4 | P5 | P6 | P7 | P8 | P9 | P10 | P11 | P12 | Template | Purity %[a] | [M + 2H]/2 |
|---|---|---|---|---|---|---|---|---|---|---|---|---|---|---|---|---|
| 1 | SEQ ID NO: 1 | Tyr | Arg | Cit | Val | Arg | $^D$Arg | Arg | 2-Nal | Phe | Tyr | Cit | Lys | $^D$Pro$^L$Pro | 83 | 1016.1 |
| 2 | SEQ ID NO: 2 | Tyr | Arg | Cit | Val | Arg | $^D$Arg | Arg | 2-Nal | Val | Tyr | Cit | Lys | $^D$Pro$^L$Pro | 100 | 992.4 |
| 3 | SEQ ID NO: 3 | Tyr | Arg | Cit | Phe | Arg | Arg | Arg | 2-Nal | Phe | Tyr | Cit | Lys | $^D$Pro$^L$Pro | 78 | 1040.4 |
| 4 | SEQ ID NO: 4 | Tyr | Arg | Cit | Val | Arg | Arg | Arg | 2-Nal | Phe | Tyr | Cit | Lys | $^D$Pro$^L$Pro | 83 | 1016.7 |
| 5 | SEQ ID NO: 5 | Tyr | Arg | Cit | Phe | Arg | Arg | Arg | 2-Nal | Val | Tyr | Cit | Lys | $^D$Pro$^L$Pro | 69 | 1016.2 |
| 6 | SEQ ID NO: 6 | Tyr | Arg | Cit | Val | Arg | Arg | Arg | 2-Nal | Val | Tyr | Cit | Lys | $^D$Pro$^L$Pro | 100 | 992.3 |

TABLE 1-continued

Examples n = 12

| Example | Sequ. ID | P1 | P2 | P3 | P4 | P5 | P6 | P7 | P8 | P9 | P10 | P11 | P12 | Template | Purity %[a] | [M + 2H]/2 |
|---|---|---|---|---|---|---|---|---|---|---|---|---|---|---|---|---|
| 7 | SEQ ID NO: 7 | Tyr | Arg | Cit | Cys | Arg | Arg | Arg | 2-Nal | Cys | Tyr | Cit | Lys | $^D$Pro$^L$Pro | 92 | 994.8 |
| 8 | SEQ ID NO: 8 | Tyr | Arg | Cit | Gly | Arg | Arg | Arg | 2-Nal | Gly | Tyr | Cit | Lys | $^D$Pro$^L$Pro | 100 | 1119.3 |
| 8 | SEQ ID NO: 9 | Tyr | Arg | Cit | Ile | Arg | Arg | Arg | 2-Nal | Ile | Tyr | Cit | Lys | $^D$Pro$^L$Pro | 100 | 4.98 |
| 10 | SEQ ID NO: 10 | Tyr | Arg | Cit | Thr | Arg | Arg | Arg | 2-Nal | Thr | Tyr | Cit | Lys | $^D$Pro$^L$Pro | 100 | 993.8 |
| 11 | SEQ ID NO: 11 | Tyr | Arg | Cit | Gln | Arg | Arg | Arg | 2-Nal | Gln | Tyr | Cit | Lys | $^D$Pro$^L$Pro | 100 | 1162.0 |
| 12 | SEQ ID NO: 12 | Tyr | Arg | Cit | Cys | Arg | $^D$Arg | Arg | 2-Nal | Cys | Tyr | Cit | Lys | $^D$Pro$^L$Pro | 100 | 996.1 |
| 13 | SEQ ID NO: 13 | Tyr | Gly | Cit | Cys | Arg | Arg | Arg | 2-Nal | Cys | Tyr | Gly | Lys | $^D$Pro$^L$Pro | 64 | 895.2 |
| 14 | SEQ ID NO: 14 | Tyr | Arg | Cit | Cys | Arg | Arg | Arg | Trp | Cys | Tyr | Cit | Lys | $^D$Pro$^L$Pro | 87 | 989.6 |

[a] %-purity of compounds after prep. HPLC

Cys in pos. 4 and 9 in Ex. 7, 12-14 form a disulfide bridge

TABLE 2

Examples n = 14

| Example | Sequ. ID | P1 | P2 | P3 | P4 | P5 | P6 | P7 | P8 | P9 |
|---|---|---|---|---|---|---|---|---|---|---|
| 15 | SEQ ID NO: 15 | Tyr | Arg | Cit | Val | Arg | Val | $^D$Pro | Arg | Arg |
| 16 | SEQ ID NO: 16 | Tyr | Arg | Cit | Val | Arg | Val | Pro | Arg | Arg |
| 17 | SEQ ID NO 17 | Tyr | Arg | Cit | Val | Arg | Phe | $^D$Pro | Arg | Arg |
| 18 | SEQ ID NO 18 | Tyr | Arg | Cit | Val | Arg | Phe | Pro | Arg | Arg |
| 19 | SEQ ID NO: 19 | Tyr | Arg | Cit | Phe | Arg | Cit | $^D$Pro | Arg | Arg |
| 20 | SEQ ID NO: 20 | Tyr | Arg | Cit | Phe | Arg | Cit | Pro | Arg | Arg |
| 21 | SEQ ID NO: 21 | Tyr | Arg | Cit | Phe | Arg | Val | $^D$Pro | Arg | Arg |
| 22 | SEQ ID NO: 22 | Tyr | Arg | Cit | Phe | Arg | Val | Pro | Arg | Arg |
| 23 | SEQ ID NO: 23 | Tyr | Arg | Cit | Phe | Arg | Phe | $^D$Pro | Arg | Arg |
| 24 | SEQ ID NO: 24 | Tyr | Arg | Cit | Phe | Arg | Phe | Pro | Arg | Arg |
| 25 | SEQ ID NO: 25 | Tyr | Arg | Cit | Val | Arg | Cit | $^D$Pro | Arg | Arg |
| 26 | SEQ ID NO: 26 | Tyr | Arg | Cit | Val | Arg | Cit | Pro | Arg | Arg |
| 27 | SEQ ID NO: 27 | Tyr | Arg | Cit | Phe | Arg | Val | $^D$Pro | Arg | Arg |
| 28 | SEQ ID NO: 28 | Tyr | Arg | Cit | Phe | Arg | Val | Pro | Arg | Arg |
| 29 | SEQ ID NO: 29 | Tyr | Arg | Cit | Phe | Arg | Phe | $^D$Pro | Arg | Arg |
| 30 | SEQ ID NO: 30 | Tyr | Arg | Cit | Phe | Arg | Phe | Pro | Arg | Arg |
| 31 | SEQ ID NO: 31 | Tyr | Arg | Cit | Val | Arg | Cit | Pro | Arg | Arg |
| 32 | SEQ ID NO: 32 | Tyr | Arg | Cit | Val | Arg | Val | $^D$Pro | Arg | Arg |
| 33 | SEQ ID NO: 33 | Tyr | Arg | Cit | Val | Arg | Val | Pro | Arg | Arg |
| 34 | SEQ ID NO: 34 | Tyr | Arg | Cit | Val | Arg | Phe | $^D$Pro | Arg | Arg |
| 35 | SEQ ID NO: 35 | Tyr | Arg | Cit | Val | Arg | Phe | Pro | Arg | Arg |
| 36 | SEQ ID NO: 36 | Tyr | Arg | Cit | Phe | Arg | Cit | $^D$Pro | Arg | Arg |
| 37 | SEQ ID NO: 37 | Tyr | Arg | Cit | Phe | Arg | Cit | Pro | Arg | Arg |
| 38 | SEQ ID NO: 38 | Tyr | Arg | Cit | Phe | Arg | Gly | $^D$Pro | Arg | Arg |
| 39 | SEQ ID NO: 39 | Tyr | Arg | Cit | Phe | Arg | Gly | Gly | Arg | Arg |
| 40 | SEQ ID NO: 40 | Tyr | Arg | Cit | Phe | Arg | Val | Gly | Arg | Arg |
| 41 | SEQ ID NO: 41 | Tyr | Arg | Cit | Tyr | Arg | Pro | Val | Arg | Arg |
| 42 | SEQ ID NO: 42 | Tyr | Arg | Cit | Tyr | Arg | Pro | Val | Arg | Arg |
| 43 | SEQ ID NO: 43 | Tyr | Arg | Cit | Tyr | Arg | Val | Gly | Arg | Arg |
| 44 | SEQ ID NO: 44 | Tyr | Arg | Cit | Val | Arg | Pro | Val | Arg | Arg |
| 45 | SEQ ID NO: 45 | Tyr | Arg | Cit | Val | Arg | Gly | $^D$Pro | Arg | Arg |
| 46 | SEQ ID NO: 46 | Tyr | Arg | Cit | Val | Arg | Gly | Gly | Arg | Arg |
| 47 | SEQ ID NO: 47 | Tyr | Arg | Cit | Val | Arg | Val | Gly | Arg | Arg |
| 48 | SEQ ID NO: 48 | Tyr | Arg | Cit | t-BuG | Arg | Pro | Val | Arg | Arg |
| 49 | SEQ ID NO: 49 | Tyr | Arg | Cit | t-BuG | Arg | Gly | Gly | Arg | Arg |
| 50 | SEQ ID NO: 50 | Tyr | Arg | Cit | t-BuG | Arg | Val | Gly | Arg | Arg |
| 51 | SEQ ID NO: 51 | Tyr | Arg | Cit | Cys | Arg | Gly | $^D$Pro | Arg | Arg |
| 52 | SEQ ID NO: 52 | Tyr | Arg | Cit | Cys | Arg | Gly | Gly | Arg | Arg |
| 53 | SEQ ID NO: 53 | Tyr | Arg | Cit | Cys | Arg | Val | Gly | Arg | Arg |
| 54 | SEQ ID NO 54 | Tyr | Arg | Cit | Cys | Arg | Gly | $^D$Pro | Tyr | Arg |
| 55 | SEQ ID NO 55 | Tyr | Arg | Cit | Cys | Arg | Gly | $^D$Pro | Trp | Arg |
| 56 | SEQ ID NO 56 | Tyr | Arg | Cit | Cys | Arg | Gly | $^D$Pro | Thr | Arg |
| 57 | SEQ. ID NO 57 | Tyr | Arg | Cit | Cys | Arg | Gly | $^D$Pro | Arg | Arg |
| 58 | SEQ. ID NO 58 | Tyr | Arg | Cit | Cys | Arg | Gly | $^D$Pro | Arg | Arg |
| 59 | SEQ. ID NO 59 | Tyr | Arg | Cit | Cys | Arg | Gly | $^D$Pro | Arg | Arg |
| 60 | SEQ. ID NO 60 | Tyr | Arg | Cit | Cys | Arg | Gly | $^D$Pro | Arg | Arg |
| 61 | SEQ. ID NO 61 | Tyr | Arg | Cit | Cys | Arg | Gly | $^D$Pro | Arg | Arg |

TABLE 2-continued

Examples n = 14

| | | | | | | | | | |
|---|---|---|---|---|---|---|---|---|---|
| 62 | SEQ. ID NO 62 | Gln | Arg | Cit | Cys | Arg | Gly | $^D$Pro | Arg | Arg |
| 63 | SEQ. ID NO 63 | Arg | Arg | Cit | Cys | Arg | Gly | $^D$Pro | Arg | Arg |
| 64 | SEQ. ID NO 64 | His | Arg | Cit | Cys | Arg | Gly | $^D$Pro | Arg | Arg |
| 65 | SEQ. ID NO 65 | Ile | Arg | Cit | Cys | Arg | Gly | $^D$Pro | Arg | Arg |
| 66 | SEQ. ID NO 66 | Trp | Arg | Cit | Cys | Arg | Gly | $^D$Pro | Arg | Arg |
| 67 | SEQ. ID NO 67 | Thr | Arg | Cit | Cys | Arg | Gly | $^D$Pro | Arg | Arg |
| 68 | SEQ. ID NO 68 | Glu | Arg | Cit | Cys | Arg | Gly | $^D$Pro | Arg | Arg |
| 69 | SEQ. ID NO 69 | Tyr | Arg | Arg | Cys | Arg | Gly | $^D$Pro | Arg | Arg |
| 70 | SEQ. ID NO 70 | Tyr | Arg | His | Cys | Arg | Gly | $^D$Pro | Arg | Arg |
| 71 | SEQ. ID NO 71 | Tyr | Arg | Ile | Cys | Arg | Gly | $^D$Pro | Arg | Arg |
| 72 | SEQ. ID NO 72 | Tyr | Arg | Tyr | Cys | Arg | Gly | $^D$Pro | Arg | Arg |
| 73 | SEQ. ID NO 73 | Tyr | Arg | Trp | Cys | Arg | Gly | $^D$Pro | Arg | Arg |
| 74 | SEQ. ID NO 74 | Tyr | Arg | Pro | Cys | Arg | Gly | $^D$Pro | Arg | Arg |
| 75 | SEQ. ID NO 75 | Tyr | Arg | Glu | Cys | Arg | Gly | $^D$Pro | Arg | Arg |
| 76 | SEQ. ID NO 76 | Tyr | Arg | Cit | Cys | Arg | Gly | $^D$Pro | 4F-Phe | Arg |
| 77 | SEQ. ID NO 77 | Tyr | Arg | Cit | Cys | Arg | Gly | $^D$Pro | Arg | Arg |
| 78 | SEQ. ID NO 78 | Tyr | Arg | Cit | Cys | Arg | Gly | $^D$Pro | Arg | Arg |
| 79 | SEQ. ID NO 79 | Tyr | Arg | Cit | Cys | Arg | Gly | $^D$Pro | Arg | Arg |
| 80 | SEQ. ID NO 80 | Tyr | Arg | Cit | Cys | Arg | Gly | $^D$Pro | Arg | Arg |
| 81 | SEQ. ID NO 81 | Tyr | Arg | Cit | Cys | Arg | Gly | $^D$Pro | Arg | Arg |
| 82 | SEQ. ID NO 82 | Tyr | Arg | Cit | Cys | Arg | Gly | $^D$Pro | Arg | Arg |
| 83 | SEQ. ID NO 83 | Tyr | Arg | Cit | Cys | Arg | Gly | $^D$Pro | Arg | Arg |
| 84 | SEQ. ID NO 84 | Tyr | Arg | Cit | Cys | Arg | Gly | $^D$Pro | Arg | Arg |
| 85 | SEQ. ID NO 85 | Tyr | Arg | Cit | Cys | Arg | Gly | $^D$Pro | Arg | Arg |
| 86 | SEQ. ID NO 86 | Tyr | Arg | Cit | Cys | Arg | Gly | $^D$Pro | Arg | Arg |
| 87 | SEQ. ID NO 87 | Tyr | Arg | Cit | Cys | Arg | Gly | $^D$Pro | Arg | Arg |
| 88 | SEQ. ID NO 88 | Asp | Arg | Cit | Cys | Arg | Gly | $^D$Pro | Arg | Arg |
| 89 | SEQ. ID NO 89 | Ser | Arg | Cit | Cys | Arg | Gly | $^D$Pro | Arg | Arg |
| 90 | SEQ. ID NO 90 | Val | Arg | Cit | Cys | Arg | Gly | $^D$Pro | Arg | Arg |
| 91 | SEQ. ID NO 91 | Met | Arg | Cit | Cys | Arg | Gly | $^D$Pro | Arg | Arg |
| 92 | SEQ. ID NO 92 | Tyr | Arg | Asn | Cys | Arg | Gly | $^D$Pro | Arg | Arg |
| 93 | SEQ. ID NO 93 | Tyr | Arg | Asp | Cys | Arg | Gly | $^D$Pro | Arg | Arg |
| 94 | SEQ. ID NO 94 | Tyr | Arg | Lys | Cys | Arg | Gly | $^D$Pro | Arg | Arg |
| 95 | SEQ. ID NO 95 | Tyr | Arg | Ala | Cys | Arg | Gly | $^D$Pro | Arg | Arg |
| 96 | SEQ. ID NO 96 | Tyr | Arg | Ser | Cys | Arg | Gly | $^D$Pro | Arg | Arg |
| 97 | SEQ. ID NO 97 | Tyr | Arg | Leu | Cys | Arg | Gly | $^D$Pro | Arg | Arg |
| 98 | SEQ. ID NO 98 | Tyr | Arg | Val | Cys | Arg | Gly | $^D$Pro | Arg | Arg |
| 99 | SEQ. ID NO 99 | Tyr | Arg | 4F-Phe | Cys | Arg | Gly | $^D$Pro | Arg | Arg |
| 100 | SEQ. ID NO 100 | Tyr | Arg | Met | Cys | Arg | Gly | $^D$Pro | Arg | Arg |
| 101 | SEQ. ID NO 101 | Tyr | Arg | Cit | Cys | Ser | Gly | $^D$Pro | Arg | Arg |
| 102 | SEQ. ID NO 102 | Tyr | Arg | Ser | Cys | Arg | Gly | $^D$Pro | Arg | Arg |
| 103 | SEQ. ID NO 103 | Tyr | Arg | Cit | Cys | Arg | Gly | $^D$Pro | Arg | Arg |
| 104 | SEQ. ID NO 104 | Tyr | Arg | Thr | Cys | Arg | Gly | $^D$Pro | Dab | Arg |
| 105 | SEQ. ID NO 105 | Tyr | His | Cit | Cys | Arg | Gly | $^D$Pro | Arg | Arg |
| 106 | SEQ. ID NO 106 | Tyr | Lys | Cit | Cys | Arg | Gly | $^D$Pro | Arg | Arg |
| 107 | SEQ. ID NO 107 | Phe | Arg | Cit | Cys | Arg | Gly | $^D$Pro | Arg | Arg |
| 108 | SEQ. ID NO 108 | Tyr | Arg | Cit | Cys | Arg | Gly | $^D$Pro | Arg | Arg |
| 109 | SEQ. ID NO 109 | Tyr | Arg | Cit | Cys | Arg | Gly | $^D$Pro | Dab | Arg |
| 110 | SEQ. ID NO 110 | Tyr | Arg | Thr | Cys | Arg | Gly | $^D$Pro | Dab | Arg |
| 111 | SEQ. ID NO 111 | Tyr | Arg | Cit | Cys | Dab | Gly | $^D$Pro | Arg | Arg |
| 112 | SEQ. ID NO 112 | Tyr | Arg | Cit | Cys | Arg | Gly | $^D$Pro | Arg | Arg |
| 113 | SEQ. ID NO 113 | Tyr | Arg | Cit | Cys | Arg | Gly | $^D$Pro | Arg | Arg |
| 114 | SEQ. ID NO 114 | Gly | Arg | Cit | Cys | Arg | Gly | $^D$Pro | Arg | Arg |
| 115 | SEQ. ID NO 115 | Tyr | Arg | Cit | Cys | Arg | Gly | $^D$Pro | Arg | Arg |
| 116 | SEQ. ID NO 116 | Tyr | Arg | Cit | Cys | Arg | Gly | $^D$Pro | Arg | Arg |
| 117 | SEQ. ID NO 117 | Tyr | Arg | Cit | Cys | Arg | Gly | $^D$Pro | Arg | Orn |
| 118 | SEQ. ID NO 118 | Tyr | Arg | Thr | Cys | Arg | Gly | $^D$Pro | 4-Pyr AlaArg | |
| 119 | SEQ. ID NO 119 | Tyr | 4-PyrAla | Thr | Cys | Arg | Gly | $^D$Pro | Arg | Arg |
| 120 | SEQ. ID NO 120 | Tyr | His | Thr | Cys | Arg | Gly | $^D$Pro | Arg | His |
| 121 | SEQ. ID NO 121 | Tyr | Arg | Cit | Cys | Arg | Gly | $^D$Pro | Arg | Arg |
| 122 | SEQ. ID NO 122 | Tyr | Arg | Cit | Cys | Arg | Gly | $^D$Pro | 4F-Phe | Arg |
| 123 | SEQ. ID NO 123 | Tyr | Arg | Cit | Cys | Arg | Gly | $^D$Pro | Arg | Arg |
| 124 | SEQ. ID NO 124 | Tyr | Arg | Cit | Cys | Arg | Gly | $^D$Pro | IsOrn | Arg |
| 125 | SEQ. ID NO 125 | Tyr | Arg | Cit | Cys | Arg | Gly | $^D$Pro | (Im)G | Arg |
| 126 | SEQ. ID NO 126 | Tyr | Arg | Cit | Cys | Arg | Gly | $^D$Pro | Arg | (Pip)G |
| 127 | SEQ. ID NO 127 | Tyr | Arg | Cit | Cys | Arg | Gly | $^D$Pro | Arg | Arg |
| 128 | SEQ. ID NO 128 | Tyr | Arg | Cit | Cys | Arg | Gly | $^D$Pro | Arg | Arg |
| 129 | SEQ. ID NO 129 | Tyr | Arg | Cit | Cys | Arg | Gly | $^D$Pro | Arg | Arg |
| 130 | SEQ. ID NO 130 | Tyr | Arg | Gln | Cys | Arg | Gly | $^D$Pro | Arg | Arg |
| 131 | SEQ. ID NO 131 | Tyr | Arg | Thr | Cys | Arg | Gly | $^D$Pro | Arg | Arg |
| 132 | SEQ. ID NO 132 | Tyr | Arg | Cit | Cys | Arg | Gly | $^D$Pro | Arg | Arg |
| 133 | SEQ. ID NO 133 | Tyr | Arg | Cit | Cys | Arg | Gly | $^D$Pro | Arg | Arg |
| 134 | SEQ. ID NO 134 | Tyr | Arg | Cit | Cys | Arg | Gly | $^D$Pro | Dab | Arg |
| 135 | SEQ. ID NO 135 | Tyr | Arg | Cit | Cys | Arg | Gly | $^D$Pro | Dab | Arg |
| 136 | SEQ. ID NO 136 | Tyr | Arg | Cit | Cys | Arg | Gly | $^D$Pro | Cit | Arg |
| 137 | SEQ. ID NO 137 | Tyr | Arg | Cit | Cys | Arg | Gly | $^D$Pro | His | Arg |
| 138 | SEQ. ID NO 138 | Tyr | Arg | Cit | Cys | (EA)G | Gly | $^D$Pro | Arg | Arg |
| 139 | SEQ. ID NO 139 | Tyr | Arg | Cit | Cys | Arg | Gly | Pro | Arg | (EA)G |

TABLE 2-continued

Examples n = 14

| | | | | | | | | | |
|---|---|---|---|---|---|---|---|---|---|
| 140 | SEQ. ID NO 140 | Tyr | Arg | Cit | Cys | Arg | Gly | $^D$Pro | Arg | Arg |
| 141 | SEQ. ID NO 141 | Tyr | Arg | Cit | Cys | Arg | Gly | $^D$Pro | Arg | Arg |
| 142 | SEQ. ID NO 142 | Tyr | Arg | Cit | Cys | Arg | Gly | $^D$Pro | lPegDab | Arg |
| 143 | SEQ. ID NO 143 | Tyr | Arg | Cit | Cys | Arg | Ala | $^D$Pro | Arg | Arg |
| 144 | SEQ. ID NO 144 | Leu | Arg | Cit | Cys | Arg | Gly | $^D$Pro | Arg | Arg |
| 145 | SEQ. ID NO 145 | Tyr | Arg | Thr | Cys | Arg | Gly | $^D$Pro | Arg | Arg |
| 146 | SEQ. ID NO 146 | Tyr | Arg | Thr | Cys | Arg | Gly | $^D$Pro | Arg | Arg |
| 147 | SEQ. ID NO 147 | Tyr | Arg | Ile | Cys | Arg | Gly | $^D$Pro | Arg | Arg |
| 148 | SEQ. ID NO 148 | Tyr | Arg | Tyr | Cys | Arg | Gly | $^D$Pro | Arg | Arg |
| 149 | SEQ. ID NO 149 | Tyr | Arg | Cit | Cys | Arg | Gly | $^D$Pro | Arg | Arg |
| 150 | SEQ. ID NO 150 | Pip | Arg | Tyr | Tyr | Tyr | Gln | Lys | $^D$Pro | Pro |
| 151 | SEQ. ID NO 151 | Tyr | Arg | Cit | Ser | Arg | Gly | $^D$Pro | Arg | Arg |
| 152 | SEQ. ID NO 152 | Tyr | Arg | Cit | Dab | Arg | Gly | $^D$Pro | Arg | Arg |
| 153 | SEQ. ID NO 153 | Tyr | Arg | Cit | Glu | Arg | Gly | $^D$Pro | Arg | Arg |

| Example | P10 | P11 | P12 | P13 | P14 | Template | Purity %[a)] | [M + 2H]/2 |
|---|---|---|---|---|---|---|---|---|
| 15 | 2-Nal | Val | Tyr | Cit | Lys | $^D$Pro$^L$Pro | 100 | 1090.2 |
| 16 | 2-Nal | Val | Tyr | Cit | Lys | $^D$Pro$^L$Pro | 100 | 1090.4 |
| 17 | 2-Nal | Val | Tyr | Cit | Lys | $^D$Pro$^L$Pro | 100 | 1114.8 |
| 18 | 2-Nal | Val | Tyr | Cit | Lys | $^D$Pro$^L$Pro | 100 | 1114.9 |
| 19 | 2-Nal | Val | Tyr | Cit | Lys | $^D$Pro$^L$Pro | 100 | 1143.6 |
| 20 | 2-Nal | Val | Tyr | Cit | Lys | $^D$Pro$^L$Pro | 100 | 1143.3 |
| 21 | 2-Nal | Val | Tyr | Cit | Lys | $^D$Pro$^L$Pro | 99 | 1114.3 |
| 22 | 2-Nal | Val | Tyr | Cit | Lys | $^D$Pro$^L$Pro | 100 | 1114.3 |
| 23 | 2-Nal | Val | Tyr | Cit | Lys | $^D$Pro$^L$Pro | 100 | 1138.1 |
| 24 | 2-Nal | Val | Tyr | Cit | Lys | $^D$Pro$^L$Pro | 100 | 1138.3 |
| 25 | 2-Nal | Val | Tyr | Cit | Lys | $^D$Pro$^L$Pro | 100 | 1119.3 |
| 26 | 2-Nal | Val | Tyr | Cit | Lys | $^D$Pro$^L$Pro | 100 | 1119.3 |
| 27 | 2-Nal | Phe | Tyr | Cit | Lys | $^D$Pro$^L$Pro | 100 | 1138.7 |
| 28 | 2-Nal | Phe | Tyr | Cit | Lys | $^D$Pro$^L$Pro | 100 | 1138.3 |
| 29 | 2-Nal | Phe | Tyr | Cit | Lys | $^D$Pro$^L$Pro | 100 | 1162.3 |
| 30 | 2-Nal | Phe | Tyr | Cit | Lys | $^D$Pro$^L$Pro | 100 | 1219.3 |
| 31 | 2-Nal | Phe | Tyr | Cit | Lys | $^D$Pro$^L$Pro | 100 | 1143.3 |
| 32 | 2-Nal | Phe | Tyr | Cit | Lys | $^D$Pro$^L$Pro | 100 | 1114.2 |
| 33 | 2-Nal | Phe | Tyr | Cit | Lys | $^D$Pro$^L$Pro | 100 | 1114.3 |
| 34 | 2-Nal | Phe | Tyr | Cit | Lys | $^D$Pro$^L$Pro | 100 | 1138.9 |
| 35 | 2-Nal | Phe | Tyr | Cit | Lys | $^D$Pro$^L$Pro | 100 | 1138.3 |
| 36 | 2-Nal | Phe | Tyr | Cit | Lys | $^D$Pro$^L$Pro | 100 | 1167.6 |
| 37 | 2-Nal | Phe | Tyr | Cit | Lys | $^D$Pro$^L$Pro | 100 | 1168.2 |
| 38 | 2-Nal | Phe | Tyr | Cit | Lys | $^D$Pro$^L$Pro | 100 | 1116.8 |
| 39 | 2-Nal | Phe | Tyr | Cit | Lys | $^D$Pro$^L$Pro | 100 | 1096.7 |
| 40 | 2-Nal | Phe | Tyr | Cit | Lys | $^D$Pro$^L$Pro | 92 | 1117.6 |
| 41 | 2-Nal | Tyr | Tyr | Cit | Lys | $^D$Pro$^L$Pro | 96 | 1153.8 |
| 42 | 2-Nal | Tyr | Tyr | Cit | Lys | $^D$Pro$^L$Pro | 100 | 1133.3 |
| 43 | 2-Nal | Tyr | Tyr | Cit | Lys | $^D$Pro$^L$Pro | 99 | 1134.0 |
| 44 | 2-Nal | Val | Tyr | Cit | Lys | $^D$Pro$^L$Pro | 93 | 1089.7 |
| 45 | 2-Nal | Val | Tyr | Cit | Lys | $^D$Pro$^L$Pro | 100 | 1068.5 |
| 46 | 2-Nal | Val | Tyr | Cit | Lys | $^D$Pro$^L$Pro | 95 | 1048.8 |
| 47 | 2-Nal | Val | Tyr | Cit | Lys | $^D$Pro$^L$Pro | 100 | 1070.3 |
| 48 | 2-Nal | t-BuG | Tyr | Cit | Lys | $^D$Pro$^L$Pro | 98 | 1103.6 |
| 49 | 2-Nal | t-BuG | Tyr | Cit | Lys | $^D$Pro$^L$Pro | 93 | 1062.4 |
| 50 | 2-Nal | t-BuG | Tyr | Cit | Lys | $^D$Pro$^L$Pro | 93 | 1084.3 |
| 51 | 2-Nal | Cys | Tyr | Cit | Lys | $^D$Pro$^L$Pro | 100 | 1071.7 |
| 52 | 2-Nal | Cys | Tyr | Cit | Lys | $^D$Pro$^L$Pro | 100 | 1051.6 |
| 53 | 2-Nal | Cys | Tyr | Cit | Lys | $^D$Pro$^L$Pro | 100 | 1073.2 |
| 54 | 2-Nal | Cys | Tyr | Gln | Lys | $^D$Pro$^L$Pro | 95 | 1061.4 |
| 55 | 2-Nal | Cys | Tyr | Gln | Lys | $^D$Pro$^L$Pro | 95 | 1072.9 |
| 56 | 2-Nal | Cys | Tyr | Gln | Lys | $^D$Pro$^L$Pro | 95 | 1030.3 |
| 57 | 2-Nal | Cys | Tyr | Arg | Lys | $^D$Pro$^L$Pro | 95 | 1071.8 |
| 58 | 2-Nal | Cys | Tyr | His | Lys | $^D$Pro$^L$Pro | 95 | 1061.9 |
| 59 | 2-Nal | Cys | Tyr | Tyr | Lys | $^D$Pro$^L$Pro | 95 | 1075.3 |
| 60 | 2-Nal | Cys | Tyr | Gln | Gln | $^D$Pro$^L$Pro | 95 | 1057.8 |
| 61 | 2-Nal | Cys | Tyr | Gln | Glu | $^D$Pro$^L$Pro | 95 | 1058.3 |
| 62 | 2-Nal | Cys | Tyr | Gln | Lys | $^D$Pro$^L$Pro | 95 | 1040.3 |
| 63 | 2-Nal | Cys | Tyr | Gln | Lys | $^D$Pro$^L$Pro | 95 | 1054.1 |
| 64 | 2-Nal | Cys | Tyr | Gln | Lys | $^D$Pro$^L$Pro | 95 | 1044.8 |
| 65 | 2-Nal | Cys | Tyr | Gln | Lys | $^D$Pro$^L$Pro | 95 | 1032.9 |
| 66 | 2-Nal | Cys | Tyr | Gln | Lys | $^D$Pro$^L$Pro | 95 | 1069.2 |
| 67 | 2-Nal | Cys | Tyr | Gln | Lys | $^D$Pro$^L$Pro | 95 | 1026.7 |
| 68 | 2-Nal | Cys | Tyr | Gln | Lys | $^D$Pro$^L$Pro | 95 | 1040.8 |
| 69 | 2-Nal | Cys | Tyr | Gln | Lys | $^D$Pro$^L$Pro | 95 | 1057.3 |
| 70 | 2-Nal | Cys | Tyr | Gln | Lys | $^D$Pro$^L$Pro | 95 | 1047.5 |
| 71 | 2-Nal | Cys | Tyr | Gln | Lys | $^D$Pro$^L$Pro | 95 | 1035.9 |
| 72 | 2-Nal | Cys | Tyr | Gln | Lys | $^D$Pro$^L$Pro | 95 | 1060.9 |
| 73 | 2-Nal | Cys | Tyr | Gln | Lys | $^D$Pro$^L$Pro | 95 | 1072.3 |
| 74 | 2-Nal | Cys | Tyr | Gln | Lys | $^D$Pro$^L$Pro | 95 | 1027.9 |
| 75 | 2-Nal | Cys | Tyr | Gln | Lys | $^D$Pro$^L$Pro | 95 | 1043.7 |

TABLE 2-continued

| Examples n = 14 | | | | | | | |
|---|---|---|---|---|---|---|---|
| 76 | 2-Nal | Cys | Tyr | Gln | Lys | $^D$Pro$^L$Pro | 95 | 1052.9 |
| 77 | 2-Nal | Cys | Tyr | Asn | Lys | $^D$Pro$^L$Pro | 95 | 1051.1 |
| 78 | 2-Nal | Cys | Tyr | Asp | Lys | $^D$Pro$^L$Pro | 95 | 1051.4 |
| 79 | 2-Nal | Cys | Tyr | Lys | Lys | $^D$Pro$^L$Pro | 95 | 1057.8 |
| 80 | 2-Nal | Cys | Tyr | Ala | Lys | $^D$Pro$^L$Pro | 95 | 1029.4 |
| 81 | 2-Nal | Cys | Tyr | Ser | Lys | $^D$Pro$^L$Pro | 95 | 1037.1 |
| 82 | 2-Nal | Cys | Tyr | Leu | Lys | $^D$Pro$^L$Pro | 95 | 1050.5 |
| 83 | 2-Nal | Cys | Tyr | Met | Lys | $^D$Pro$^L$Pro | 95 | 1058.9 |
| 84 | 2-Nal | Cys | Tyr | Gln | Asn | $^D$Pro$^L$Pro | 95 | 1051.0 |
| 85 | 2-Nal | Cys | Tyr | Gln | Asp | $^D$Pro$^L$Pro | 95 | 1051.4 |
| 86 | 2-Nal | Cys | Tyr | Gln | Ala | $^D$Pro$^L$Pro | 95 | 1028.9 |
| 87 | 2-Nal | Cys | Tyr | Gln | Ser | $^D$Pro$^L$Pro | 95 | 1037.3 |
| 88 | 2-Nal | Cys | Tyr | Gln | Lys | $^D$Pro$^L$Pro | 95 | 1034.1 |
| 89 | 2-Nal | Cys | Tyr | Gln | Lys | $^D$Pro$^L$Pro | 95 | 1019.8 |
| 90 | 2-Nal | Cys | Tyr | Gln | Lys | $^D$Pro$^L$Pro | 95 | 1025.8 |
| 91 | 2-Nal | Cys | Tyr | Gln | Lys | $^D$Pro$^L$Pro | 95 | 1041.3 |
| 92 | 2-Nal | Cys | Tyr | Gln | Lys | $^D$Pro$^L$Pro | 95 | 1036.2 |
| 93 | 2-Nal | Cys | Tyr | Gln | Lys | $^D$Pro$^L$Pro | 95 | 1036.8 |
| 94 | 2-Nal | Cys | Tyr | Gln | Lys | $^D$Pro$^L$Pro | 95 | 1043.3 |
| 95 | 2-Nal | Cys | Tyr | Gln | Lys | $^D$Pro$^L$Pro | 95 | 1014.8 |
| 96 | 2-Nal | Cys | Tyr | Gln | Lys | $^D$Pro$^L$Pro | 95 | 1022.8 |
| 97 | 2-Nal | Cys | Tyr | Gln | Lys | $^D$Pro$^L$Pro | 95 | 1035.9 |
| 98 | 2-Nal | Cys | Tyr | Gln | Lys | $^D$Pro$^L$Pro | 95 | 1028.9 |
| 99 | 2-Nal | Cys | Tyr | Gln | Lys | $^D$Pro$^L$Pro | 95 | 1052.9 |
| 100 | 2-Nal | Cys | Tyr | Gln | Lys | $^D$Pro$^L$Pro | 95 | 1044.9 |
| 101 | 2-Nal | Cys | Tyr | Gln | Lys | $^D$Pro$^L$Pro | 95 | 1023.3 |
| 102 | Trp | Cys | Tyr | Cit | Asp | $^D$Pro$^L$Pro | 95 | 1025.3 |
| 103 | 2-Nal | Cys | Tyr | Cit | Glu | $^D$Pro$^L$Pro | 95 | 1072.7 |
| 104 | 2-Nal | Cys | Tyr | Gln | Lys | $^D$Pro$^L$Pro | 95 | 1001.1 |
| 105 | Trp | Cys | Tyr | Cit | Lys | $^D$Pro$^L$Pro | 95 | 1056.4 |
| 106 | Trp | Cys | Tyr | Cit | Lys | $^D$Pro$^L$Pro | 95 | 1051.5 |
| 107 | Trp | Cys | Tyr | Cit | Lys | $^D$Pro$^L$Pro | 95 | 1057.5 |
| 108 | Trp | Cys | Tyr | Gln | Lys | $^D$Pro$^L$Pro | 95 | 1051.0 |
| 109 | Trp | Cys | Tyr | Gln | Lys | $^D$Pro$^L$Pro | 95 | 1023.0 |
| 110 | Trp | Cys | Tyr | Gln | Lys | $^D$Pro$^L$Pro | 95 | 995.0 |
| 111 | Trp | Cys | Tyr | Gln | Lys | $^D$Pro$^L$Pro | 95 | 1016.9 |
| 112 | Tyr | Cys | Tyr | Cit | Lys | $^D$Pro$^L$Pro | 95 | 1046.0 |
| 113 | Tyr | Cys | Cit | Tyr | Lys | $^D$Pro$^L$Pro | 83 | 1054.0 |
| 114 | 2-Nal | Cys | Tyr | Cit | Lys | $^D$Pro$^L$Pro | 95 | 1018.0 |
| 115 | 2-Nal | Cys | Tyr | Gln | Lys | $^D$Pro$^L$Pro | 95 | 1057.8 |
| 116 | Trp | Cys | Tyr | Cit | Lys | $^D$ProA8"-42 | 68 | 1153.1 |
| 117 | Trp | Cys | Tyr | Cit | Lys | $^D$Pro$^L$Pro | 90 | 1044.5 |
| 118 | Trp | Cys | Tyr | Gln | Lys | $^D$Pro$^L$Pro | 95 | 1019.0 |
| 119 | Trp | Cys | Tyr | Gln | Lys | $^D$Pro$^L$Pro | 90 | 1019.0 |
| 120 | Trp | Cys | Tyr | Gln | Lys | $^D$Pro$^L$Pro | 95 | 1013.5 |
| 121 | Trp | Cys | Tyr | Cit | Gln | $^D$Pro$^L$Pro | 95 | 1065.5 |
| 122 | Trp | Cys | Tyr | Cit | Lys | $^D$Pro$^L$Pro | 95 | 1070.0 |
| 123 | Trp | Cys | Tyr | Cit | Lys | $^D$Pro$^L$Pro | 95 | 1065.5 |
| 124 | 2-Nal | Cys | Tyr | Cit | Lys | $^D$Pro$^L$Pro | 95 | 1106.1 |
| 125 | 2-Nal | Cys | Tyr | Cit | Lys | $^D$Pro$^L$Pro | 95 | 1075.5 |
| 126 | 2-Nal | Cys | Tyr | Cit | Lys | $^D$Pro$^L$Pro | 95 | 1091.6 |
| 127 | 2-Nal | Cys | Tyr | Cit | NMeK | $^D$Pro$^L$Pro | 85 | 1078.1 |
| 128 | Trp | Cys | Tyr | Cit | Lys | $^D$Pro$^L$Pro | 93 | 1066.6 |
| 129 | 2-Nal | Cys | Tyr | NMeGly | Lys | $^D$Pro$^L$Pro | 89 | 1029.1 |
| 130 | 2-Nal | Cys | Tyr | Cit | Lys | $^D$Pro$^L$Pro | 79 | 1057.5 |
| 131 | 2-Nal | Cys | Tyr | Cit | Lys | $^D$Pro$^L$Pro | 98 | 1043.9 |
| 132 | 2-Nal | Cys | Tyr | Thr | Lys | $^D$Pro$^L$Pro | 89 | 1057.4 |
| 133 | 2-Nal | Cys | Tyr | Thr | Lys | $^D$Pro$^L$Pro | 90 | 1044.0 |
| 134 | 2-Nal | Cys | Tyr | Cit | Lys | $^D$Pro$^L$Pro | 88 | 1044.0 |
| 135 | 2-Nal | Cys | Tyr | Cit | Lys | $^D$Pro$^L$Pro | 95 | 1037.0 |
| 136 | Trp | Cys | Tyr | Cit | Lys | $^D$Pro$^L$Pro | 95 | 1066.0 |
| 137 | Trp | Cys | Tyr | Cit | Lys | $^D$Pro$^L$Pro | 95 | 1056.0 |
| 138 | 2-Nal | Cys | Tyr | Cit | Lys | $^D$Pro$^L$Pro | 76 | 1043.9 |
| 139 | 2-Nal | Cys | Tyr | Cit | Lys | $^D$Pro$^L$Pro | 90 | 1044.0 |
| 140 | 2-Nal | Cys | Tyr | Cit | Lys | $^D$Pro$^L$Pro | 88 | 1043.9 |
| 141 | 2-Nal | Cys | Tyr | Cit | Lys | $^D$Pro$^L$Pro | 95 | 1077.1 |
| 142 | Trp | Cys | Tyr | Cit | Lys | $^D$Pro$^L$Pro | 95 | 1117.6 |
| 143 | Trp | Cys | Tyr | Cit | Lys | $^D$Pro$^L$Pro | 95 | 1072.5 |
| 144 | 2-Nal | Cys | Tyr | Gln | Lys | $^D$Pro$^L$Pro | 87 | 1032.9 |
| 145 | Tyr | Cys | Tyr | Gln | Lys | $^D$Pro$^L$Pro | 95 | 1012.6 |
| 146 | Tyr | Cys | Tyr | Cit | Lys | $^D$Pro$^L$Pro | 95 | 1026.6 |
| 147 | Tyr | Cys | Tyr | Gln | Lys | $^D$Pro$^L$Pro | 92 | 1043.8 |
| 148 | Tyr | Cys | Tyr | Gln | Lys | $^D$Pro$^L$Pro | 91 | 1043.8 |
| 149 | Tyr | Cys | Tyr | Gln | Lys | $^D$Gln$^L$Pro | 91 | 1025.7 |
| 150 | Tyr | Arg | Cit | Cys | Arg | Gly$^D$Pro | 95 | 704.2 |
| 151 | Trp | Asn | Tyr | Cit | Lys | $^D$Pro$^L$Pro | 67 | 1065.0 |

TABLE 2-continued

Examples n = 14

| | | | | | | | | |
|---|---|---|---|---|---|---|---|---|
| 152 | Trp | Glu | Tyr | Cit | Lys | $^D$Pro$^L$Pro | 92 | 1070.3 |
| 153 | Trp | Dab | Tyr | Cit | Lys | $^D$Pro$^L$Pro | 72 | 1070.4 |

Cys in pos. 4 and 11 in Ex. 51-149 form a disulfide bridge, Cys in pos. 4 and 13 in Ex. 150 forms a disulfide bridge, Dab resp. Glu in pos. 4 and Glu resp Dab in position 11 in Ex. 152 resp. 153 form a lactame bridge,
$^{a)}$%-purity of compounds after prep. HPLC

TABLE 3

Examples n = 18

| Ex. | Sequ. ID | P1 | P2 | P3 | P4 | P5 | P6 | P7 | P8 | P9 |
|---|---|---|---|---|---|---|---|---|---|---|
| 154 | SEQ. ID NO 154 | Arg | Arg | 2-Nal | Cys | Tyr | Cit | Lys | Cys | Tyr |
| 155 | SEQ. ID NO 155 | Arg | Arg | Trp | Cys | Tyr | Gln | Lys | Cys | Tyr |
| 156 | SEQ. ID NO 156 | Arg | Arg | Trp | Cys | Tyr | Gln | Lys | Gly | Tyr |
| 157 | SEQ. ID NO 157 | Arg | Arg | Trp | Cys | Tyr | Gln | Lys | Gly | Tyr |
| 158 | SEQ. ID NO 158 | Arg | Arg | Trp | Cys | Tyr | Gln | Lys | Gly | Tyr |
| 159 | SEQ. ID NO 159 | Arg | Arg | Tyr | Cys | Tyr | Gln | Lys | Gly | Tyr |
| 160 | SEQ. ID NO 160 | Arg | Arg | Trp | Cys | Tyr | Arg | Lys | Cys | Tyr |

| Ex. | P10 | P11 | P12 | P13 | P14 | P15 | P16 | P17 | P18 | Template |
|---|---|---|---|---|---|---|---|---|---|---|
| 154 | Lys | Gly | Tyr | Cys | Tyr | Arg | Cit | Cys | Arg | Gly$^D$Pro |
| 155 | Lys | Gly | Tyr | Cys | Tyr | Arg | Cit | Cys | Arg | Gly$^D$Pro |
| 156 | Lys | Gly | Tyr | Gly | Tyr | Arg | Cit | Cys | Arg | Gly$^D$Pro |
| 157 | $^D$Lys | Gly | Tyr | Gly | Tyr | Arg | Cit | Cys | Arg | Gly$^D$Pro |
| 158 | $^D$Pro | Pro | Tyr | Gly | Tyr | Arg | Cit | Cys | Arg | Gly$^L$Pro |
| 159 | $^D$Pro | Pro | Tyr | Gly | Tyr | Arg | Thr | Cys | Arg | Gly$^L$Pro |
| 160 | Lys | Gly | Tyr | Cys | Tyr | Arg | Lys | Cys | Arg | Gly$^D$Pro |

Cys in pos. 4 and 17 and pos. 8 and 13 in Ex. 154-155 and 160 form a disulfide bridge, Cys in pos. 4 and 17 in Ex. 156-159 form a disulfide bridge 2. Biological Methods 2.1. Preparation of the Peptides.

Lyophilized peptides were weighed on a Microbalance (Mettler MT5) and dissolved in sterile water to a final concentration of 1 mM unless stated otherwise. Stock solutions were kept at +4° C., light protected.

2.2. Ca$^{2+-}$ Assay: CXCR4-Antagonizing Activity of the Peptides.

Method 1: 3-4Mio CXCR4 transfected pre-B cells [see references 1, 2 and 3, below] per measurement were resuspended in 200 μl MSB (20 mM 4-(2-Hydroxyethyl)-piperazin-1-ethanesulfonic acid (HEPES), 136 mM NaCl, 4.8 mM KCl and 1 mM CaCl$_2$) containing 5 mM D-Glucose and were loaded with 0.75 μl of 1 mM Fura-2-acetoxymethylester (Fura-2-AM) for 17 minutes at 37° C. The cells were washed free from Fura-2-AM with a platelet centrifuge and resuspended in 800 μl MSB containing 5 mM D-Glucose. The peptides to be administered were diluted to a 100 fold end concentration in MSB/0.2% PPL, and 8 pd were injected. [Ca$^{2+}$]$_i$-dependent fluorescence change in response to single or sequential stimulation with the peptide was recorded with a fluorimeter at an excitation wavelength of 340 nM and an end emission wavelength of 510 nM [see ref. 4, below]. Measurements were done under continuous stirring at 37° C. The signal intension was calibrated with 3 mM CaCl$_2$/1 mM Ionomycin (maximal fura-2-acetoxymethyester saturation) and 10 μM MnCl$_2$ (minimal Fura-2-acetoxymethylester saturation) and [Ca$^{2+}$]$_i$-changes are presented in % fura-2-acetoxymethylester saturation. The rate of [Ca$^{2+}$]$_i$-changes was calculated on the basis of the initial [Ca$^{2+}$]$_i$-changes and plotted in dependence of chemokine concentration to obtain a sigmoidal curve and to determine the IC$_{50}$ values.

MSB: 20 mM HEPES, 136 mM NaCl, 4.8 mM KCl, 1 mM CaCl$_2$.2H$_2$O, pH 7.4;

Osmolarity: 310 mOsm adjusted with NaOH or HCl, adjusted with H$_2$O or PBS.

MSB plus; 5 mM D-glucose in MSB (50 mg/50 mL).

Fura 2-acetoxymethylester: 1 mM stock solution in dimethulsulfoxide.

Method 2: Increases in intracellular calcium were monitored using a Flexstation 384 (Molecular Devices, Sunnyvale Calif.) to assay the peptides for CXCR4 antagonism in a mouse pre-B cell line 300-19 stably transfected with human CXCR4 [see references 1, 2 and 3, below]. The cells were batch loaded with the Calcium 3 Assay kit (Molecular Devices) in assay buffer (Hanks Balanced salt solution, HBSS, 20 mM HEPES, pH 7.4, 0.1% BSA) for 1 h at room temperature and then 200,000 labeled cells were dispensed into black 96 well assays plates (Costar No. 3603). A 20-fold concentrated solution of peptide in assay buffer was added to the cells and the whole plate was centrifuged to settle the cells to the bottom of the wells. Calcium mobilization induced by 10 nM stromal-derived factor-1 (SDF-1) was measured in the Flexstation 384 (excitation, 485 nM; emission, 525 nM) for 90 seconds. A maximal change in fluorescence response above baseline was used to calculate antagonist activity. The data for dose response curves (antagonist concentration versus % maximum response) were fitted to a four parameter logistic equation using SoftmaxPro 4.6 (Molecular Devices), from which IC$_5$, values were calculated.

2.3. FIGS-Assay™

The assay was performed according to ref. 5, below. Stock dilutions of the peptides (10 mM) were prepared by dissolving in 10 mM Tris-HCl at room temperature. Stock solutions were kept at +4° C., light protected. Working dilution were prepared extemporaneously by serial dilution in Phosphate Buffered Saline (PBS) and added in a final volume of 10 μl directly to the cell cultures. After 48 hours of co-cultivation the cultures were rinsed with PBS and then exposed to glutaraldehyde/formaldehyde (0.2%/2%) in PBS for five minutes. For photometric quantification the fixed cultures were subsequently incubated with ortho-nitro-phenyl-galactopyranoside (ONPG) as a β-galactosidase substrate, which was enzymatically converted into the chromophore ortho-nitrophenol (ONP). The read out is directly obtained by measuring optical density of wells at 405 nm in an iEMS 96 well-plate reader.

2.4. Cytotoxicity Assay

The cytotoxicity of the peptides to HELA cells (Acc57) and COS-7 cells (CRL-1651) was determined using the MTT reduction assay [see ref. 6 and 7, below]. Briefly the method was as follows: HELA cells and COS-7 cells were seeded at $7.0'10^3$ and, respectively, $4.5'10^3$ cells per well and grown in 96-well microtiter plates for 24 hours at 37° C. at 5% $CO_2$. At this point, time zero (Tz) was determined by MTT reduction (see below). The supernatant of the remaining wells was discarded, and fresh medium and the peptides in serial dilutions of 12.5, 25 and 50 μM were pipetted into the wells. Each peptide concentration was assayed in triplicate. Incubation of the cells was continued for 48 hours at 37° C. at 5% $CO_2$. Wells were then washed once with PBS and subsequently 100 μl MTT reagent (0.5 mg/mL in medium RPMI1640 and, respectively, DMEM) was added to the wells. This was incubated at 37° C. for 2 hours and subsequently the medium was aspirated and 100 μl isopropanol was added to each well. The absorbance at 595 nm of the solubilized product was measured ($OD_{595}$peptide). For each concentration averages were calculated from triplicates. The percentage of growth was calculated as follows: ($OD_{595}$peptide-$OD_{595}$Tz-$ODs_{595}$Empty well)/($OD_{595}$Tz-$OD_{595}$Empty well)×100% and was plotted for each peptide concentration.

The LC 50 values (Lethal. Concentration, defined as the concentration that kills 50% of the cells) were determined for each peptide by using the trend line function of EXCEL (Microsoft Office 2000) for the concentrations (50, 25, 12.5 and 0 μM), the corresponding growth percentages and the value −50, (=TREND(C50:C0,%50:%0,−50)). The GI 50 (Growth Inhibition) concentrations were calculated for each peptide by using a trend line function for the concentrations (50, 25, 12.5 and 0 μg/ml), the corresponding percentages and the value 50, (=TREND ($C_{50}:C_0$,%$_{50}$:%$_0$,50)).

2.5. Cell Culture

'CCR5' cells were cultured in DMEM medium with 4500 mg/ml glucose, 10% fetal bovine serum (FBS), supplemented with 50 U/ml Penicillin and 50 Ag/ml Streptomycin (Pen/Strept.). Hut/4-3 cells were maintained in RPMI medium, 10% FBS, supplemented with Pen/Strept. and 10 mM HEPES. HELA cells and CCRF-CEM cells were maintained in RPM 11640 plus 5% FBS, Pen/Strept and 2 mM L-Glutamine. Cos-7 cells were grown in DMEM medium with 4500 mg/ml glucose supplemented with 10% FCS, Pen/Strept. and 2 mM L-Glutamine. All cell lines were grown at 37° C. at 5% $CO_2$. Cell media, media supplements, PBS-buffer, HEPES, Pen/Strept, L-Glutamine and sera were purchased from Gibco (Pailsey. UK). All fine chemicals came from Merck (Darmstadt, Germany).

2.6. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 μM were incubated with 20% v/v hRBC for 1 hour at 37° C. The final erythrocyte concentration was approximately $0.9 \times 10^9$ cells per ml. A value of 0% resp. 100% cell lysis was determined by incubation of the hRBC in the presence of PBS alone and respectively 0.1% Triton X-100 in $H_2O$. The samples were centrifuged and the supernatant was 20-fold diluted in PBS buffer and the optical density (OD) of the sample at 540 nM was measured. The 100% lyses value ($OD_{540}H_2O$) gave an $OD_{540}$ of approximately 1.3-1.8. Percent hemolysis was calculated as follows: ($OD_{540}$peptide/$OD_{540}H_2O$)×100%.

2.7. Chemotactic Assay (Cell Migration Assay)

The chemotactic response of CCRF-CEM cells to a gradient of stromal cell-derived factor 1α SDF-1) was measured using disposable assay plates from Neuroprobe (5 ppore size) (Gaithersburg, Md.), according to the manufacturer's directions and references therein [especially ref. 8, below]. Briefly, one 175 $cm^2$ flask was washed once with Dubecco's phosphate buffered saline (DPBS), and trypsinized for 10 minutes or until cells had lifted. The trypsin was neutralized by the addition of fresh medium containing serum and the cells were pelleted, washed once in DPBS, and resuspended at $1-0.5 \times 10^7$ cells/ml in RPMI+ 0.5% bovine serum albumin (BSA). 45 μl of cell suspension were mixed with 5 μl of 10-fold concentrated PEM peptide diluted in the same assay medium. 35 μl of this mixture were applied to the top of the assay filter. The cells were allowed to migrate (at 370) into the bottom chamber of the assay plate containing 1 nM SDF-1. After 4 hours, the filter was removed and MTT was added to the migrated cells to a final concentration of 0.5 mg/ml, and incubated for a further 4 hours. After labeling with MTT, all medium was removed and 100 μl of isopropanol+10 mM HCl were added to the cells. The optical absorbance at 595 nm ($ABS_{595}$) was read using a Tecan Genios plate reader with Magellan software. The number of cells migrated was determined by comparing $ABS_{595}$ values against a standard curve generated with a known number of cells in the assay plate and were plotted against SDF-1 concentration to obtain a sigmoidal curve and to determine the $IC_{50}$ values. The values for IC50 were determined using the Trendline function in Microsoft Excel by fitting a logarithmic curve to the averaged datapoints.

2.8 Plasmastability

405 μl of plasma/albumin solution were placed in a polypropylene (PP) tube and spiked with 45 μl of compound from a 100 μM solution B, derived from 135 μl of PBS and 15 μl of 1 mM peptide in PBS, pH 7.4. 150 μl aliquots were transferred into individual wells of the 10 kDa filter plate (Millipore MAPPB 1010 Biomax membrane). For "0 minutes controls": 270 μl of PBS were placed in a PP tube and 30 μl of stock solution B was added and vortexed. 150 μl of control solution was placed into one well of the filter plate and serves as "filtered control". Further 150 μl of control solution were placed directly into a receiver well (reserved for filtrate) and serve as "not-filtered control". The entire plate including evaporation lid was incubated for 60 min at 37° C. Plasma samples (rat plasma: Harlan Sera lab UK, human plasma: Blutspendezentrum Züirich) were centrifuged at least for 2 h at 4300 rpm (3500 g) and 15° C. in order to yield 100 μl filtrate. For "serum albumin"-samples (freshly prepared human albumin: Sigma A-4327, rat albumin: Sigma A-6272, all at 40 mg/ml concentration in PBS) approximately 1 hour of centrifugation is sufficient. The filtrates in the receiver PP plate were analysed by LC/MS as follows: Column: Jupiter C18 (Phenomenex), mobile phases: (A) 0.1% formic acid in water and (B) acetonitrile, gradient: 5%-100% (B) in 2 minutes, electrospray ionization, MRM detection (triple quadrupole). The peak areas were determined and triplicate values are averaged. The binding is expressed in percent of the (filtered and not-filtered time point 0 min) control 1 and 2 by: $100-(100*T_{60}/T_0)$. The average from these values is then calculated (see ref. 9 below).

2.9. Pharmacokinetic Study (PK)

Pharmacokinetic study after single intravenous (i.v.) and intraperitoneal (i.p.) administration was performed for the compound of Example 51 ("Ex. 51"). 30 grams (±20%) male CD-1 mice obtained from Charles River Laboratories Deutschland GmbH were used in the study. The vehicle, physiological saline, was added to give a final concentration of 1 mg/ml of the compounds. The volume was 2 ml/kg i.v. and 10 ml/kg i.p and the peptide Ex. 51 was injected to give a final intraperitoneal dose of 10 mg/kg and an intravenous dose of 2 mg/kg. Approximately 250-300 µl of blood was removed under light isoflurane anesthesia from the retro-orbital plexus at predetermined time intervals (0, 5, 15, 30 min and 1, 2 and 3 hours for the i.v. study and 0, 15, 30 min and 1, 2, 4 and 8 hours for the i.p. study) and added to heparinized tubes. Plasma was removed from pelleted cells upon centrifugation and frozen at −80° C. prior to HPLC-MS analysis.

Preparation of the Plasma Calibration Samples "Blank" mouse plasma from untreated animals was used. Aliquots of plasma of 0.2 ml each were spiked with 50 ng of propranolol (Internal Standard, IS), (sample preparation by solid phase extraction on OASIS® HLB cartridges (Waters)) and with known amounts of Ex. 51 in order to obtain 9 plasma calibration samples in the range 10-5000 nM. The OASIS® HLB cartridges were conditioned with 1 ml of methanol and then with 1 ml of 1% $NH_3$ in water. Samples were then diluted with 700 µl of 1% $NH_3$ in water and loaded.

The plate was washed with 1 ml of methanol/1% $NH_3$ in water 5/95. Elution was performed using 1 ml of 0.1% TFA in methanol.

The plate containing eluates was introduced into the concentrator system and taken to dryness.

The residues were dissolved in 100 µL of formic acid 0.1%/acetonitrile, 95/5 (v/v) and analysed in the HPLC/MS on a reverse phase analytical column (Jupiter C 18, 50×2.0 mm, 5 µm, Phenomenex), using gradient elution (mobile phases A: 0.1% formic acid in water, B: Acetonitrile; from 5% B to 100% B in 2 min.).

Preparation of Plasma Samples

Samples coming from animal treatments were pooled in order to obtain an appropriate volume for the extraction. If the total volume obtained was less than 0.2 ml the appropriate amount of "blank" mouse plasma was added in order to keep the matrix identical to the calibration curve. Samples were than spiked with IS and processed as described for the calibration curve.

Pharmacokinetic Evaluation

PK analysis was performed on pooled data (generally n=2 or 3) using the software PK solutions 2.0™ (Summit Research Service, Montrose, Colo. 81401 USA). The area under the curve AUC was calculated by the linear trapezoidal rule. $AUC_{(t-\infty)}$ was estimated as Ct/b (b: elimination rate constant). $AUC_{(t-\infty)}$ is the sum of $AUC_{(0-t)}$ and $AUC_{(t-\infty)}$. Elimination half-life was calculated by the linear regression on at least three data points during the elimination phase. The time intervals selected for the half-life determinations were evaluated by the correlation coefficient ($r^2$), which should be at least above 0.85 and most optimally above 0.96. In case of i.v. administration the initial concentration at $t_{zero}$ was determined by extrapolation of the curve through the first two time points. Finally bioavailability after i.p. administration was calculated from the normalised $AUC_{(0-\infty)}$ ration after i.p. versus i.v. administration.

3.0. Results

The results of the experiments described under 2.2-2.7, above, are indicated in Table 4 herein below.

TABLE 4

| Ex. | $IC_{50}$ (nM) $Ca^{2+}$ assay | FIGS ™ % inhibition at 200 nM | FIGS ™ St. dev. at 200 nM | Cytotoxicity $LC_{50}/GI_{50}$ Hela cells | Hemolysis at 100 µM | $IC_{50}$ (µM) Cell migration assay |
|---|---|---|---|---|---|---|
| 1 | 2280 | n.d. | n.d. | 82 | 1.6 | n.d. |
| 2 | 2830 | n.d. | n.d. | 97 | 0.9 | n.d. |
| 3 | 1000 | n.d. | n.d. | 126 | 1.7 | n.d. |
| 4 | 2540 | n.d. | n.d. | 191 | 0.7 | n.d. |
| 6 | 1930 | n.d. | n.d. | 103 | 0.6 | n.d. |
| 20 | 3730 | n.d. | n.d. | 85 | 0.2 | n.d. |
| 21 | 550 | n.d. | n.d. | 114 | 0.6 | n.d. |
| 22 | 300 | n.d. | n.d. | 139 | 0.0 | n.d. |
| 23 | 1550 | n.d. | n.d. | 49 | 1.4 | n.d. |
| 24 | 850 | n.d. | n.d. | 108 | 0.7 | n.d. |
| 25 | 1000 | n.d. | n.d. | 108 | 0.0 | n.d. |
| 28 | 2680 | n.d. | n.d. | 117 | 0.9 | n.d. |
| 31 | 1470 | n.d. | n.d. | 82 | 0.1 | n.d. |
| 32 | 760 | n.d. | n.d. | 85 | 0.5 | n.d. |
| 38 | 719.7 | n.d. | n.d. | 348 | 0.3 | n.d. |
| 45 | n.d. | 65.1 | 4.8 | 132 | 0.4 | n.d. |
| 51 | 1.9 | 93.9 | 1.0 | 97 | 0.0 | 0.275 |
| 52 | 3.1 | 95.4 | 1.3 | 99 | 0.0 | 2.75 |
| 53 | 57.8 | 91.8 | 1.6 | 86 | 0.2 | n.d. |
| 54 | 6.9 | n.d. | n.d. | 54 | 0.0 | n.d. |
| 55 | 6.3 | n.d. | n.d. | 43 | 0.1 | n.d. |
| 56 | 0.74 | n.d. | n.d. | 60 | — | n.d. |
| 57 | 4.2 | n.d. | n.d. | 33 | 0.1 | n.d. |
| 58 | 10.5 | n.d. | n.d. | 18 | 0.0 | n.d. |
| 59 | 7.8 | n.d. | n.d. | 33 | 0.1 | n.d. |
| 60 | 0.18 | n.d. | n.d. | 62 | 0.1 | n.d. |

TABLE 4-continued

| Ex. | IC$_{50}$ (nM) Ca$^{2+}$ assay | FIGS™ % inhibition at 200 nM | FIGS™ St. dev. at 200 nM | Cytotoxicity GI$_{50}$ Hela cells | Hemolysis at 100 μM | IC$_{50}$ (μM) Cell migration assay |
|---|---|---|---|---|---|---|
| 61 | 4.1 | n.d. | n.d. | >100 | 0.3 | n.d. |
| 62 | 1.8 | n.d. | n.d. | 65 | 0.1 | n.d. |
| 63 | 2.0 | n.d. | n.d. | 58 | 0.2 | n.d. |
| 64 | 3.3 | n.d. | n.d. | 66 | 0.3 | n.d. |
| 65 | 3.9 | n.d. | n.d. | 65 | 0.2 | n.d. |
| 66 | 3.8 | n.d. | n.d. | 46 | 0.0 | n.d. |
| 67 | 2.4 | n.d. | n.d. | 49 | 0.2 | n.d. |
| 68 | 1.1 | n.d. | n.d. | >100 | 0.1 | n.d. |
| 69 | 1.8 | n.d. | n.d. | 49 | 0.1 | n.d. |
| 70 | 19.5 | n.d. | n.d. | 40 | 0.2 | n.d. |
| 71 | 2.7 | n.d. | n.d. | 34 | 0.1 | n.d. |
| 72 | 3.9 | n.d. | n.d. | 36 | 0.5 | n.d. |
| 73 | 8.8 | n.d. | n.d. | 20 | 0.3 | n.d. |
| 74 | 19.5 | n.d. | n.d. | 40 | 0.4 | n.d. |
| 75 | 3.5 | n.d. | n.d. | >100 | 0.0 | n.d. |
| 76 | 5.6 | n.d. | n.d. | >100 | 0.1 | n.d. |
| 77 | 7 | n.d. | n.d. | >100 | 0.2 | n.d. |
| 78 | 11 | n.d. | n.d. | 69 | 0.1 | n.d. |
| 79 | 2.4 | n.d. | n.d. | 94 | 0.0 | n.d. |
| 80 | 2.9 | n.d. | n.d. | 44 | 0.1 | n.d. |
| 81 | 4.9 | n.d. | n.d. | 45 | 0.0 | n.d. |
| 82 | 4.8 | n.d. | n.d. | 40 | 0.0 | n.d. |
| 83 | 3.7 | n.d. | n.d. | 48 | 0.1 | n.d. |
| 84 | 3.9 | n.d. | n.d. | 62 | 0.0 | n.d. |
| 85 | 2.7 | n.d. | n.d. | 94 | 0.0 | n.d. |
| 86 | 0.69 | n.d. | n.d. | 62 | 0.0 | n.d. |
| 87 | 3.5 | n.d. | n.d. | 64 | 0.0 | n.d. |
| 88 | 2.5 | n.d. | n.d. | 44 | 0.0 | n.d. |
| 89 | 0.5 | n.d. | n.d. | 50 | 0.0 | n.d. |
| 90 | 19.5 | n.d. | n.d. | 57 | 0.1 | n.d. |
| 91 | 2.1 | n.d. | n.d. | 48 | 0.2 | n.d. |
| 92 | 1.1 | n.d. | n.d. | 53 | 0.5 | n.d. |
| 93 | 4.3 | n.d. | n.d. | >100 | 0.2 | n.d. |
| 94 | 2.5 | n.d. | n.d. | 45 | 0.2 | n.d. |
| 95 | 2.9 | n.d. | n.d. | 41 | 0.1 | n.d. |
| 96 | 3.0 | n.d. | n.d. | 69 | 1.0 | n.d. |
| 97 | 4.3 | n.d. | n.d. | 44 | 0.8 | n.d. |
| 98 | 3.9 | n.d. | n.d. | 41 | 1.0 | n.d. |
| 99 | 4.2 | n.d. | n.d. | 40 | 1.1 | n.d. |
| 100 | 7.0 | n.d. | n.d. | 43 | 0.8 | n.d. |
| 101 | 1.28 | n.d. | n.d. | 74 | 0.6 | n.d. |
| 102 | 8.0 | n.d. | n.d. | 33 | 0.5 | n.d. |
| 103 | 18.3 | n.d. | n.d. | 42 | 0.2 | n.d. |
| 104 | 7.4 | n.d. | n.d. | 71 | 0.0 | n.d. |
| 105 | 0.62 | n.d. | n.d. | 49 | 0.0 | n.d. |
| 106 | 3.1 | n.d. | n.d. | 83 | 0.0 | n.d. |
| 107 | 3.8 | n.d. | n.d. | 50 | 0.4 | n.d. |
| 108 | 4.6 | n.d. | n.d. | 70 | 0.0 | n.d. |
| 109 | 3.0 | n.d. | n.d. | 65 | 0.0 | n.d. |
| 110 | 1.7 | n.d. | n.d. | 48 | 0.0 | n.d. |
| 111 | 1.6 | n.d. | n.d. | >100 | 0.0 | n.d. |
| 112 | 7.8 | n.d. | n.d. | 76 | 0.0 | n.d. |
| 113 | 0.62 | n.d. | n.d. | 45 | 0.0 | n.d. |
| 114 | 1.3 | n.d. | n.d. | 67 | 0.0 | n.d. |
| 115 | 2.7 | n.d. | n.d. | >100 | 0.1 | n.d. |
| 116 | 14.5 | n.d. | n.d. | 20 | 0.0 | n.d. |
| 117 | 3.4 | n.d. | n.d. | 44 | 0.0 | n.d. |
| 118 | 7.6 | n.d. | n.d. | 52 | 0.0 | n.d. |
| 119 | 9.4 | n.d. | n.d. | 63 | 0.0 | n.d. |
| 120 | 8.1 | n.d. | n.d. | 78 | 0.0 | n.d. |
| 121 | 6.5 | n.d. | n.d. | 79 | 0.0 | n.d. |
| 122 | 8.8 | n.d. | n.d. | 60 | 0.0 | n.d. |
| 123 | 10.0 | n.d. | n.d. | 80 | 0.0 | n.d. |
| 124 | 5.9 | n.d. | n.d. | 21 | 0.0 | n.d. |
| 125 | 330.0 | n.d. | n.d. | >100 | 0.0 | n.d. |
| 126 | 19.5 | n.d. | n.d. | 85 | 0.0 | n.d. |
| 127 | 52.2 | n.d. | n.d. | 62 | 0.0 | n.d. |
| 128 | 4.5 | n.d. | n.d. | 43 | 0.0 | n.d. |
| 129 | 10.9 | n.d. | n.d. | 23 | 0.0 | n.d. |
| 130 | 4.1 | n.d. | n.d. | 62 | 0.0 | n.d. |
| 131 | 2.4 | n.d. | n.d. | 53 | 0.0 | n.d. |
| 132 | 1.9 | n.d. | n.d. | 76 | 0.0 | n.d. |
| 133 | 5.3 | n.d. | n.d. | 45 | 0.1 | n.d. |

TABLE 4-continued

| | | | | | | |
|---|---|---|---|---|---|---|
| 134 | 1.7 | n.d. | n.d. | 21 | 0.0 | n.d. |
| 135 | 4.7 | n.d. | n.d. | 30 | 0.1 | n.d. |
| 136 | 4.1 | n.d. | n.d. | >100 | 0.0 | n.d. |
| 137 | 1.28 | n.d. | n.d. | 79 | 0.5 | n.d. |
| 138 | 63.0 | n.d. | n.d. | 18 | 0.0 | n.d. |
| 140 | 19.6 | n.d. | n.d. | 35 | 0.0 | n.d. |
| 141 | >10 | n.d. | n.d. | 18 | n.d. | n.d. |
| 142 | 96.9 | n.d. | n.d. | n.d. | n.d. | n.d. |
| 143 | 0.9 | n.d. | n.d. | 46 | n.d. | n.d. |
| 144 | 0.18 | n.d. | n.d. | n.d. | n.d. | n.d. |
| 145 | 0.38 | n.d. | n.d. | 97 | 0.0 | n.d. |
| 146 | 0.24 | n.d. | n.d. | n.d. | n.d. | n.d. |
| 147 | 0.17 | n.d. | n.d. | n.d. | n.d. | n.d. |
| 148 | 0.65 | n.d. | n.d. | 46 | 71 | n.d. |
| 149 | 1.0 | n.d. | n.d. | >100 | 0.0 | n.d. |
| 150 | 1.4 | n.d. | n.d. | n.d. | n.d. | n.d. |
| 151 | 4.2 | n.d. | n.d. | 83 | 0.9 | n.d. |
| 152 | 4.2 | n.d. | n.d. | 46 | 0.0 | n.d. |
| 153 | 21.9 | n.d. | n.d. | 43 | 1.7 | n.d. |
| 154 | 9.3 | n.d. | n.d. | n.d. | n.d. | n.d. |
| 155 | 0.46 | n.d. | n.d. | n.d. | n.d. | n.d. |
| 156 | 49 | n.d. | n.d. | n.d. | n.d. | n.d. |
| 157 | 11.3 | n.d. | n.d. | n.d. | n.d. | n.d. |
| 158 | 250 | n.d. | n.d. | n.d. | n.d. | n.d. |
| 159 | 118 | n.d. | n.d. | n.d. | n.d. | n.d. |
| 160 | 0.38 | n.d. | n.d. | n.d. | n.d. | n.d. | n.d.: not determined

The determination of IC50 (nM) values in the Ca2+ assay for Ex. 1-53 was performed using method 1, for Ex. 54-155 method 2 was used. For the determination of cytotoxicity values in Ex. 1-53 the LC50 calculation was used, for Ex. 52-160 the GI50 calculation was used.

The determination of IC50 (nM) values in the Ca2+ assay for Ex. 1-53 was performed using method 1, for Ex. 54-160 method 2 was used.

The results of the experiment described in 2.8, above, are indicated in Table 5 herein below.

TABLE 5

| Ex. | Stability human Plasma $t_{1/2}$ (min) | Stability rat Plasma $t_{1/2}$ (min) |
|---|---|---|
| 51 | 286 | >300 |
| 60 | >300 | >300 |
| 61 | 273 | >300 |
| 68 | 127 | 81 |
| 75 | 188 | 142 |
| 85 | 166 | >300 |
| 101 | >300 | 247 |
| 102 | 255 | 245 |
| 110 | 115 | 259 |
| 124 | >300 | >300 |
| 120 | 39 | 174 |
| 151 | 89 | 71 |
| 152 | 23 | 86 |

The results of the experiment described in 2.9 (PK), above, are indicated in Tables 6, 7 and 8 herein below.

TABLE 6

Route i.v.
Dose 2 mg/kg

| Time (h.) | Calc. Conc (ng/ml) | n. of animals pooled |
|---|---|---|
| 0.083 | 1461 | 3 |
| 0.25 | 328 | 2 |
| 0.5 | 300 | 3 |
| 1 | 80 | 3 |
| 2 | 68 | 3 |
| 3 | 49 | 3 |

TABLE 7

Route i.p.
Dose 10 mg/kg

| Time (h.) | Calc. Conc (ng/ml) | n. of animals pooled |
|---|---|---|
| 0.25 | 673 | 3 |
| 0.5 | 1568 | 2 |
| 1 | 2009 | 2 |
| 2 | 3160 | 2 |
| 4 | 1024 | 3 |
| 8 | 519 | 3 |

TABLE 8

| Administration route | Intravenous | Intraperitoneal |
|---|---|---|
| Dose (mg/kg) | 2 | 10 |
| $AUC_{0-t}$ (ng · h/ml) | 1704 | 11112 |
| $AUC_{0-inf.}$ (ng · h/ml) | 1905 | 12948 |
| $AUC_{norm.}$ (ng · h/ml) | 953 | 1295 |
| $C_{max}$ ng/ml | 28594 | 3160 |
| $C_{max\ norm.}$ | 14297 | 316 |
| $T_{max}$ (hour) | 0 | 2 |
| β (hours$^{-1}$) | 0.24 | 0.28 |
| Half-life (hours) | 2.8 | 2.5 |
| % absorbed (F) (percentage of normalized $AUC_{0-inf.}$ intraperitoneal against normalized $AUC_{0-inf}$ i.v.) | 100 | 136 |

After intravenous administration of Ex. 51 at a dose level of 2 mg/kg body weight. Ex. 51 followed intravenous kinetic characteristics. After PK analysis, Ex. 51 showed an extrapolated $C_{initial}$ of 28594 ng/ml and a $C_{max}$ observed of 1461 ng/ml at 5 min. Plasma levels rapidly decreased to 328 and 80 ng/ml at 15 min and 1 hour respectively. From 1 to 3 h plasma levels decreased with an elimination half-life of 2.8 h to 49 ng/ml at 3 h.

The $AUC_{(0-t)}$ and $AUC_{(0-\infty)}$ amounted to 1704 and 1905 ng·h/ml, respectively. After intraperitoneal administration of Ex. 51 at a dose level of 10 mg/kg body weight, plasma levels of Ex. 51 increased almost linearly within the first 2 h and showed a $C_{max}$ of 3160 ng/ml at 2 hours. From 2 to 8 h plasma levels decreased with an elimination half-life of 2.5 h to 519 ng/ml at 8 h. The $AUC_{(0-t)}$ and $AUC_{(0-\infty)}$ amounted to 11112 and 12948 ng·h/ml, respectively. As compared to the normalized AUC value after i.v. administration (100% absorbed, 953 ng·h/ml) of Ex. 51 absorbed after i.p. administration amounted to 136% (1295 ng·h/ml) at an 45 times lower normalised Cmaxafter i.p. administration (316 versus 1497 ng/ml). The value above 100% may partially reflect an impaired reliability caused by the limited number of points.

REFERENCES

1. Oberlin E, Amara A, Bachelerie F, Bessia C, Virelizier J-L, Arenzana-Seisdedos F, Schwartz O, Heard J-M, Clark-Lewis I, Legler D. F., Loetscher M, Baggiolini M, Moser B. *Nature,* 1996, 382:833-835
2. Loetscher M, Geiser T, O'Reilly T, Zwalen R, Baggiolini M, Moser B. *J. Biol. Chem.* 1994. 269:232-237
3. D'Apuuo M, Rolink A, Loetscher M, Hoxie J. A., Clark-Lewis I. Melchors F, Baggiolini M, Moser B. *Eur. J. Immunol.* 1997. 27:1788-1793
4. von Tscharner V, Prod'hom B, Baggiolini M, Reuter H. *Nature.* 1986. 324:369-72.
5. Hamy F, Felder E. R., Heizmann G, Lazdins J, Aboul-ela F, Varani G, Karn J, Klimkait T. *Proc. Natl. Acad. Sci.* 1997. 94:3548-3553.
6. Mossman T. *J. Immunol. Meth.* 1983, 65:55-63
7. Berridge M. V., Tan A. S. *Arch. Biochem. Biophys.* 1993, 303:474-482
8. Frevert C. W., Wong V. A., Goodman R. V., Goodwin R, Martin T. R., *J. Immunol. Meth.* 1998.213: 41-52
9. Singh R., Chang, S. Y., Talor, L. C., *Rapid Commun. Mass Spectrom.,* 1996, 10: 1019-1026

---

The invention claimed is:
1. A compound of the general formula

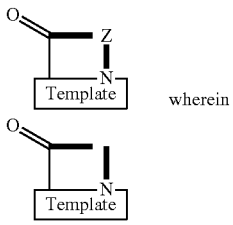

wherein is a dipeptide residue made up of two different amino acid building blocks, the dipeptide being $^D$Pro-$^L$Pro; and
Z is a chain made up of 12 α-amino acid residues, in which
the P1 residue is the residue of Tyr;
the P2 residue is the residue of Arg or Gly;
the P3 residue is the residue of Cit;
the P4 residue is the residue of Val, Phe, Cys, Gly, Ile, Thr or Gln;
the P5 residue is the residue of Arg;
the P6 residue is the residue of $^D$Arg or Arg;
the P7 residue is the residue of Arg;
the P8 residue is the residue of 2-Nal or Trp;
the P9 residue is the residue of Phe, Val, Cys, Gly, Ile, Thr or Gln;
the P10 residue is the residue of Tyr;
the P11 residue is the residue of Cit or Gly;
the P12 residue is the residue of Lys;
when P4 and P9 are both cysteine, a disulfide bridge is present between the two side chains thereof; or an enantiomer of said compound,
or a pharmaceutically acceptable salt of said compound.

2. A An enantiomer of a compound of claim 1.

3. A compound according to claim 1 having CXCR4 antagonizing activity, which also has anticancer activity and/or anti-inflammatory activity, wherein the cancer is selected from the group consisting of breast cancer, brain cancer, prostate cancer, lung cancer, kidney cancer, neuroblastoma, non-hodgkin's lymphoma, ovarian cancer, multiple myeloma, chronic lymphocytic leukemia, pancreatic cancer, melanoma, and whereas the inflammatory activity is selected from the group consisting of asthma, allergic rhinitis, hypersensitivity lung diseases, hypersensitivity pneumonitis, eosinophilic pneumonias, delayed-type hypersensitivity, interstitial lung disease (ILD), idiopathic pulmonary fibrosis, ILD associated with rheumatoid arthritis, systemic lupus erythematosus, ankylosing sponylitis, systemic sclerosis, Sjogren's syndrome, systemic anaphylaxis or hypersensitivity responses, drug allergies, rheumatoid arthritis, psoriatic arthritis, systemic lupus erythematosus, myasthenia gravis, juvenile onset diabetes, glomerulonephritis, autoimmune thyroiditis, graft rejection including allograft rejection or graft-versus-host disease, inflammatory bowel diseases and inflammatory dermatoses.

4. A pharmaceutical composition containing a compound according to claim 1 and a pharmaceutically inert carrier.

5. A composition according to claim 4 in a form suitable for oral, topical, transdermal, injection, buccal, transmucosal, pulmonary or inhalation administration.

6. A composition according to claim 4 in form of tablets, dragees, capsules, solutions, liquids, gels, plaster, creams, ointments, syrup, slurries, suspensions, spray, nebuliser or suppositories.

7. A method of antagonizing CXCR4 in a patient in need thereof, comprising administering to the patient an effective amount of a compound according to claim 1.

8. The method according to claim 7 wherein said antagonism of CXCR4 is intended to be for slowing viral progression in infected patients.

9. A process for the manufacture of a compound according to claim 1 which process comprises
(a) coupling an appropriately functionalized solid support with an appropriately N-protected derivative of that amino acid which in the end-product is in position 8, 9 or 10, any functional group which may be present in said N-protected amino acid derivative being likewise appropriately protected;
(b) removing the N-protecting group from the product thus obtained;
(c) coupling the product thus obtained with an appropriately N-protected derivative of that amino acid which is one position nearer the N-terminal amino acid residue, any functional group which may be present in said N-protected amino acid derivative being likewise appropriately protected;
(d) removing the N-protecting group from the product thus obtained;
(e) repeating steps (c) and (d) until the N-terminal amino acid residue has been introduced;
(f) coupling the product thus obtained with a compound of the general formula

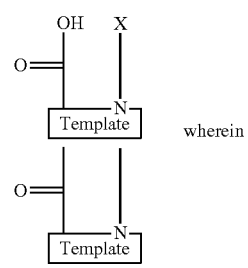

wherein is as defined in claim 1 and X is an N-protecting group
(g) removing the N-protecting group from the product obtained in step (f);
(h) coupling the product thus obtained with an appropriately N-protected derivative of that amino acid which is in position 12, any functional group which may be present in said N-protected amino acid derivative being likewise appropriately protected;
(i) removing the N-protecting group from the product thus obtained;
(j) coupling the product thus obtained with an appropriately N-protected derivative of that amino acid which is one position farther away from position 12, any functional group which may be present in said N-protected amino acid derivative being likewise appropriately protected;
(k) removing the N-protecting group from the product thus obtained;
(l) repeating steps (j) and (k) until all amino acid residues have been introduced;
(m) optionally, selectively deprotecting one or several protected functional group(s) present in the molecule and appropriately substituting the reactive group(s) thus liberated;

(n) optionally, forming one, two or three interstrand linkage(s) between side-chains of appropriate amino acid residues at opposite positions of the chain of 12 α-amino acid residues;
(o) detaching the product thus obtained from the solid support;
(p) cyclizing the product cleaved from the solid support;
(q) removing any protecting groups present on functional groups of any members of the chain of amino acid residues and, optionally, any protecting group(s) which may in addition be present in the molecule; and
(r) optionally converting the product thus obtained into a pharmaceutically acceptable salt or converting a pharmaceutically acceptable, or unacceptable, salt thus obtained into the corresponding free compound of formula I or into a different, pharmaceutically acceptable, salt.

10. A process for the manufacture of a compound according to claim 1 which process comprises
(a') coupling an appropriately functionalized solid support with a compound of the general formula

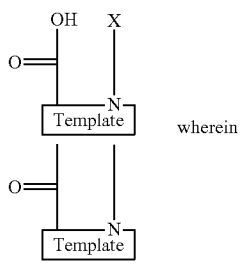 wherein

II is as defined above and X is an N-protecting group
(b') removing the N-protecting group from the product obtained in step (a');
(c') coupling the product thus obtained with an appropriately N-protected derivative of that amino acid is in position 12, any functional group which may be present in said N-protected amino acid derivative being likewise appropriately protected;
(d') removing the N-protecting group from the product thus obtained;
(e') coupling the product thus obtained with an appropriately N-protected derivative of that amino acid which is one position farther away from position 12, any functional group which may be present in said N-protected amino acid derivative being likewise appropriately protected;
(f') removing the N-protecting group from the product thus obtained;
(g') repeating steps (e') and (f') until all amino acid residues have been introduced;
(h') optionally, selectively deprotecting one or several protected functional group(s) present in the molecule and appropriately substituting the reactive group(s) thus liberated;
(i') optionally, forming one, two or three interstrand linkage(s) between side-chains of appropriate amino acid residues at opposite positions of the chain of 12 α-amino acid residues;
(j') detaching the product thus obtained from the solid support;
(k') cyclizing the product cleaved from the solid support;
(l') removing any protecting groups present on functional groups of any members of the chain of amino acid residues and, optionally, any protecting group(s) which may in addition be present in the molecule; and
(m') optionally, converting the product thus obtained into a pharmaceutically acceptable salt or converting a pharmaceutically acceptable, or unacceptable, salt thus obtained into the corresponding free compound of formula I or into a different, pharmaceutically acceptable, salt.

11. The process according to claim 9 wherein the process is modified for the manufacture of enantiomers of the compounds in which enantiomers of all chiral starting materials are used.

12. A The process according to claim 10 wherein the process is modified for the manufacture of enantiomers of the compounds in which enantiomers of all chiral starting materials are used.

* * * * *

UNITED STATES PATENT AND TRADEMARK OFFICE
CERTIFICATE OF CORRECTION

PATENT NO. : 9,518,092 B2  
APPLICATION NO. : 14/495737  
DATED : December 13, 2016  
INVENTOR(S) : Zumbrunn et al.

Page 1 of 1

It is certified that error appears in the above-identified patent and that said Letters Patent is hereby corrected as shown below:

In the Specification

Column 74, Lines 35-36:  
Delete: "…which is repeated is repeated for…"  
And insert: -- …which is repeated for… --

Column 77, Line 57:  
Delete: "…pepdidomimetics…"  
And insert: -- …peptidomimetics… --

Column 85, Line 17:  
Delete: "…washed with once with 7mL…"  
And insert: -- …washed once with 7mL… --

Column 98, Line 29:  
Delete: "…(at 370)…"  
And insert: -- …(at 37°)… --

In the Claims

Column 240, Line 37:  
Delete: "…A The process…"  
And insert: -- …The process… --

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*